US011897917B2

(12) United States Patent
Fascione et al.

(10) Patent No.: US 11,897,917 B2
(45) Date of Patent: Feb. 13, 2024

(54) BIOCONJUGATION OF POLYPEPTIDES

(71) Applicant: The University of York, Heslington (GB)

(72) Inventors: Martin A. Fascione, Heslington (GB); Richard J. Spears, Heslington (GB); Robin Brabham, Heslington (GB); Darshita Budhadev, Heslington (GB); Tessa Keenan, Heslington (GB)

(73) Assignee: The University of York, Heslington (GB)

( * ) Notice: Subject to any disclaimer, the term of this patent is extended or adjusted under 35 U.S.C. 154(b) by 416 days.

(21) Appl. No.: 16/650,357

(22) PCT Filed: Sep. 27, 2017

(86) PCT No.: PCT/GB2017/052896
§ 371 (c)(1),
(2) Date: Mar. 24, 2020

(87) PCT Pub. No.: WO2019/063958
PCT Pub. Date: Apr. 4, 2019

(65) Prior Publication Data
US 2020/0317723 A1    Oct. 8, 2020

(51) Int. Cl.
| | | |
|---|---|---|
| C07K 1/107 | (2006.01) |
| C07K 1/13 | (2006.01) |
| C07D 205/04 | (2006.01) |
| C07D 207/06 | (2006.01) |
| C07D 207/16 | (2006.01) |
| C07D 211/06 | (2006.01) |
| C07D 295/027 | (2006.01) |
| C07D 403/04 | (2006.01) |
| B01J 27/24 | (2006.01) |

(52) U.S. Cl.
CPC ............ *C07K 1/1075* (2013.01); *B01J 27/24* (2013.01); *C07D 205/04* (2013.01); *C07D 207/06* (2013.01); *C07D 207/16* (2013.01); *C07D 211/06* (2013.01); *C07D 295/027* (2013.01); *C07D 403/04* (2013.01); *C07K 1/1077* (2013.01); *C07K 1/13* (2013.01)

(58) Field of Classification Search
CPC ...... B01J 27/24; C07K 1/1075; C07K 1/1077; C07K 1/13
See application file for complete search history.

(56) References Cited

U.S. PATENT DOCUMENTS

| | | |
|---|---|---|
| 5,445,090 A | 8/1995 | Conley, Jr. |
| 5,900,461 A | 5/1999 | Harris |
| 5,932,462 A | 8/1999 | Harris et al. |
| 6,436,386 B1 | 8/2002 | Roberts et al. |
| 6,437,025 B1 | 8/2002 | Harris et al. |
| 6,448,369 B1 | 9/2002 | Bentley et al. |
| 6,495,659 B2 | 12/2002 | Bentley et al. |
| 6,514,491 B1 | 2/2003 | Bentley et al. |
| 6,515,100 B2 | 2/2003 | Harris |
| 7,102,024 B1 | 9/2006 | Schwartz et al. |
| 2003/0191291 A1 | 10/2003 | Kochendoerfer et al. |
| 2012/0183566 A1 | 7/2012 | Barfield et al. |
| 2014/0134265 A1 | 5/2014 | Buggy et al. |

FOREIGN PATENT DOCUMENTS

WO    WO 2015/137883 A1    9/2015

OTHER PUBLICATIONS

El-Mahdi. Bioconjugate Chemistry, 2012, 24, 735-765 (Year: 2012).*
International Search Report and Written Opinion for International Patent Application No. PCT/GB2017/052896, dated, 13 pages.
International Preliminary Report on Patentablity for International Patent Application No. PCT/GB2017/052896, dated Mar. 31, 2020, 8 pages.
Biet al., "Thiazolidine-Masked α-Oxo Aldehyde Functionality for Peptide and Protein Modification", Bioconjugate Chemistry, vol. 28, No. 2, Dec. 27, 2016 (Dec. 27, 2016), pp. 325-329.
Spears et al., "Site-selective incorporation and ligation of protein aldehydes", Organic & Biomolecular Chemistry, vol. 14, No. 32, Jun. 30, 2016 (Jun. 30, 2016), pp. 7622-7638.
Northrup et al., "The First Direct and Enantioselective Cross-Aldol Reaction of Aldehydes", Journal of the American Chemical Society, American Chemical Society, US, vol. 124, No. 24, Jun. 19, 2002.
Ouafaa El-Mahdi & Oleg Melynk, "α-oxo aldehyde or glyoxylyl group chemistry in peptide conjugation", Bioconjugate Chemistry, vol. 24 No. 5, pp. 735-765 (2013).
Jefferson D. Revell & Helma Wennemers, "Functional group requirements within the peptide H-Pro-Pro-Asp-NH2 as a catalyst for aldol reactions", Tetrahedron vol. 63 pp. 8420-8424 (2007).
Nicole M. Okeley, "Metabolic Engineering of Monoclonal Antibody Carbohydrates for Antibody-Drug Conjugation", Bioconjugate Chemistry, vol. 24, 1650-1655 (2013).
Richard J. Spears & Martin A. Fascione, Poster Presentation: Protein Aldol Ligation (PAL): A chemical strategy for the site-specific multi-functionalisation of proteins, Internal University of York—Chemistry Department Poster Presentation, Oct. 2015.
Richard J. Spears and Martin A. Fascione, Poster Presentation: An organocatalytic aldol ligation for the site-selective chemical modification of proteins, Royal Society of Chemistry Conference Poster Presentation, Oct. 2016.
Diamantis et al., "Antibody-drug conjugates-an emerging class of cancer treatment", British journal of cancer 114.4 (2016): 362.

(Continued)

*Primary Examiner* — Noble E Jarrell
(74) *Attorney, Agent, or Firm* — Morgan, Lewis & Bockius, LLP

(57) ABSTRACT

Certain embodiments of the present invention relate to methods of forming and manipulating bioconjugates. Particularly, but not exclusively certain embodiments relate to methods of reversible carbon-carbon bond bioconjugation using aldol based chemical reactions at physiological conditions.

21 Claims, 36 Drawing Sheets
Specification includes a Sequence Listing.

(56) References Cited

OTHER PUBLICATIONS

Miyake-Stoner et al., "Generating Permissive Site-Specific Unnatural aminoacyl-tRNA Synthetases", Biochemistry, 2010, 49, 1667-1677.
Plass et al., "Genetically Encoded Copper-Free Click Chemistry." Angew Chem Engl. International Edition 50.17 (2011): 3878-3881.
Angew Chem Int Ed Engl. Aug. 11, 2006;45(32):5307-11—"N-terminal protein modification through a biomimetic transamination reaction".
Angew Chem Int Ed Engl. Aug. 28, 2017;56(36):10644-10655—"Palladium in the Chemical Synthesis and Modification of Proteins".
Nature Chemistry. vol. 6, pp. 352-361 (2014)—"Palladium-triggered deprotection chemistry for protein activation in living cells".

* cited by examiner

Figure 27
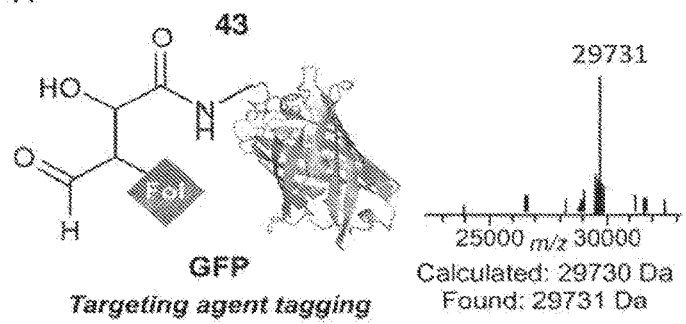
A 43
GFP
*Targeting agent tagging*
Calculated: 29730 Da
Found: 29731 Da
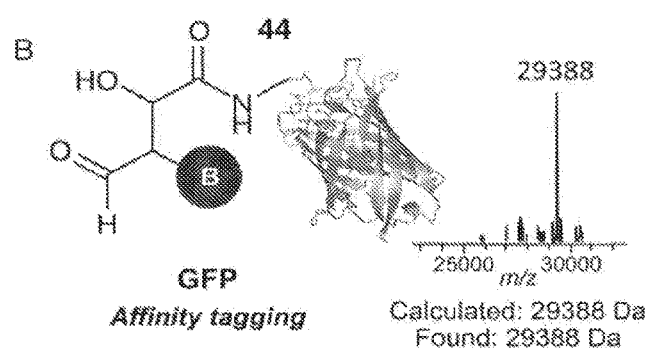
B 44
GFP
*Affinity tagging*
Calculated: 29388 Da
Found: 29388 Da
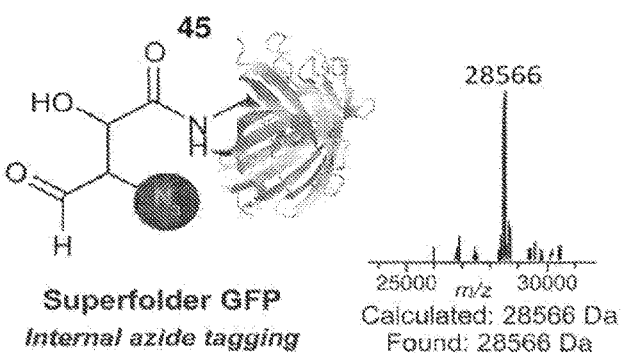
C 45
Superfolder GFP
*Internal azide tagging*
Calculated: 28566 Da
Found: 28566 Da Figure 30
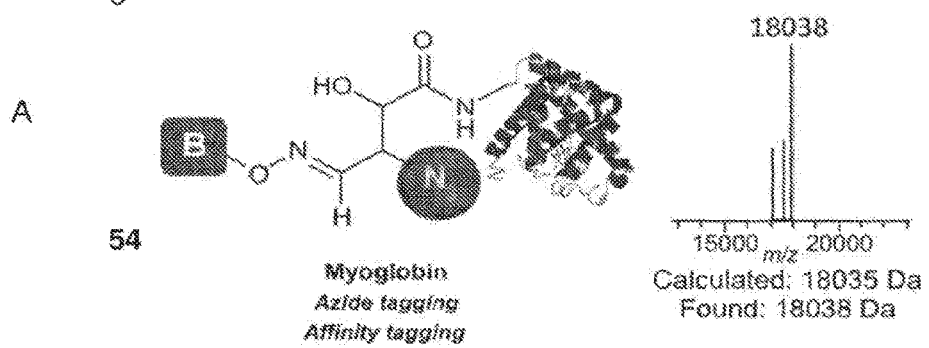
A
54
Myoglobin
*Azide tagging*
*Affinity tagging*
Calculated: 18035 Da
Found: 18038 Da
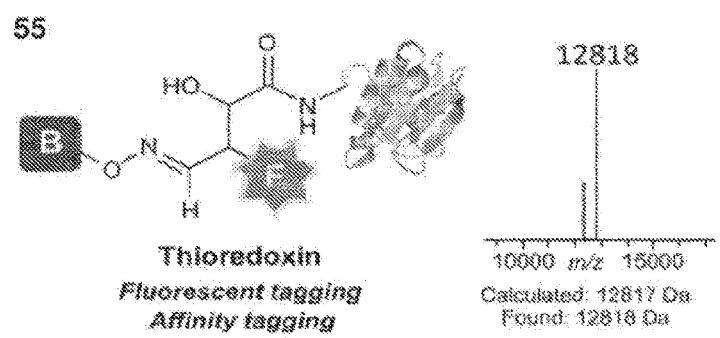
B
55
Thioredoxin
*Fluorescent tagging*
*Affinity tagging*
Calculated: 12817 Da
Found: 12818 Da Figure 39
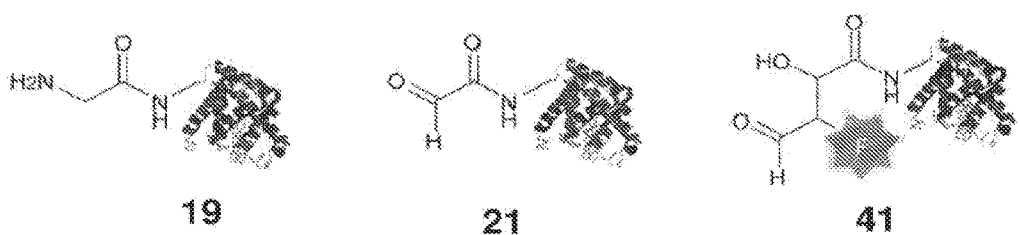
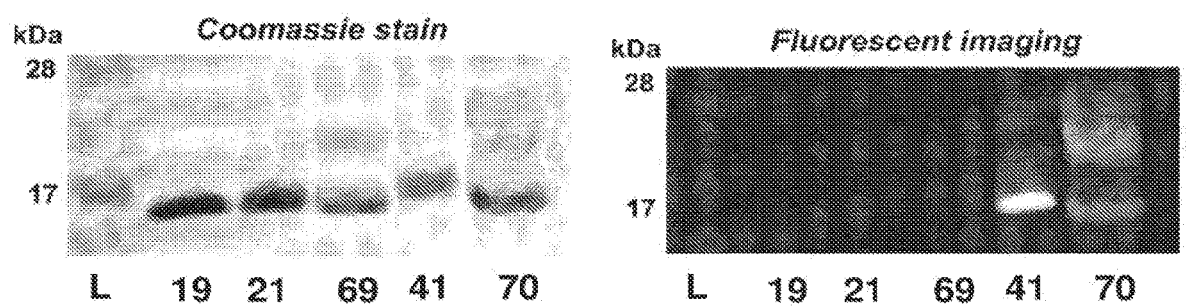

SEQUENCE LISTING

<160> NUMBER OF SEQ ID NOS: 7

<210> SEQ ID NO 1
<211> LENGTH: 253
<212> TYPE: PRT
<213> ORGANISM: Artificial
<220> FEATURE:
<223> OTHER INFORMATION: Mutated GFP(Y39TAG) protein
<220> FEATURE:
<221> NAME/KEY: X
<222> LOCATION: (48)..(48)
<223> OTHER INFORMATION: X= thiazolidine-substituted pyrrolysine

<400> SEQUENCE: 1

Met Asp Tyr Lys Asp Asp Asp Asp Lys Val Ser Lys Gly Glu Glu Leu
1               5                   10                  15

Phe Thr Gly Val Val Pro Ile Leu Val Glu Leu Asp Gly Asp Val Asn

```
                  20                  25                  30
Gly His Lys Phe Ser Val Ser Gly Glu Gly Glu Gly Asp Ala Thr Xaa
            35                  40                  45

Gly Lys Leu Thr Leu Lys Phe Ile Cys Thr Thr Gly Lys Leu Pro Val
        50                  55                  60

Pro Trp Pro Thr Leu Val Thr Thr Leu Thr Tyr Gly Val Gln Cys Phe
65                  70                  75                  80

Ser Arg Tyr Pro Asp His Met Lys Gln His Asp Phe Phe Lys Ser Ala
                85                  90                  95

Met Pro Glu Gly Tyr Val Gln Glu Arg Thr Ile Phe Phe Lys Asp Asp
            100                 105                 110

Gly Asn Tyr Lys Thr Arg Ala Glu Val Lys Phe Glu Gly Asp Thr Leu
        115                 120                 125

Val Asn Arg Ile Glu Leu Lys Gly Ile Asp Phe Lys Glu Asp Gly Asn
130                 135                 140

Ile Leu Gly His Lys Leu Glu Tyr Asn Tyr Asn Ser His Asn Val Tyr
145                 150                 155                 160

Ile Met Ala Asp Lys Gln Lys Asn Gly Ile Lys Ala Asn Phe Lys Ile
                165                 170                 175

Arg His Asn Ile Glu Asp Gly Ser Val Gln Leu Ala Asp His Tyr Gln
            180                 185                 190

Gln Asn Thr Pro Ile Gly Asp Gly Pro Val Leu Leu Pro Asp Asn His
        195                 200                 205

Tyr Leu Ser Thr Gln Ser Ala Leu Ser Lys Asp Pro Asn Glu Lys Arg
    210                 215                 220

Asp His Met Val Leu Leu Glu Phe Val Thr Ala Ala Gly Ile Thr Leu
225                 230                 235                 240

Gly Met Asp Glu Leu Tyr Lys His His His His His His
                245                 250

<210> SEQ ID NO 2
<211> LENGTH: 253
<212> TYPE: PRT
<213> ORGANISM: Artificial
<220> FEATURE:
<223> OTHER INFORMATION: mutated GFP protein (S-GFP(Y39TAG)
<220> FEATURE:
<221> NAME/KEY: X
<222> LOCATION: (48)..(48)
<223> OTHER INFORMATION: X= thiazolidine substituted pyrrolysine

<400> SEQUENCE: 2

Met Ser Tyr Lys Asp Asp Asp Asp Lys Val Ser Lys Gly Glu Glu Leu
1               5                   10                  15

Phe Thr Gly Val Val Pro Ile Leu Val Glu Leu Asp Gly Asp Val Asn
            20                  25                  30

Gly His Lys Phe Ser Val Ser Gly Glu Gly Glu Gly Asp Ala Thr Xaa
        35                  40                  45

Gly Lys Leu Thr Leu Lys Phe Ile Cys Thr Thr Gly Lys Leu Pro Val
    50                  55                  60

Pro Trp Pro Thr Leu Val Thr Thr Leu Thr Tyr Gly Val Gln Cys Phe
65                  70                  75                  80

Ser Arg Tyr Pro Asp His Met Lys Gln His Asp Phe Phe Lys Ser Ala
                85                  90                  95

Met Pro Glu Gly Tyr Val Gln Glu Arg Thr Ile Phe Phe Lys Asp Asp
            100                 105                 110
```

-continued

```
Gly Asn Tyr Lys Thr Arg Ala Glu Val Lys Phe Glu Gly Asp Thr Leu
            115                 120                 125

Val Asn Arg Ile Glu Leu Lys Gly Ile Asp Phe Lys Glu Asp Gly Asn
130                 135                 140

Ile Leu Gly His Lys Leu Glu Tyr Asn Tyr Asn Ser His Asn Val Tyr
145                 150                 155                 160

Ile Met Ala Asp Lys Gln Lys Asn Gly Ile Lys Ala Asn Phe Lys Ile
                165                 170                 175

Arg His Asn Ile Glu Asp Gly Ser Val Gln Leu Ala Asp His Tyr Gln
                180                 185                 190

Gln Asn Thr Pro Ile Gly Asp Gly Pro Val Leu Leu Pro Asp Asn His
            195                 200                 205

Tyr Leu Ser Thr Gln Ser Ala Leu Ser Lys Asp Pro Asn Glu Lys Arg
210                 215                 220

Asp His Met Val Leu Leu Glu Phe Val Thr Ala Ala Gly Ile Thr Leu
225                 230                 235                 240

Gly Met Asp Glu Leu Tyr Lys His His His His His His
                245                 250

<210> SEQ ID NO 3
<211> LENGTH: 247
<212> TYPE: PRT
<213> ORGANISM: Artificial
<220> FEATURE:
<223> OTHER INFORMATION: mutated super folded GFP (N150TAG)
<220> FEATURE:
<221> NAME/KEY: X
<222> LOCATION: (150)..(150)
<223> OTHER INFORMATION: X= thiazolidine-substituted pyrrolysine

<400> SEQUENCE: 3

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Phe Asn Ser His Xaa Val Tyr Ile Thr Ala Asp Lys Gln Lys Asn
145                 150                 155                 160

Gly Ile Lys Ala Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
            180                 185                 190
```

```
Pro Val Leu Leu Pro Asp Asn His Tyr Leu Ser Thr Gln Ser Val Leu
            195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys Gly
225                 230                 235                 240

Ser His His His His His His
                245

<210> SEQ ID NO 4
<211> LENGTH: 5
<212> TYPE: PRT
<213> ORGANISM: Artificial
<220> FEATURE:
<223> OTHER INFORMATION: Peptide

<400> SEQUENCE: 4

Leu Tyr Arg Ala Gly
1               5

<210> SEQ ID NO 5
<211> LENGTH: 6
<212> TYPE: PRT
<213> ORGANISM: Artificial
<220> FEATURE:
<223> OTHER INFORMATION: Peptide

<400> SEQUENCE: 5

Ser Leu Tyr Arg Ala Gly
1               5

<210> SEQ ID NO 6
<211> LENGTH: 52
<212> TYPE: DNA
<213> ORGANISM: Artificial
<220> FEATURE:
<223> OTHER INFORMATION: Primer

<400> SEQUENCE: 6
cactttatca tcatcatctt tgtaagacat ggttaattcc tcctgttagc cc          52

<210> SEQ ID NO 7
<211> LENGTH: 52
<212> TYPE: DNA
<213> ORGANISM: Artificial
<220> FEATURE:
<223> OTHER INFORMATION: Primer

<400> SEQUENCE: 7
gggctaacag gaggaattaa ccatgtctta caaagatgat gatgataaag tg          52
```

BIOCONJUGATION OF POLYPEPTIDES

FIELD OF THE INVENTION

Certain embodiments of the present invention relate to methods of forming and manipulating bioconjugates. Particularly, but not exclusively certain embodiments relate to methods which involve reversible carbon-carbon bond bioconjugation using aldol based chemical reactions at physiological conditions.

BACKGROUND TO THE INVENTION

The ability to site-selectively modify proteins with functional moieties is of major interest within the field of chemical biology, where the chemical ligation of functional molecules to proteins can be utilised in a number of fields and processes.

For example, bioconjugates including functional labels such as fluorescent groups, have enabled scientists to probe and perturb dynamic cellular processes in vitro, ex vivo, and even inside whole living organisms. Bioconjugates can be used as contrast agents in techniques such as magnetic resonance imaging (MRI) through conjugation of proteins such as antibodies to Gd(III) complexes or magnetite. Bioconjugates utilising fluorescent groups can also be utilised in a number of biochemical assays and techniques such as Förster resonance energy transfer (FRET) as well as localisation and binding assays that can be detected and quantified by detection of fluorescence.

Bioconjugates have also found use in improving therapeutics. For example, bioconjugates including molecules such as poly(ethylene) glycol (PEG) moieties can provide therapeutic peptides and proteins with enhanced water solubility, reduced immunogenicity, improved circulating half-life in vivo, enhanced proteolytic resistance, reduced toxicity, and improved thermal and mechanical stability. Conjugation also has utility in the formation of novel and personalised therapeutics such as antibody drug conjugates. Antibody Drug Conjugates (ADCs) are antibodies, such as monoclonal antibodies (mAbs) or fragments thereof, attached to biologically active drugs by chemical linkers through bioconjugation. By combining the unique targeting of mAbs with a drug, for example a cytotoxic cancer drug, ADCs allow sensitive discrimination between healthy and diseased tissue and therefore targeted therapy. The reversibility of the conjugation link also provides possibilities of drug release at specific locations or under specific conditions.

Also of importance is the development of methods and constructs that allow the reversible binding of proteins to surfaces. Immobilization and release of molecules, such as proteins, through bioconjugation has a number of utilities not just in research techniques for determining and discovering binding partners and ligands using methods such as phage display, but also in the design of biosensors which may require highly efficient, fast and simple methods of immobilising molecules to a specific location on a surface. These molecules may then be needed to be removed, exchanged or further modified.

Qualitative and quantitative detection of analytes in clinical samples is important for the early diagnosis of disease. The complexity and heterogeneity of clinical samples presents a challenging environment for the detection of individual molecules. Chromatographic purification of analytes prior to analysis is time-consuming and labor-intensive, and hence impractical. Accordingly, chemical and immunological methods have become favoured for medical diagnoses.

Traditional diagnostic methods require significant biochemical experimental protocols that are time-consuming and require specialized laboratory equipment, limiting their applicability. There is an urgent need to develop reusable biosensors for economical and rapid detection of analytes that would be usable in locations far removed from a laboratory setting, such as in the office of a medical doctor or in a remote geographical location. Most biosensors consist of biomolecules attached to surfaces via robust bioconjugation linkages. For example, a commercially available glucose sensor has been developed in which glucose oxidase is immobilized to an electrode surface. The immobilized enzyme converts glucose into hydrogen peroxide, which is recorded as a digital signal. This device is used to monitor glucose levels in diabetes patients. Some biosensor applications employ optical techniques such as surface plasmon resonance (SPR) to detect binding of analytes to biomolecules immobilized on a surface. SPR is used to measure binding of ligands, and yields accurate binding constant values.

In many of these devices the proteins need to be immobilised in a reversible manner to allow for different analytes to be detected easily and quickly using a simple, if not single device. Conjugation to a surface also has to be highly stable in order to prevent loss of a protein from a surface and therefore a loss of accuracy. Conjugation is also needed to be site specific and selective to allow the orientation of molecules, such as proteins, on a surface so that ligands or substrates can access binding regions or active sites.

Even though bioconjugates have a number of uses, the evolution of new applications for functionalized bioconjugates, such as protein bioconjugates, is hindered however by the relative paucity of methods available for chemical formation and manipulation of bioconjugates.

Aldehydes are simple chemical handles which while readily installed into proteins, have been relatively under exploited in bioconjugation studies. Conversely, their chemical reactivity has been thoroughly investigated in a small molecule context with a landmark being the emergence of 'organocatalysis' in the 2000s, which redefined the potency of simple aldehydes by demonstrating that small organic 'organocatalysts' could accelerate and control their transformation. From an initial focus on 'enamine' and 'imine' activation modes, the last decade has seen an exponential increase in the development of organocatalyst-mediated reactions with a range of new activation modes.

However, access to aldehyde groups in, for example proteins, can be problematic, with incorporation methods either requiring enzyme recognition sequences, location at a protein terminus, or both.

A number of enzymatic methods are known but suffer from these or other disadvantages. Use of formylglycine-generating enzyme, for example, will only form an aldehyde on the side-chain of a cysteine in a CXPXR sequence. It is also possible to utilises the enzyme farnesyl-transferase (PFTase) to catalyse the farnesylation of thiol containing side chains (e.g. cysteine residues) which can be used to install the farnesyl pyrophosphate (FPP) analogue, farnesyl aldehyde pyrophosphate (FAPP). This method also has the disadvantage though that the reaction is limited to cysteine residues located at the C-terminus of a protein within a tetrapeptide domain referred to as a CAAX box. Enzymatic incorporation of aldehydes using lipoic acid ligases (e.g. Lp1A) is also limited to lysine side chains located within the Lp1A acceptor peptide (LAP) with a maximum conversion to an aldehyde of 62%. Incorporation of 3-formyl-L-tyrosine using tubulin tyrosine ligase (TTL) is also limited to the C-terminal of peptides bearing a fourteen-amino acid Tub tag.

Aldehydes can also be incorporated in to the N-terminus of peptides or proteins by periodate-mediated oxidative cleavage of serine/threonine residues. However other amino acids, such as cysteines and methionine residues, can be oxidised which therefore requires use of excess methionine in the reaction which needs to be purified out after the reaction has occurred. Other methods that allow the incorporation of an aldehyde moiety only at the N-terminus of peptides or proteins also include the use of pyrodoxal-5-phosphate (PLP) in a transamination reaction, but this method also suffers from the fact that in certain cases the amino acid residues at positions 2 and 3 can affect the outcome of such transamination reactions. The lack of selectivity of these methods severely limits the use of aldehydes as handles for the conjugation of proteins to functional groups.

The technique of unnatural amino acid (UAA) mutagenesis has become a standard tool in chemical biology. Use of the pyrrolysine (Pyl) tRNA$_{CUA}$-tRNA synthetase (RS) pair from several species of archaeal methanogens has allowed access to proteins containing a wide range of non-canonical functionality, including alkenes, alkynes, azides and aryl halides, with generally excellent levels of site specificity.

Recent work has demonstrated that 2-thiazolidine derivative ThzK 2-OH could be recognised by the wild-type *Methanosarcina* barker pylRS and incorporated into proteins, with subsequent uncaging revealing an aldehyde suitable for biotinylation via oxime ligation. Notably, this aldehyde is glyoxylic, unlike benzylic aldehydes, with a more electrophilic character arising from the adjacent carbonyl. However, the conditions required to reveal the glyoxyl aldehyde are unsuitable for many proteins, with protein denaturing and/or precipitation often occurring at the very low pH required. The utility of this caged aldehyde would be greatly boosted by milder and protein-compatible conditions.

Numerous bioorthogonal reactions involving aldehydes have been developed to take advantage of the unique reactivity of this functional group and an impressive array of bioconjugates are possible, including antibody-drug conjugates, protein-protein conjugates, synthetic biological analogues, and labelled live cells.

The reaction of hydrazine and hydroxylamine/aminooxy reagents with proteins bearing aldehydes (or ketones) to form hydrazone and oxime bonds, respectively, are among the best-known methods for generating homogenous ligation products. These ligation strategies proceed via an iminium-type intermediate, and are by far the most common method of modifying aldehydes installed into proteins. However, hydrazone/oxime ligations result in the formation of a double bond between carbon and nitrogen (C=N) between protein and substrate (functional group) which is susceptible to hydrolysis over time.

A number of aldehyde conjugation reactions are highly valued for their ability to efficiently synthesize carbon-carbon (C—C) bonds, which are inherently stable under physiological conditions. The general application of existing C—C bioconjugation strategies are limited however by practical considerations, including the use of chemical probes which are only accessible through multi-step syntheses, or have reduced reactivity at neutral pH or in the presence of oxygen.

One such method involves the use of the Pictet-Spengler and iso-Pictet-Spengler reactions which lead to conjugates ligated via a carbon-carbon bond (C—C). Both these reactions are optimised at acidic pH though. This disadvantage is also true for the use of 2-amino benzamidoxime (ABAO) compounds in the modification of peptides and proteins bearing aldehyde handles, which also requires an acidic pH conditions. Ligation using ABAO compounds can also vary greatly in reaction rate and so are not consistent. It has also been shown that cross aldol reactions of aldehydes using L-proline as an organocatalyst (through an enamine activation mode) are water compatible but can cause protein degradation and precipitation, therefore negating their use in methods of bioconjugation.

It is also possible to use indium mediated allyation to form carbon-carbon bonds between aldehyde containing proteins and functional groups. The conditions used for such reactions though can lead to protein degradation. It is also noted that a maximum conversion of 54% has been reported. Low conversion percentages are also a disadvantage of the Wittig reaction which can also be used to form carbon-carbon bonds, giving only 65% conversion.

It is therefore apparent that there is a need for a highly efficient method of providing an aldehyde handle within a protein or peptide that does not require specific amino acid target sequences and can be formed using reaction conditions that do not lead to degradation of the protein or peptide. There is also a need for an improved method of reversibly conjugating functional groups to such aldehyde handles that can be performed at physiological conditions.

It is an aim of the present invention to at least partly mitigate the above-mentioned problems.

It is an aim of certain embodiments of the present invention to provide an improved method of providing an aldehyde moiety in a protein.

It is an aim of certain embodiments of the present invention to provide an improved method of providing an aldehyde moiety in a protein in a site selective manner.

It is an aim of certain embodiments of the present invention to provide an improved method of providing an aldehyde moiety in a protein wherein the method can be implemented at physiological pH and/or temperature.

It is an aim of certain embodiments of the present invention to provide an improved method of conjugating a functional group to a protein.

It is an aim of certain embodiments of the present invention to provide an improved method of reversibly conjugating a functional group to a protein.

It is an aim of certain embodiments of the present invention to provide a simplified method of conjugating a functional group to a protein.

It is an aim of certain embodiments of the present invention to provide an improved method of reversibly conjugating a functional group to a protein in a site selective manner.

It is an aim of certain embodiments of the present invention to provide an improved method of conjugating a functional group to a protein wherein the method can be implemented at a physiological pH and/or temperature.

SUMMARY OF INVENTION

In its broadest aspect, the present invention relates to the modification of polypeptides using aldol and/or oxime chemistry. Certain embodiments of the present invention provide an efficient way of conjugating biomolecules to polypeptides and also removing conjugated biomolecules from polypeptides.

According to a first aspect of the present invention there is provided a method of modifying a polypeptide, the method comprising:
 a. contacting a first polypeptide comprising a first aldehyde moiety with:
   i. an aldehyde donor molecule comprising a second aldehyde moiety; and
   ii. a catalyst molecule, under conditions sufficient for an aldol reaction to occur between the first aldehyde group and the second aldehyde group, such that a second polypeptide is formed;
wherein the second polypeptide comprises a third aldehyde moiety which is a beta-hydroxy aldehyde moiety and further wherein the catalyst molecule is a non-metallic organic compound.

Further details of certain embodiments of the first aspect are provided herein.

In a second aspect of the present invention, there is provided a method of modifying a polypeptide comprising:
 a) providing a first polypeptide comprising a beta-hydroxy aldehyde moiety; and
 b) contacting the first polypeptide with a substituted or unsubstituted aniline catalyst molecule under conditions sufficient for a retro-aldol reaction to occur so as to form a second polypeptide comprising an alpha-oxo aldehyde moiety.

Further details of certain embodiments of the second aspect are provided herein.

In a third aspect of the present invention, there is provided a method of modifying a polypeptide, the method comprising:
 a) contacting a first polypeptide with a catalyst molecule comprising palladium (0) or palladium (II);
wherein the first polypeptide comprises at least one unnatural amino acid molecule protected by a protecting group, under conditions suitable to deprotect the unnatural amino acid molecule to form a second polypeptide comprising an unnatural amino acid molecule comprising a deprotected α-oxo aldehyde moiety.

Further details of certain embodiments of the third aspect are provided herein.

DETAILED DESCRIPTION OF CERTAIN EMBODIMENTS OF THE INVENTION

As used herein, the following numbers refer to the following compounds unless otherwise stated:
 1: 2-methyl-thiazolidine lysine (2-OMe) having the following structure;

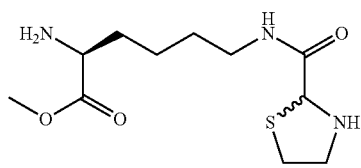 [SMILES: COC(=O)[C@@H](N)CCCCNC(=O)C1NCCS1]

2A: superfolded Green Fluorescent Protein with asparagine 150 mutated to thiazolidine lysine (ThzK) (sfGFP (N150ThzK)) (SEQ ID NO: 3)
 2B: GFP with tyrosine 39 mutated to thiazolidine lysine (ThzK) (GFP(Y39ThzK)) (SEQ ID NO: 1);
 3: 2-aminoethane thiol hydrochloride having the following structure:

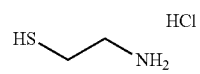

4: glyoxylic acid having the following structure:

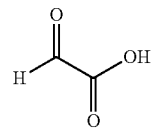

5. thiazolidine-2-carboxylic acid having the following structure:

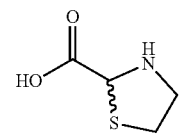

6: 3-(tert-butoxycarbonyl)thiazolidine-2-carboxylic acid having the following structure:

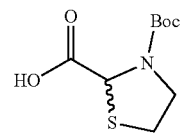

7: methyl 2-(tert-butoxycarbonylamino) hexanoate having the following structure:

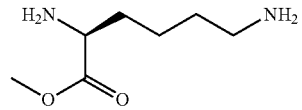

8. methyl 2-(tert-butoxycarbonylamino)-6-(thiazolidine-2-carboxamido-3-(tert-butoxycarbonyl)) hexanoate having the following structure:

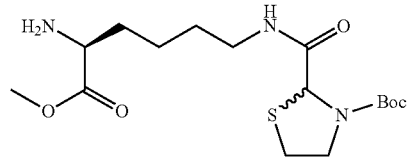 [SMILES: COC(=O)[C@@H](N)CCCCNC(=O)C1SCCN1C(=O)OC(C)(C)C]

9: Palladium(II) acetate (Pd(OAc)$_2$);
 10: dichlorobis[di-tert-butyl(4-dimethylaminophenyl) phosphine]palladium(II) (PdCl$_2$(amphos)$_2$);
 11: Allylpalladium(II) chloride dimer ([PdCl(allyl)]$_2$);
 12: Tris(dibenzylideneacetone)dipalladium(0) (Pd$_2$dba$_3$);
 13A: GFP with tyrosine 39 mutated to thiazolidine lysine and decaged to glyoxyl lysine (GFP(Y39GlyoxylK)) (SEQ ID NO: 1) 13B is hydrate of 13A;
 14: GFP with an N-terminal serine residue and tyrosine residue 39 mutated to 2-cyclooctynyloxycarbonyl lysine (Ser-GFP(Y39CycoOK)) (SEQ ID NO: 2);

15: SLYRAG peptide (SEQ ID NO: 5);
16: glyoxyl-LYRAG (SLYRAG peptide with N-terminal serine oxidised to a glyoxyl group).
16B is the hydrate of 16A;
17: Thioredoxin (Uniprot ID: POAA25-1/M26133);
18: glyoxyl-thioredoxin (Uniprot ID: POAA25-1/M26133.1, with the N-terminal serine converted to a glyoxyl-aldehyde);
19: horse heart myoglobin (Uniprot ID: P68082-1));
20: pyridoxal-5-phosphate (PLP) having the following structure;

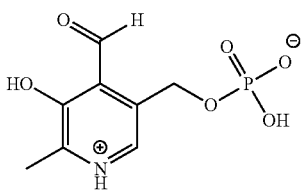 [SMILES: Cc1[nH+]cc(COP(=O)([O-])O)c(C=O)c1O]

21: glyoxyl-myoglobin (Uniprot ID: P68082-1 with the N-terminal glycine converted to a glyoxyl-aldehyde));
23: glyoxylLAG-GFP(Y39CycoOK) (oxidised version of 14);
24: synthetic aldehyde precursor of functional group aldehyde donor;
25: aldehyde donor functional group comprising a florescent moiety;
26: aldehyde donor functional group comprising a biotin moiety;
27: aldehyde donor functional group comprising a folate targeting moiety;
28: aldehyde donor functional group comprising an azide moiety;
30: butyraldehyde;
31: α-ethyl-β-hydroxy aldehyde myoglobin;
32: aldehyde donor;
33: L-proline;

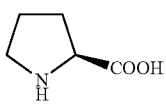

34: Pyrrolidine;

35: Piperidine;

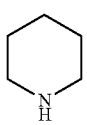

36: L-Azetidine 2 carboxylic acid;

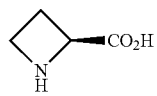

37: Homomorpholine;

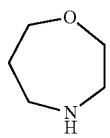

38: (S)-(−)-5-(2-Pyrrolidinyl)-1H-tetrazole;

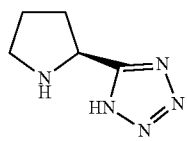

39: α-substituted-s-hydroxy aldehyde LYRAG;

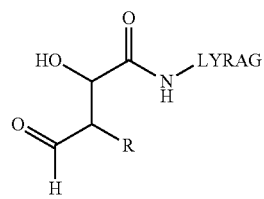

41: myoglobin conjugated to a functional group comprising a florescent moiety;
42: myoglobin conjugated to a functional group comprising an azide moiety;
43: GFP conjugated to a functional group comprising a folate moiety;
44: GFP conjugated to a functional group comprising a biotin moiety;
45: sfGFP conjugated to a functional group comprising an azide moiety;
46: α-ethyl-β-hydroxy aldehyde LYRAG;

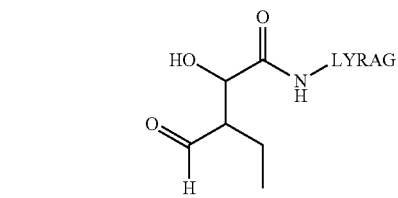

47: thioredoxin conjugated to a functional group comprising a florescent moiety;
48: thioredoxin conjugated to a functional group comprising a biotin moiety;
49: thioredoxin conjugated to a functional group comprising an azide moiety;

50: α-phenyl-β-hydroxy aldehyde LYRAG;

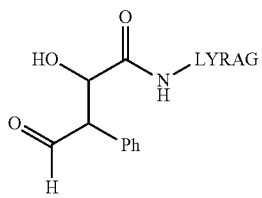

51: aminooxy nucleophile:

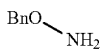

52: α-substituted-β-hydroxy benzyloxyimino LYRAG;

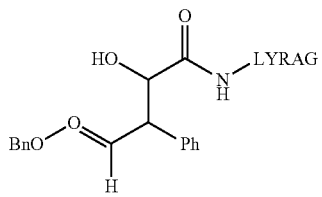

53: aminooxy nucleophile comprising a biotin moiety;

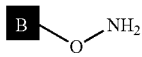

54: myoglobin conjugated to a functional group comprising an azide moiety and further conjugated to aminooxy biotin 53;
55: thioredoxin conjugated to a functional group comprising a florescent moiety and further conjugated to aminooxy biotin 53
56: aniline;

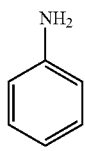

57: p-anisidine having the following structure:

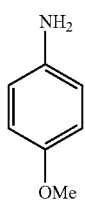

58: 5-methoxy anthranilic acid;

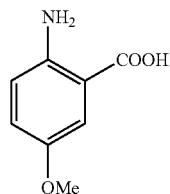 [SMILES: COc1ccc(N)c(C(=O)O)c1]

59: 2-Amino-4-nitrophenol;

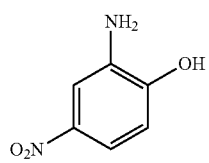 [SMILES: Nc1cc([N+](=O)[O-])ccc1O]

60: hydrophilic acylated surface protein A (HASPA) (AJ011808)
61: myristaldehyde having the structure;

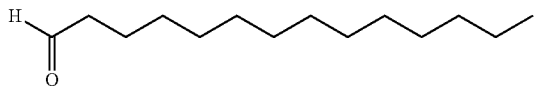

62: HASPA chemically conjugated to myristoyl
63: palmitoyl aminoxy nucleophile
64: HASPA chemically conjugated to myristoyl and palmitoyl
65: HASPA enzymatically conjugated to myristoyl
66: HASPA enzymatically conjugated to myristoyl and palmitoyl
67: fluorescently, biotinylated thioredoxin
68: sfGFP with asparagine 150 mutated to thiazolidine lysine and decaged to glyoxyl lysine (sfGFP (N150GlyoxylK)) (SEQ ID NO; 3)
69: Myoglobin conjugated to aminooxy PEG 2k
70: Myoglobin conjugated to a functional group comprising a fluorescent moiety and further conjugated to aminooxy PEG 2k

BRIEF DESCRIPTION OF THE FIGURES

Embodiments of the present invention will now be described hereinafter, by way of example only, with reference to the accompanying drawings in which:

FIG. 27 illustrates the structures of GFP conjugates 43 (A), 44 (B) and 45 (C) formed by OPAL reactions. Shown next to each structure is the LC-MS spectra for each corresponding species with the calculated and actual molecular weights indicated below each spectrum;

FIG. 30 illustrates the structures of protein conjugates 54 (A) and 55 (B) formed by OPAL and subsequent aniline organocatalyst-mediated oxime ligation reactions. Shown next to each structure is the LC-MS spectra for each corresponding species with the calculated and actual molecular weights indicated below each spectrum;

FIG. 39 shows SDS Page and fluorescent imaging results of myoglobin protein dually-derivatized with a fluorescent moiety and a PEG molecule.

DETAILED DESCRIPTION OF CERTAIN EMBODIMENTS

Figure 1:
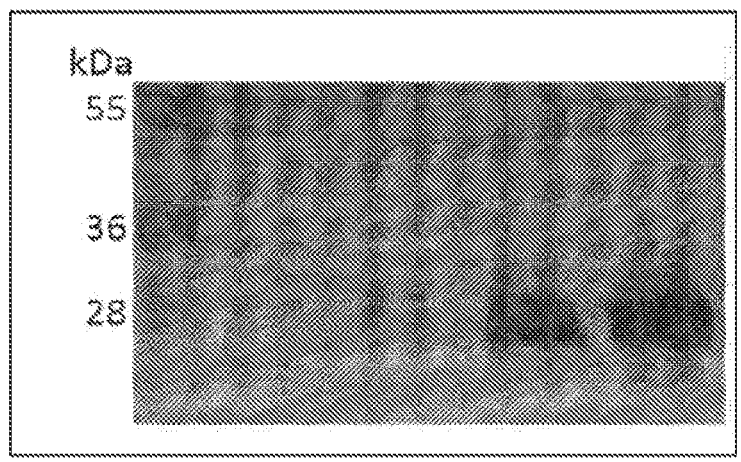
FIG. 1 shows SDS-PAGE gel analysis of purified GFP with tyrosine 39 mutated to thiazolidine lysine (ThzK) (GFP(Y39ThzK)) 2B. Purity of 2B is confirmed by the presence of a single band at approximately 28 kDa.

Further features of certain embodiments of the present invention are described below.

Unless otherwise indicated, standard techniques are used for recombinant DNA, oligonucleotide synthesis, and tissue culture and transformation (e.g., electroporation, lipofection). Enzymatic reactions and purification techniques are performed according to manufacturers specifications or as commonly accomplished in the art or as described herein. The foregoing techniques and procedures are generally performed according to conventional methods well known in the art and as described in various general and more specific references that are cited and discussed throughout the present specification. See for example, e.g., Sambrook et al. Molecular Cloning: A Laboratory Manual (3rd ed., Cold Spring Harbor Laboratory Press, Cold Spring Harbor, N.Y. (2001)), which is incorporated herein by reference. The nomenclatures utilised in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patents.

Units, prefixes and symbols are denoted in their Systëme International de Unitese (SI) accepted form. Numeric ranges are inclusive of the numbers defining the range. Unless otherwise indicated, amino acid sequences are written left to right in amino to carboxy orientation. All amino acid residues in proteins of embodiments of the invention are preferably of the L-configuration. However, D-configuration amino acids may also be present.

In a first aspect of the present invention, there is provided a method of modifying a polypeptide, the method comprising:

a. contacting a first polypeptide comprising a first aldehyde moiety with:
  i. an aldehyde donor molecule comprising a second aldehyde moiety; and
  ii. a catalyst molecule under conditions sufficient for an aldol reaction to occur between the first aldehyde group and the second aldehyde group, such that a second polypeptide is formed;

wherein the second polypeptide comprises a third aldehyde moiety which is a beta-hydroxy aldehyde moiety and further wherein the catalyst molecule is a non-metallic organic compound.

In an embodiment, the catalyst molecule comprises a secondary amine moiety or an acid addition salt thereof.

In one embodiment, a secondary amine moiety is of the formula $HNR^1R^2$ wherein $R^1$ and $R^2$ together with the nitrogen atom to which they are attached form a 3 to 7 membered ring which ring is optionally substituted by one or more optional substituents selected from —COOH, —COOR$^a$, —CONH$_2$, —CONHR$^a$, —CONR$^a$R$^b$ and a nitrogen containing cyclic group such as tetrazole,
  wherein R$^a$ and R$^b$ are independently selected from C1-6 alkyl and arylC1-6alkyl, e.g. methyl, ethyl or phenyl, benzyl and phenethyl.

Aptly, the catalyst molecule comprises a cyclic secondary amine molecule. For example, in certain embodiments, the catalyst molecule is selected from:

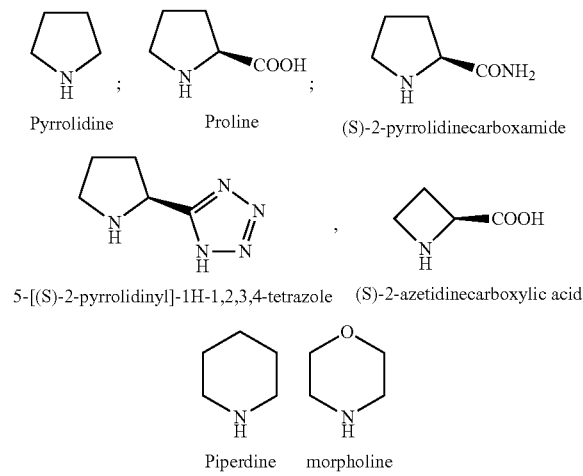

Pyrrolidine    Proline    (S)-2-pyrrolidinecarboxamide

5-[(S)-2-pyrrolidinyl]-1H-1,2,3,4-tetrazole    (S)-2-azetidinecarboxylic acid

Piperdine    morpholine

In certain embodiments, the catalyst molecule comprises a substituted cyclic secondary amine molecule, wherein optionally the substituted cyclic secondary amine molecule is substituted pyrrolidine.

In certain embodiments, the catalyst molecule comprises a tetrazole-substituted cyclic molecule, wherein optionally the tetrazole-substituted cyclic molecule is pyrrolidine substituted with tetrazole e.g. 2S-tetrazolylpyrrolidine.

In certain embodiments, the catalyst molecule is a compound of formula (I):

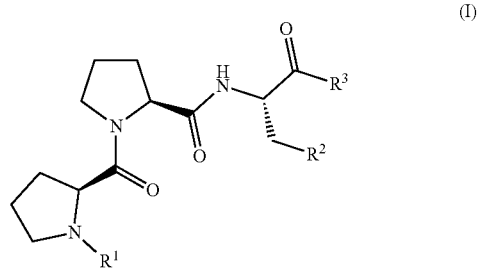

(I)

wherein:
  $R^1$ is selected from hydrogen, $C_{1-4}$alkyl and $C_{1-4}$alkylcarbonyl;
  $R^2$ is selected from carboxy, $C_{1-4}$alkylcarboxy, amido, $C_{1-4}$alkylamido, bis($C_{1-4}$alkyl)amido, sulfoxy and $C_{1-4}$alkylsulfoxy; and
  $R^3$ is selected from amino and methoxy.

In certain embodiments, $R^1$ is selected from hydrogen, methyl and acetyl.

In certain embodiments, $R^2$ is selected from carboxy, amido and sulfoxy.

In one embodiment, $R^1$ is hydrogen, $R^2$ is carboxy and $R^3$ is amino (H-Pro-Pro-Asp-NH$_2$).

In one embodiment, $R^1$ is acetyl, $R^2$ is carboxy and $R^3$ is amino (Ac-Pro-Pro-Asp-NH$_2$).

In one embodiment, $R^1$ is methyl, $R^2$ is carboxy and $R^3$ is amino (CH$_3$-Pro-Pro-Asp-NH$_2$).

In one embodiment, $R^1$ is hydrogen, $R^2$ is amido and $R^3$ is amino (H-Pro-Pro-Asn-NH$_2$).

In one embodiment, $R^1$ is hydrogen, $R^2$ is sulfoxy and $R^3$ is amino (H-Pro-Pro-Cys(SO$_3$H)—NH$_2$).

In one embodiment, $R^1$ is hydrogen, $R^2$ is carboxy and $R^3$ is methoxy (i-Pro-Pro-Asp-OCH$_3$).

In an embodiment, the method further comprises contacting the first polypeptide, the aldehyde donor molecule and the catalyst molecule in a buffer solution having a pH of between about 7 and 8, e.g. a pH of about 7.2 to 7.6 e.g. about 7.4.

In certain embodiments, the buffer solution is a phosphate buffer solution. In certain embodiments, the method further comprises contacting the first polypeptide, the aldehyde donor moiety and the catalyst molecule at a temperature of between about 4° and about 42° C. In certain embodiments, the method further comprises contacting the first polypeptide, the aldehyde donor moiety and the catalyst molecule at a temperature of about 37° C. In certain embodiments, the method further comprises contacting the first polypeptide, the aldehyde donor moiety and the catalyst molecule for at least 30 minutes e.g. 60 minutes, e.g. at least 120 minutes, at least 3 hours, at least 6 hours or at least 12 hours e.g. 16 hours or more. In certain embodiments, the method further comprises contacting the first polypeptide, the aldehyde donor moiety and the catalyst molecule for at least 24 hours.

In certain embodiments, the first polypeptide comprises the first aldehyde moiety at an internal sequence of the polypeptide; at a terminal loop, a C-terminus, or an N-terminus of the polypeptide; on a solvent-accessible region of the polypeptide when folded; and/or at a site of post-translational modification of the polypeptide that is native or non-native to the amino acid sequence of the polypeptide.

In certain embodiments, the aldehyde donor moiety is a small molecule moiety. In certain embodiments, the aldehyde donor moiety comprises an aryl substituent.

In certain embodiments, the aldehyde donor moiety comprises a moiety having the structure of:

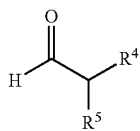

wherein $R^4$ and $R^5$ are independently selected from $C_{1-10}$alkyl, aryl, $C_{1-10}$alkoxy, $C_{1-10}$aryloxy, $C_{1-10}$alkylthio, arylthio, $C_{1-10}$alkylamino and bis($C_{1-10}$alkyl)amino.

In certain embodiments, the aldehyde donor moiety is selected from acetaldehyde and phenylacetaldehyde.

In certain embodiments, the aldehyde donor moiety further comprises a functional moiety and the method comprises incorporating the functional moiety into the second polypeptide.

In certain embodiments, the method further comprises incorporating the functional moiety into the second polypeptide at the alpha carbon position of the third aldehyde moiety.

In certain embodiments, the first aldehyde moiety is comprised in a glycan moiety covalently bonded to the polypeptide. Aptly, the polypeptide is an antibody or fragment thereof.

In certain embodiments, the glycan moiety is an unnatural glycan moiety. In certain embodiments, the unnatural glycan moiety contains a glyoxyl aldehyde.

Aptly the functional moiety is selected from a fluorescent label, an affinity tag, a conjugation moiety, a water soluble polymer and a targeting moiety.

In certain embodiments, the conjugation moiety is an azide moiety.

In certain embodiments, the method further comprises conjugating a further functional moiety to the second polypeptide via the conjugation moiety. In certain embodiments, the method comprises, prior to step (a), contacting a polypeptide with an oxidising reagent to generate the first aldehyde moiety on the polypeptide and form the first polypeptide.

Aptly, the oxidising reagent is periodate. In certain embodiments, the periodate comprises at least one of a periodic acid, a sodium periodate, an alkali metal periodate, and a potassium periodate.

In certain embodiments, the method comprises oxidising a N-terminal serine residue or a N-terminal threonine residue to form an alpha-oxy aldehyde moiety. Aptly, the oxidising reagent is pyridoxal-5-phosphate (PLP) and the method comprises oxidising a N-terminal lysine residue to form an alpha-oxy aldehyde moiety.

In certain embodiments, the method comprises prior to step (a) a step of:
b) modifying a polypeptide to incorporate an aldehyde moiety at a pre-determined location to form the first polypeptide.

In certain embodiments, the step of modifying the polypeptide to incorporate an aldehyde moiety at a pre-determined location to form the first polypeptide comprises a method according to certain embodiments of the third aspect of the present invention described herein. Thus in certain embodiments, step (b) comprises deprotecting a protecting group bonded to an unnatural amino acid using a palladium (0) catalyst molecule or a palladium (II) catalyst molecule. Further details are provided herein.

In certain embodiments, the method further comprises a step of:
c) contacting the second polypeptide with:
i. a substituted or unsubstituted aniline catalyst molecule; and
ii. a substituted hydroxylamine molecule, wherein the substituent comprises a further functional moiety, under conditions sufficient for an oxime reaction to occur between the substituted hydroxylamine molecule and the beta-hydroxy aldehyde moiety to form a third polypeptide comprising the further functional moiety.

Thus, certain embodiments of the present invention provide a method in which a dually-derivatized polypeptide is formed by a first aldol reaction and a subsequent oxime reaction.

In certain embodiments, the method comprises contacting the polypeptide and the catalyst molecule in an aqueous solution having a pH of between about 6.5 and 8. In certain embodiments, the aqueous solution has a pH of between about 7 and 7.6 e.g. about 7.1, 7.2, 7.3, 7.4, 7.5 or 7.6.

In certain embodiments, the substituted hydroxylamine molecule has a structure of the following formula:

In some embodiments, the substituted hydroxylamine has a structure of the following formula:

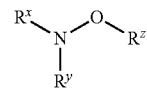

wherein at least one of $R^x$, $R^y$ and $R^z$ is H.

In certain embodiments, the substituted hydroxylamine molecule is an O-hydroxylamine. In certain embodiments, the substituted hydroxylamine molecule is an N-hydroxylamine.

In certain embodiments, the aniline catalyst molecule is selected from:

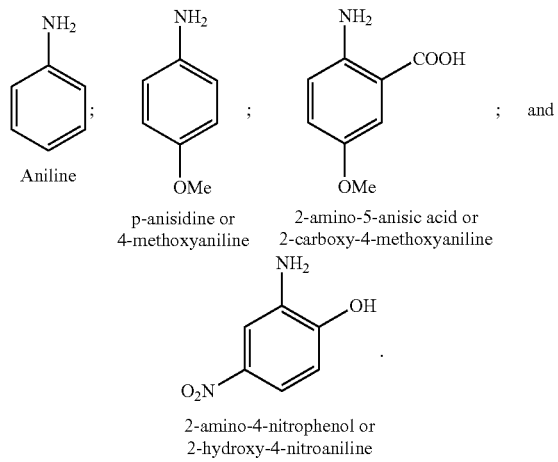

In certain embodiments, the method further comprises contacting the polypeptide, the aniline catalyst in a buffer solution, wherein the buffer solution has a concentration of between at or below 100 mM.

In certain embodiments, the method further comprises contacting the second polypeptide, the substituted or unsubstituted aniline catalyst molecule and the substituted hydroxylamine molecule in a buffer solution having a pH of between about 6.5 to about 8, e.g. about 7.3 to about 7.6.

In a second aspect of the present invention, there is provided a method of modifying a polypeptide comprising:
a) providing a first polypeptide comprising a beta-hydroxy aldehyde moiety; and
b) contacting the first polypeptide with a substituted or unsubstituted aniline catalyst molecule under conditions sufficient for a retro-aldol reaction to occur so as to form a second polypeptide comprising an alpha-oxo aldehyde moiety.

In certain embodiments, the aniline catalyst molecule is selected from

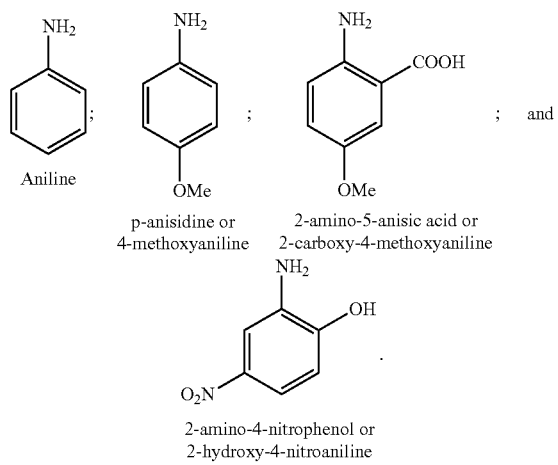

Aniline p-anisidine or
4-methoxyaniline 2-amino-5-anisic acid or
2-carboxy-4-methoxyaniline 2-amino-4-nitrophenol or
2-hydroxy-4-nitroaniline In certain embodiments, the method comprises contacting the first polypeptide with the substituted or unsubstituted aniline catalyst molecule in a buffer solution having a pH of between about 6.5 and about 8, e.g. between 6.8 and about 7.6.

In certain embodiments, the method comprises contacting the first polypeptide with the substituted or unsubstituted aniline catalyst molecule, wherein the substituted or unsubstituted aniline catalyst molecule is provided in a concentration of about 80 mM to about 300 mM, optionally about 100 to about 250 mM, e.g. about 100 mM or about 200 mM. In certain embodiments, the buffer solution is a phosphate buffer solution.

In certain embodiments, the beta-hydroxy aldehyde moiety is located at an internal sequence of the first polypeptide; at a terminal loop, a C-terminus, or an N-terminus of the first polypeptide; on a solvent-accessible region of the first polypeptide when folded; and/or at a site of post-translational modification of the first polypeptide that is native or non-native to the amino acid sequence of the first polypeptide.

In certain embodiments, the alpha-oxo aldehyde moiety is located at an internal sequence of the second polypeptide; at a terminal loop, a C-terminus, or an N-terminus of the second polypeptide; on a solvent-accessible region of the second polypeptide when folded; and/or at a site of post-translational modification of the second polypeptide that is native or non-native to the amino acid sequence of the second polypeptide.

In certain embodiments, the method of the second aspect of the invention may be used to modify a surface-bound polypeptide so as to release the polypeptide from the surface.

In a third aspect of the present invention, there is provided a method of modifying a polypeptide, the method comprising:
a) contacting a first polypeptide with a catalyst molecule comprising palladium (0) or palladium (II);
wherein the first polypeptide comprises at least one unnatural amino acid molecule protected by a protecting group, under conditions suitable to deprotect the unnatural amino acid molecule to form a second polypeptide comprising an unnatural amino acid molecule comprising a deprotected α-oxo aldehyde moiety.

In certain embodiments, the unnatural amino acid is a lysine analog. Aptly, the unnatural amino acid molecule comprises a substituted-pyrrolysine. Aptly, the substituent is a thiazolidine compound or derivative thereof.

Aptly, the thiazolidine derivative is thiazolidine-2-carbonyl and optionally wherein the substituted pyrrolysine is NE-(Thiazolidine-2-carbonyl)-L-lysine methyl ester.

In certain embodiments, the method comprises contacting the first polypeptide and the aqueous solution at a pH of around 6.5 to 8. e.g. at a pH of around 7.4.

In certain embodiments the method comprises, prior to step (a), a step of incorporating the unnatural amino acid residue protected by a first protecting group into the first polypeptide.

Aptly, the step of incorporating the unnatural amino acid residue protected by a first protecting group into the first polypeptide comprises:
i) providing a nucleic acid molecule encoding the first polypeptide, the nucleic acid molecule comprising an orthogonal codon encoding the unnatural amino acid molecule;
ii) translating the nucleic acid molecule in the presence of an orthogonal tRNA synthetase and tRNA pair capable of recognising the orthogonal codon and incorporating the unnatural amino acid molecule protected by the protecting group into the first polypeptide.

In certain embodiments, the method further comprises providing a nucleic acid molecule encoding the orthogonal tRNA and a nucleic acid molecule encoding a tRNA synthetase, wherein the orthogonal tRNA and tRNA synthetase pair are derived from archaeon *Methanosarcina barkeri* or *Methanosarcina mazei*.

Aptly, the orthogonal tRNA is tRNA (Pyl) and the tRNA synthetase is pyrrolysyl-tRNA synthetase (PylRS). Aptly, the orthogonal codon is an amber stop codon and is optionally selected from UAG or TAG.

In certain embodiments, the method further comprises prior to or simultaneously with step (a), a step of contacting a cell comprising the nucleic acid molecule encoding the first polypeptide with an aqueous solution comprising the unnatural amino acid residue, wherein optionally the solution comprises the unnatural amino acid residue at a concentration of between about 3 mM to about 10 mM, e.g. about 5 mM. Aptly, the aqueous solution comprises sodium hydroxide.

In certain embodiments, the catalyst molecule is a catalyst molecule selected from: tris(dibenzylideneacetone)dipalladium ($Pdd_3ba_2$) and allylpalladium(II) chloride dimer ($Pd(allyl)Cl]_2$.)

In certain embodiments, the catalyst molecule is tris(dibenzylideneacetone)dipalladium and the method comprises contacting the polypeptide with the catalyst molecule for at least 12 hours, e.g. 18 hours, e.g. 20 hours, e.g. 24 hours or for example at least 36 hours.

In certain embodiments, the catalyst molecule comprises allylpalladium(II) chloride dimer and the method comprises contacting the polypeptide with the catalyst molecule for at least 30 minutes e.g. at least 45 minutes, e.g. for 60 minutes or more.

In certain embodiments, the method comprises contacting the polypeptide with the catalyst molecule for no longer than about 2 hours. In certain embodiments, the method comprises contacting the first polypeptide with the catalyst molecule in a relative concentration of about 1 (polypeptide):1 (catalyst) or less than 1 (polypeptide):1 (catalyst).

In certain embodiments, the catalyst molecule is provided in a concentration of less than 500 µM. In certain embodiments, at least 80% e.g. at least 90% of the first polypeptide is converted to the second polypeptide.

In certain embodiments, the method further comprises a step of contacting the second polypeptide with an oxidation agent under conditions suitable to form a third polypeptide comprising a deprotected α-oxo aldehyde moiety and a further aldehyde moiety, wherein the further aldehyde moiety is positioned at an N-terminal of the polypeptide.

In certain embodiments, the oxidation agent comprises a periodate, and is optionally sodium periodate.

It will be appreciated that the methods of the first aspect, the second aspect and the third aspect may be combined accordingly. For example, a first polypeptide of the first aspect of the invention may be a second polypeptide of the third aspect i.e. a polypeptide which comprises an unnatural amino acid molecule comprising a deprotected α-oxo aldehyde moiety. Thus, in certain embodiments of the present invention, the method comprises a first step of expressing a polypeptide comprising an unnatural amino acid molecule protected by a protecting group and deprotecting the unnatural amino acid molecule to form an unnatural amino acid molecule comprising a deprotected α-oxo aldehyde. Such deprotecting can be carried out using a palladium (0) or a palladium (II) catalyst molecule.

Furthermore, certain methods of the present invention may comprise carrying out a retro-aldol reaction on the first polypeptide of the second aspect of the invention on a second polypeptide produced by the methods of the first aspect of the present invention.

Definitions

As used herein, the terms "polypeptide", "peptide" and "protein" are used interchangeably herein to refer to a polymeric form of amino acids of any length. Unless specifically indicated otherwise, "polypeptide", "peptide" and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like. The terms "polypeptide", "peptide" and "protein" also refer to proteins which comprise one or more post-translational modification such as for example phosphylation, glycosylation, lipidation and ubiquitination. Specific examples of polypeptides are provided herein.

The term "glycosylation" may include for example N-, O- and C-linked glycosylation, glypiation and phosphoglycosylation. Lipidation may refer to:
C-terminal glycosyl phosphatidylinositol (GPI) anchor;
N-terminal myristoylation;
S-myristoylation; and
S-prenylation In certain embodiments, the polypeptide is glycosylated. In certain embodiments, the method comprises providing an aldehyde moiety to a glycan moiety attached to the polypeptide.

As used herein an amino acid "modification" refers to a substitution, addition or deletion of an amino acid, and includes substitution with or addition of any of the 20 amino acids commonly found in mammalian proteins, as well as atypical or unnatural amino acids. Throughout the application, all references to a particular amino acid position by number (e.g. position 28) refer to the amino acid at that position of proteins or peptides of certain embodiments of the present invention. Modifications also include incorporation into a polypeptide and/or conversion of chemical groups incorporated and/or conversion of naturally occurring chemical groups such as chemical groups located at the N- or C-terminus of a polypeptide and or chemical groups of amino acid residues of a polypeptide.

As used herein, the term "naturally-occurring" refers to anything (e.g., proteins, amino acids, or nucleic acid sequences) that are found in nature. Conversely, the term "non-naturally occurring" refers to anything that is not found in nature (e.g., recombinant nucleic acids and protein sequences produced in the laboratory, modifications of the native sequence or modifications of naturally occurring amino acid side chains).

As used herein, the term "unnatural amino acid" refers any amino acid molecule that is not one of the 20 amino acids naturally occurring and genetically encoded in mammalian proteins. Thus, included by the definition of "unnatural amino acids" are modified amino acids, amino acid analogues, e.g. selenocysteine and pyrrolysine that are known to be incorporated into polypeptides but do not naturally occur in mammalians. The term "unnatural amino acid molecule" may also encompass derivatives of pyrroysine for example.

As used herein, the terms "N-terminal" and "N-terminus" refer to the terminal amino acid residue of a polypeptide having a free amine group.

As used herein, the terms "C-terminal" and "C-terminus" refer to the terminal amino acid residue of a polypeptide having a free carboxyl group.

As used herein, in reference to a polypeptide or an amino acid sequence of a polypeptide, the terms "internal site" and "internal sequence" are used interchangeably to refer to a region of the polypeptide that is not at the N-terminus or at the C-terminus.

As used herein the term "target polypeptide" refers to a polypeptide that is to be modified by one or more methods as described herein.

As used herein, the terms "native amino acid sequence" or "parent amino acid sequence" are used interchangeably, in the context of a polypeptide to refer to the amino acid sequence of the polypeptide prior to modification according to certain embodiments of the methods described herein.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

As used herein the term, "aldehyde" represents the broad class of organic compounds having the generic formula RCHO, and characterized by an unsaturated carbonyl functionality (C=O).

As used herein, the term "α-oxoaldehyde" refers to the broad class of aldehydes having the generic formula RCO-CHO, characterised by an oxo group attached to the alpha-carbon of the aldehyde.

As used herein, the terms "aldol" and "hydroxy-aldehyde" are used interchangeably to refer to the broad class of organic compounds having the general formula $R^1COHCR^2COR^3$. Aldols include any compounds containing both an alcohol and an aldehyde group.

As used herein, the term "β-hydroxy-aldehyde" refers to the broad class of aldehydes having the generic formula $R^1COHCR^2COH$ characterised by a hydroxyl group attached to the beta carbon.

As used herein, the term "oxime" refers to compounds with the general formula $R^1R^2C=NOH$. The term "oxime reaction" refers to a reaction between a hydroxylamine moiety and an aldehyde moiety forming an oxime product.

As used herein, the term "substituted hydroxyl amine" refers to compounds with the general formula $NH_2OH$ wherein at least one hydrogen atom is substituted.

As used herein the term "aldol reaction" refers to a reaction wherein an enolate of an aldehyde reacts at the α-carbon with a carbonyl of another molecule to form a β-hydroxy aldehyde.

As used herein the term "retro-aldol reaction" refers to the reverse of an aldol reaction, wherein a β-hydroxy aldehyde fragments to form a carbonyl compound and the enolate of an alpha-acidic carbonyl compound.

As used herein, the term "enamine" refers to any amine containing the double bond linkage C=C—N.

As used herein, the term "aromatic amine" refers to an organic compound comprising an aromatic group attached to an amine group.

As used herein, the term "secondary amine" refers to a molecule comprising an ammonia moiety wherein two of the hydrogen atoms have been substituted by hydrocarbon groups.

As used herein the term "enolizable" refers to any aldehyde bearing a hydrogen on an "alpha carbon" (the carbon atom once removed from that bearing the carbonyl functionality), wherein said alpha hydrogen (proton) may be readily removed by an exogenous base or via intra molecular tautomerization to form an enolate. Accordingly, the term "non-enolizable" refers to any aldehyde not bearing any hydrogen atoms on the alpha carbon. Aptly, the aldehyde donor molecule described herein comprises an enolizable aldehyde moiety.

As used herein the term "tautomer" refers to constitutional isomers of organic compounds that readily interconvert. The chemical reaction interconverting the two constitutional isomers is referred to as "tautomerization".

As used herein the term "nucleophile" or "nucleophilic" refers to an electron rich compound, or moiety thereof.

As used herein, the term "OPAL" refers to an organocatalyst-mediated protein aldol ligation as described herein.

As used herein, the term "catalyst" refers to substances that alter the rate of a chemical reaction. A catalyst may either increase the chemical reaction rate (i.e. a "positive catalyst") or decrease the reaction rate (i.e. a "negative catalyst"). The catalysts provided herein typically work as either an L-enantiomer or as a D-enantiomer.

As used herein, the term "buffer solution" or "buffer", refers to an aqueous solution consisting of a mixture of a weak acid and its conjugate base or a weak base and its conjugate acid. In particular, a physiological buffer emulates physiological conditions, e.g. has a pH, ranging from 7.0 to 8.0, and an isotonic salt concentration, e.g. between 0.7 and 1.1% salt (e.g. NaCl), preferably around 0.9% salt (e.g. NaCl). Non-limiting examples of buffers include Tris-buffered saline, phosphate buffered saline (PBS) and the like.

As used herein the terms "substituted" and "substituent" refer to hydrocarbyl, alkyl, aryl, or other moieties wherein, at least one hydrogen atom bound to a carbon (or other) atom is replaced with one or more non-hydrogen substituents. Examples of such substituents include, without limitation: such as halo, hydroxyl, sulfhydryl, $C_1$-$C_{24}$alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$alkylcarbonyloxy (—O—CO-alkyl) and CO—$C_{24}$arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$arylcarbonato (—O—(CO)—O-aryl), carboxy (—COOH), carboxylato (—COO—), carbamoyl (—(CO)—$NH_2$), mono-($C_1$-$C_{24}$alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_6$-$C_{24}$aryl)-substituted carbamoyl (—(CO)—NH-aryl), di-($C_5$-$C_{24}$aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—$NH_2$), mono-($C_1$-$C_{24}$alkyl)-substituted thiocarbamoyl (—(CO)—NH($C_1$-$C_{24}$alkyl)), di-($C_1$-$C_{24}$alkyl)-substituted thiocarbamoyl (—(CO)—N($C_1$-$C_{24}$alkyl)$_2$), mono-($C_1$-$C_{24}$ aryl)-substituted thiocarbamoyl (—(CO)—NH-aryl), di-($C_1$-$C_{24}$ aryl)-substituted thiocarbamoyl (—(CO)—N($C_1$-$C_{24}$ aryl)$_2$), di-N—($C_1$-$C_{24}$ alkyl), N—($C_1$-$C_{24}$ aryl)-substituted thiocarbamoyl, carbamido (—NH—(CO)—$NH_2$), cyano(—C≡N), cyanato (—O—C≡N), thiocyanato (—S—C≡N), formyl (—(CO)—H), thioformyl (—(CS)—H), amino (—$NH_2$), mono-($C_1$-$C_{24}$alkyl)-substituted amino, di-($C_1$-$C_{24}$ alkyl)-substituted amino, mono-($C_5$-$C_{24}$aryl)-substituted amino, di-($C_5$-$C_{24}$aryl)-substituted amino, $C_2$-$C_{24}$alkylamido (—NH—(CO)-alkyl), $C_6$-$C_{24}$arylamido (—NH—(CO)-aryl), imino (—CR—NH where R=hydrogen, $C_1$-$C_{24}$alkyl, $C_5$-$C_{24}$aryl, $C_6$-$C_{24}$alkaryl, $C_4$-$C_{24}$aralkyl, etc.), $C_2$-$C_{24}$alkylimino (—CR=N(alkyl), where R=hydrogen, $C_1$-$C_{24}$alkyl, $C_5$-$C_{24}$aryl, $C_5$-$C_{24}$alkaryl, $C_6$-$C_{24}$aralkyl, etc.), arylimino (—CR—N (aryl), where R=hydrogen, $C_1$-$C_{20}$ alkyl, $C_5$-$C_{24}$aryl, $C_6$-$C_{24}$alkaryl, $C_6$-$C_{24}$ aralkyl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), $C_5$-$C_{24}$arylsulfanyl (—S-aryl; also termed "arylthio"), $C_1$-$C_{24}$ alkylsulfinyl (—(SO)-alkyl), C—$C_{24}$ arylsulfinyl (—(SO)-aryl), $C_1$-$C_{24}$ alkylsulfonyl (—$SO_2$-alkyl), $C_5$-$C_{24}$ arylsulfonyl (—$SO_2$-aryl), boryl (—$BH_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—$PO_2$), and phosphino (—$PH_2$); and the hydrocarbyl moieties $C_1$-$C_{24}$ alkyl (preferably $C_1$-$C_2$ alkyl, more preferably $C_1$-$C_6$ alkyl), $C_2$-$C_{24}$ alkenyl, $C_2$-$C_{24}$ alkynyl, $C_5$-$C_{24}$ aryl (e.g. $C_5$-$C_{14}$ aryl), $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those mentioned above.

As used herein the terms "optional" or "optionally" refer to the fact that the subsequently described circumstance may or may not occur, so that the description includes instances where the circumstance occurs and instances where it does not. For example, the phrase "optionally substituted" refers to a non-hydrogen substituent may (substituted) or may not (unsubstituted) be present on a given atom, and, thus, the description includes structures wherein a non-hydrogen substituent is present and structures wherein a non-hydrogen substituent is not present.

As used herein, the term "bioorthogonal", "orthogonal" or "bioorthogonal functional group" refer to a functional group or chemical reaction that can occur inside a living cell, tissue, or organism without interfering with native biological or biochemical processes.

In certain embodiments, "(bio)orthogonal functional group" refers to groups that function with endogenous components of a cell with reduced efficiency as compared to a corresponding molecule that is endogenous to the cell, or that fails to function with endogenous components of the cell. For example, in the context of tRNAs and aminoacyl-tRNA synthetases (RS), orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to the ability of an endogenous tRNA to function with the endogenous tRNA synthetase; or of an orthogonal aminoacyl-tRNA synthetase to function with an endogenous tRNA compared to the ability of an endogenous tRNA synthetase to function with the endogenous tRNA. The orthogonal molecule lacks a functional endogenous complementary molecule in the cell. For example, an orthogonal tRNA in a cell is aminoacylated by any endogenous RS of the cell with reduced or even undetectable efficiency, when compared to aminoacylation of an endogenous tRNA by the endogenous RS. In another example, an orthogonal RS aminoacylates any endogenous tRNA a cell of interest with reduced or even undetectable efficiency, as compared to aminoacylation of the endogenous tRNA by an endogenous RS. A second orthogonal molecule can be introduced into the cell that function with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) to that of a control, e.g., a corresponding tRNA/RS endogenous pair, or an active orthogonal pair (e.g., a tyrosyl orthogonal tRNA/RS pair).

As used herein, the term "Pyrrolysine-tRNA synthetase (PylRS)" refers to an enzyme that is able to attach pyrrolysine or pyrrolysine analogs to a corresponding tRNA molecule. In the case of pyrrolysine the corresponding tRNA (tRNA$_{CUA}$) molecule comprises an anticodon domain that binds to an amber codon. PylRS and tRNA$_{CUA}$ together form a tRNA/RS pair.

As used herein term "pyrrolysine (Pyl)" and "Pyl analog" refers to an amino acid derivative recognized by either wild type or genetically evolved PylRS and incorporated into proteins at an amber codon in an mRNA molecule.

The term "amber codon," as used herein, refers to incorporation sites of pyrrolysine and pyrrolysine analogues. Amber codons correspond to the nucleotide triplet within messenger RNA encoding Uracil, Adenine and Guanine (UAG) and/or the corresponding DNA encoded sequence Thymine, adenine and guanine (TAG) which is transcribed to UAG in RNA. The TAG/UAG codon are used interchangeably herein to refer to the incorporation site of pyrrolysine and pyrrolysine analogues.

As used herein, the term "protecting group" refers to a temporary chemical group added to a molecule or portion thereof to prevent a molecule or portion thereof from reacting (i.e., it assists with chemoselectivity and/or biorthogonality). The term "deprotecting" as used herein refers to removal of a protecting group and may be used interchangeably with the term "decaging".

As used herein, the term "physiological conditions" refers to and encompasses those conditions compatible with living cells, e.g., predominantly aqueous conditions of a temperature, pH, salinity, etc. that are compatible with living cells.

As used herein, the terms "chimeric protein" and "fusion protein" are used interchangeably and refer to a polypeptide comprising at least two amino acid sequences not generally found together in a single polypeptide in nature. For example, a chimeric protein may comprise a first amino acid sequence derived from a first source, covalently bonded to a second amino acid sequence derived from a second source, in which the first and second source are not identical or, in other words, characterize two different biological entities.

The term "imaging moiety" refers to a molecule, compound, or fragment thereof that facilitates a technique and/or process used to create images or take measurements of a cell, tissue, and/or organism (or parts or functions thereof) for clinical and/or research purposes. An imaging moiety can produce, for example, a signal through emission and/or interaction with electromagnetic, nuclear, and/or mechanical (e.g., acoustic as in ultrasound) energy. An imaging moiety can be used, for example, in various radiology, nuclear medicine, endoscopy, thermography, photography, spectroscopy, and microscopy methods.

The term "therapeutic moiety" refers to a molecule, compound, or fragment thereof that is used for the treatment of a disease or for improving the well-being of an organism or that otherwise exhibit healing properties (e.g., pharmaceuticals, drugs, peptides and the like). A therapeutic moiety can be a chemical, or fragment thereof, of natural or synthetic origin used for its specific action against a disease or condition.

The term "cytotoxic moiety" refers to a molecule, compound, or fragment thereof that has a toxic or poisonous effect on cells, or that kills cells. The term is intended to include radioactive isotopes, chemotherapeutic agents, and toxins such as small molecule toxins or enzymatically active toxins of bacterial, fungal, plant or animal origin, including fragments and/or variants thereof. Treating cells with a cytotoxic moiety can produce a variety of results. Cells may undergo necrosis, stop actively growing and dividing, or activate a genetic program of controlled cell death (i.e., apoptosis). Examples of cytotoxic moieties include, but are not limited to, SN-38, bendamustine, VDA, doxorubicin, pemetrexed, vorinostat, lenalidomide, irinotecan, ganetespib, docetaxel, 17-AAG, 5-FU, abiraterone, crizotinib, KW-2189, BUMB2, DC1, CC-1065, adozelesin, or fragment(s) thereof.

As used herein, a "binding moiety" refers to a substance (e.g., a ligand) that can form a complex with a biomolecule. The ligand and/or formation of the ligand-biomolecule complex can have a biological or chemical effect, such as a therapeutic effect, cytotoxic effect, and/or imaging effect.

As used herein the term "post-translational modification" refers to one or more modifications to a polypeptide that occur typically within a cell, either co-translationally or after the polypeptide has been fully translated. Post-translational modifications can be naturally occurring in vivo, and in many instances, are required in order for a native polypeptide to be biologically active. A wide variety of posttranslational modifications are known to exist in vivo, including, e.g., glycosylation and/or phosphorylation, and are typically regulated by endogenous cellular components such as cellular proteins. A polypeptide can be subject to multiple types of posttranslational modifications and the modifications can be anywhere within the polypeptide molecule.

As used herein, the term "genetically-encodable" used in reference to an amino acid sequence of a polypeptide, peptide or protein refers to an amino acid sequence composed of amino acid residues that are capable of production by transcription and translation of a nucleic acid encoding the amino acid sequence, where transcription and/or translation may occur in a cell or in a cell-free transcription/translation system using native and/or non-native transcription/translation machinery and processes.

The terms "antibody" and "immunoglobulin" are used interchangeably herein in the broadest sense and includes monoclonal antibodies (including full length or intact monoclonal antibodies), polyclonal antibodies, multivalent antibodies, multispecific antibodies (e.g., bispecific antibodies), and antibody fragments (see below) so long as they exhibit the desired biological activity.

As used herein, the term "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the invention may be made by the hybridoma method first described by Kohler et al., Nature 256:495 (1975), or may be made by recombinant DNA methods (see, e.g., U.S. Pat. No. 4,816,567). "Monoclonal antibodies" may also be isolated from phage antibody libraries using the techniques described in e.g. Clackson et al, Nature 352:624-628 (1991) or Marks et al, J. Mol. Biol. 222:581-597 (1991).

The monoclonal antibodies defined herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 341, 544-546 (1989)) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g. single chain Fv; scFv) (Bird et al, Science 242:423-426 (1988); and Huston et al., PNAS (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097 and WO 93/11161; (xi) "linear antibodies" comprising a pair of tandem Fd segments (VH-CH1-VH-CH1) which, together with complementary light chain polypeptides, form a pair of antigen binding regions (Zapata et al. Protein Eng. 8 (10): 1057-1062 (1995); and U.S. Pat. No. 5,641,870).

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

As used herein, "antibody variable domain" refers to the portions of the light and heavy chains of antibody molecules that include amino acid sequences of Complementarity Determining Regions (CDRs); ie., CDR1, CDR2, and CDR3, and Framework Regions (FRs). VH refers to the variable domain of the heavy chain. VL refers to the variable domain of the light chain. According to the methods used in this invention, the amino acid positions assigned to CDRs and FRs as well as antibodies and antigen binding fragments may be defined according to Kabat (Sequences of Proteins of Immunological Interest (National Institutes of Health, Bethesda, Md., 1987 and 1991)).

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, MD. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop. For example, the CDRH1 of the heavy chain of antibody 4D5 includes amino acids 26 to 35.

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

The "Fab" fragment contains a variable and constant domain of the light chain and a variable domain and the first constant domain (CHI) of the heavy chain. F(ab')2 antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the VH and VL domains of antibody, wherein these domains are present in a single polypeptide chain. Generally, the Fv polypeptide further comprises a polypeptide linker between the VH and VL domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994).

"Humanized" forms of non-human (e.g., murine) antibodies are chimeric antibodies which contain minimal sequence derived from non-human immunoglobulin. Typically, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al, Nature 332:323-329 (1988); and Presta, Curr. Op. Struct. Biol. 2:593-596 (1992).

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, EP 404,097 and WO 93/11161.

As used herein, the terms "substrate surface" and "support surface" refers to a matrix of material in a substantially fixed arrangement that can be functionalized to allow synthesis, attachment or immobilization of polypeptides, either directly or indirectly. The term "solid support" encompasses terms such as "resin" or "solid phase." A solid support may be composed of polymers, e.g., organic polymers such as polystyrene, polyethylene, polypropylene, polyfluoroethylene, polyethyleneoxy, and polyacrylamide, as well as copolymers and grafts thereof. A solid support may also be inorganic, such as glass, silica, silicon, controlled-pore-glass (CPG), reverse-phase silica, or any suitable metal. In addition, the term "solid support" may include any solid support that has received any type of coating or any other type of secondary treatment, e.g., Langmuir-Blodgett films, self-assembled monolayers (SAM), so-gel, or the like. Certain embodiments described herein may be used to functionalise a support surface with one or more polypeptides.

As used herein, the terms "cancer" and "cancerous" refer to or describe the physiological condition in mammals that is typically characterized by unregulated cell growth. Included in this definition are benign and malignant cancers as well as dormant tumors or micrometastatses. The term cancer includes solid tumors and hematologic cancers. Examples of cancer include but are not limited to, carcinoma, lymphoma, blastoma, sarcoma, and leukaemia.

Polypeptides

As used herein, the term "modified polypeptide" may refer to any one of the first, second or third polypeptides modified by one or more of the methods of the aspects of the present invention as appropriate.

As will be appreciated from the present disclosure, the applications of modified polypeptides of embodiments of the present invention are numerous and can provide a number of advantages. For example, the β-hydroxy aldehyde moiety and/or α-oxoaldehyde moiety are smaller than most if not all conventional peptide tags that allow for covalent modification of proteins, thereby requiring minimal changes to the amino acid sequence of a target polypeptide. Second, the β-hydroxy aldehyde moiety and/or α-oxoaldehyde moiety can take advantage of well-characterized secondary labelling chemistries. Third, the methods used for forming modified polypeptides as described herein demonstrate reversibility, allowing for sequential modification and replacement of a moiety attached to modified polypeptides as described herein. Further, because the β-hydroxy aldehyde moiety and/or α-oxoaldehyde moiety are formed using biorthogonal machinery and/or methods and are independent of the nature of the modified polypeptide or location of placement within the parent amino acid sequence, the 1-hydroxy aldehyde moiety and/or α-oxoaldehyde moiety can be used to facilitate modification of a large number of polypeptides using readily available expression systems.

A wide variety of polypeptides may be modified according to certain methods of the present invention. Polypeptides suitable for modification according to certain embodiments of the present invention include both proteins having a naturally-occurring amino acid sequence and fragments thereof, and non-naturally occurring polypeptides and fragments thereof.

The following are exemplary classes and types of polypeptides which are of interest for modification using certain embodiments of the methods described herein.

In certain embodiments, the methods of the present invention are applied to modification of polypeptides that may provide for a therapeutic benefit, particularly those polypeptides for which attachment to a moiety can provide for one or more of, for example, an increase in serum half-life, a decrease in adverse side-effects (such as an adverse immune response), additional or alternate biological activity or functionality, targeting of specific cells, tissues, organs or organisms, and the like. Where the therapeutic polypeptide is an antigen for a vaccine, modification can provide for an enhanced immunogenicity of the polypeptide.

Examples of classes of therapeutic proteins include those that are cytokines, chemokines, growth factors, hormones, antibodies, and antigens. Further examples include erythropoietin (EPO, e.g., native EPO, synthetic EPO (see, e.g., US 2003/0191291), human growth hormone (hGH), bovine growth hormone (bGH), follicle stimulating hormone (FSH), interferons (e.g., IFN-gamma, IFN-beta, IFN-alpha, IFN-omega, consensus interferon, and the like), insulin, insulin-like growth factors (e.g., IGF-I, IGF-II), blood factors (e.g., Factor VIII, Factor IX, Factor X, tissue plasminogen activator (TPA), and the like), colony stimulating factors (e.g., granulocyte-CSF (G-CSF), macrophage-CSF (M-CSF), granulocyte-macrophage-CSF (GM-CSF), and the like), transforming growth factors (e.g., TGF-beta, TGF-alpha), interleukins (e.g., IL-1, IL-2, IL-3, IL-4, IL-5, IL-6, IL-7, IL-8, IL-12, and the like), epidermal growth factor (EGF), platelet-derived growth factor (PDGF), fibroblast growth factors (FGFs, e.g., aFGF, bFGF), glial cell line-derived growth factor (GDNF), nerve growth factor (NGF), RANTES, and the like, angiogenic agents (e.g., vascular endothelial growth factor (VEGF)); anti-angiogenic agents (e.g., soluble VEGF receptor); protein vaccines; oxygen transport proteins (e.g. globin proteins such as myoglobin, haemoglobin and the like); and neuroactive peptides (such as bradykinin, cholecystokinin, gastin, secretin, oxytocin, gonadotropin-releasing hormone, beta-endorphin, enkephalin, substance P, somatostatin, galanin, growth hormone-releasing hormone, bombesin, warfarin, dynorphin, neurotensin, inotilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc).

Further examples include antibodies, e.g., polyclonal antibodies, monoclonal antibodies, humanized antibodies, antigen-binding fragments (e.g., F(ab)', Fab, Fv), single chain antibodies, diabodies, bispecific and the like. For example, antibodies that specifically bind to a tumour antigen, an immune cell antigen (e.g., CD4, CD8, and the like), an antigen of a microorganism, particularly a pathogenic microorganism (e.g., a bacterial, viral, fungal, or parasitic antigen) and interferons.

In certain embodiments, the modified polypeptides are fusion polypeptides. Suitable fusion proteins include, but are not limited to, antibody fusion proteins such as Fc-fusion proteins. The term "Fc-fusion protein", as used herein, refers to proteins, such as therapeutic proteins, comprising an immunoglobulin-derived moiety, and a moiety derived from a second, non-immunoglobulin protein. The use of Fc-fusion proteins may prolong the plasma half-life of the protein of interest, which for therapeutic peptides, results in an improved therapeutic efficacy In certain embodiments, the Fc-fusion protein comprises a receptor or fragment thereof, e.g. a transmembrane receptor. In certain embodiments, the Fc-fusion protein comprises an extracellular domain of a receptor, or a ligand binding fragment of the extracellular part or domain of a given receptor. Examples for therapeutically interesting receptors that may be used include, but are not limited to, CD2, CD3, CD4, CD8, CD11a, CD11b, CD14, CD18, CD20, CD22, CD23, CD25, CD33, CD40, CD44, CD52, CD80, CD86, CD147, CD164, IL-2 receptor, IL-4 receptor, IL-6 receptor, IL-12 receptor, IL-17 receptors (IL-17R, IL-17RB (IL-17RH1), IL-17RC (IL-17RL), IL-17RD (hSEF) or IL-17RE), IL-18 receptor subunits (IL-18R-alpha, IL-18R-beta), EGF receptor, VEGF receptor, integrin alpha-4 10 beta 7, the integrin VLA4, B2 integrins, TRAIL receptors 1, 2, 3, and 4, RANK, RANK ligand, epithelial cell adhesion molecule (EpCAM), intercellular adhesion molecule-3 (ICAM-3), CTLA4 (which is a cytotoxic T lymphocyte-associated antigen), Fc-gamma-I, II or III receptor, HLA-DR 10 beta, HLA-DR antigen, L-selectin.

Non-limiting examples of therapeutic Fc-fusion proteins include Etanercept (Enbrel), Alefacept (Amevive@), Abatacept (Orencia@), Rilonacept (Arcalyst®), Romiplostim (Nplate®), Belatacept (Nulojix®) and Aflibercept (Eylea™).

Certain embodiments of the present invention may also find use in production of components of immunogenic compositions (e.g., therapeutic vaccines). For example, certain embodiments of the present invention can be used to facilitate attachment of moieties that increase serum half-life of a polypeptide antigen, that increase immunogenicity of a polypeptide, or that link a non-amino acid antigen to a polypeptide carrier. In this regard, certain embodiments of the present invention can be used to facilitate modification of microbial antigens (e.g., a bacterial, viral, fungal, or parasitic antigen), tumour antigens, and other antigens which are of interest for administration to a subject to elicit an immune response in the subject.

Accordingly, certain embodiments of the present invention may be for use in the production of antibodies such as multivalent antibodies, bispecific antibodies, as well as production of fusion proteins such as Fc-fusion proteins as described herein as well.

In certain embodiments, the modified polypeptide is a substrate for one or more proteases. Conjugates comprising polypeptides that are substrates for proteases may be used to provide conjugated groups that can be liberated or fragmented from the conjugate by the action of a protease. In embodiments, wherein the conjugated functional group comprises a therapeutic moiety, the therapeutic moiety may be released to a target location.

Further exemplary polypeptides of interest for modification using certain methods of the present invention are those that are of interest for detection or functional monitoring in an assay (e.g., as a research tool, in a drug screening assay, and the like). Exemplary polypeptides of this type include receptors (e.g., G-protein coupled receptors (GPCRs, including orphan GPCRs)), receptor ligands (including naturally-occurring and synthetic), protein channels (e.g., ion channels (e.g., potassium channels, calcium channels, sodium channels, and the like), and other polypeptides.

Functional Moieties & Uses

Functional moieties as described herein may refer to any one of the first, second, third or further functional moieties of certain embodiments of the present invention.

The functional moieties described herein may be conjugated to any one of the first, second, third or further polypeptides of certain embodiments of the present invention where appropriate.

As such it will be understood that the aldehyde donor molecules and/or substituted hydroxylamine donor molecule may comprise any of the functional moieties described herein.

In certain embodiments, the aldehyde donor molecule comprises one or more functional moieties as described herein.

In certain embodiments, the hydroxylamine donor molecule i.e. the substituted hydroxylamine molecule, comprises one or more functional moieties as described herein.

Conjugates formed by conjugation via the β-hydroxy aldehyde moiety and/or α-oxoaldehyde moiety of certain embodiments of the present invention can be used for a variety of applications including, but not limited to, visualization using fluorescence or epitope labelling (e.g., electron microscopy using gold particles equipped with aldehyde reactive groups), protein immobilization (e.g., protein microarray production), protein dynamics and localization studies and applications, and conjugation of polypeptides with a functional moiety of interest (e.g., moieties that improve a parent protein's therapeutic index (e.g., PEG), targeting moieties (e.g., to enhance bioavailability to a site of action), and biologically active moieties (e.g., a therapeutic moiety).

In general, the functional moiety or moieties that may be conjugated to certain modified polypeptides as described herein, can provide for one or more of a wide variety of functions or features.

Non-limiting examples of functional moieties that may be conjugated to certain modified polypeptides as described herein include detectable moieties ((e.g., dye moieties (e.g., chromophores, fluorophores); biophysical probes (spin labels, nuclear magnetic resonance (NMR) probes); Förster Resonance Energy Transfer (FRET)-type moieties (e.g., at least one member of a FRET pair, including at least one member of a fluorophore/quencher pair); Bioluminescence Resonance Energy Transfer (BRET)-moieties (e.g., at least one member of a BRET pair)); immunodetectable tag moieties (e.g., FLAG, His(6), and the like), localization tag moieties (e.g., to identify association of a tagged polypeptide at the tissue or molecular cell level (e.g., association with a tissue type, or particular cell membrane)), and the like); light-activated dynamic moieties (e.g., azobenzene mediated pore closing, azobenzene mediated structural changes, photodecaging recognition motifs); polymeric moieties (e.g., poly(ethylene glycol)); purification moieties (e.g., to facilitate isolation by affinity chromatography (e.g., attachment of a FLAG epitope); membrane localization moieties (e.g., polysaccharides, lipids or glycophosphatidylinositol (GPI)-type anchors); immobilization moieties (e.g., to facilitate attachment of the polypeptide to a surface, including selective attachment); therapeutic moieties (e.g., to facilitate drug targeting, e.g., through attachment of a drug to an antibody); targeted delivery moieties, (e.g., ligands for binding to a target receptor (e.g., to facilitate viral attachment, attachment of a targeting protein present on a liposome, etc.)); conjugation moieties (e.g., azide moieties) and the like.

Specific, non-limiting examples are provided below.

Detectable Moieties

In certain embodiments, the functional moiety comprises one or more detectable moieties.

In certain embodiments, the detectable moiety comprises a fluorescent moiety, specific examples of fluorescent moieties given herein are illustrative and are not meant to limit the fluorescent moieties for use with certain embodiments of the modified polypeptides described herein.

In certain embodiments, the fluorescent moiety is a fluorescent dye. Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes.

In certain embodiments, the fluorescent moiety comprises a fluorescent peptide or protein. Examples of fluorescent peptides and proteins include GFP (Green Fluorescent Protein) or derivatives of GFP (e.g., sfGFP, EBFP, EBFP2, Azurite, mKalamal, ECFP, Cerulean, CyPet, YFP, Citrine, Venus, YPet).

Detectable moieties may be detected by any suitable method. For example, a fluorescent moiety may be detected by exciting the fluorochrome with the appropriate wavelength of light and detecting the resulting fluorescence, e.g., by microscopy, visual inspection, via photographic film, by the use of electronic detectors such as charge coupled devices (CCDs), photomultipliers and the like.

In certain embodiments, the functional moiety comprises one or more imaging moieties as defined herein.

In certain embodiments, the detectable moiety comprises a positron-emitting isotope (e.g., 18F) for use in positron emission tomography (PET). In certain embodiments, the detectable moiety comprises a gamma-ray isotope (e.g., 99mTc) for use in single photon emission computed tomography (SPECT). In certain embodiments, the detectable moiety comprises a paramagnetic molecule or nanoparticle (e.g., Gd3+ chelate or coated magnetite nanoparticle) for use in magnetic resonance imaging (MRI).

In certain embodiments, the detectable moiety comprises one or more of: a gadolinium chelate, an iron oxide particle, a super paramagnetic iron oxide particle, an ultra-small paramagnetic particle, a manganese chelate or gallium containing agent.

Examples of gadolinium chelates include, but are not limited to diethylene triamine pentaacetic acid (DTPA), 1,4,7,10-tetraazacyclododecane-1,4,7,10-tetraacetic acid (DOTA), and 1,4,7-triazacyclononane-N,N',N"-triacetic acid (NOTA).

In certain embodiments, the detectable moiety comprises a near-infrared fluorophore for use in near-infra red (near-IR) imaging. In certain embodiments, the detectable moiety comprises a luciferase (firefly, bacterial, or coelenterate) or other luminescent molecule for use in bioluminescence imaging. In certain embodiments, the detectable moiety comprises perfluorocarbon-filled vesicle for use in ultrasound methods.

Certain embodiments of the present invention may be for use in methods of diagnosis of a disease or disorder.

Detectable moieties also include peptides or polypeptides that can be detected by antibody binding, e.g., by binding of a detectably labelled antibody or by detection of bound antibody through a sandwich-type assay e.g. an enzyme linked immunosorbent assay (ELISA).

Conjugation Moieties

In certain embodiments, the functional moiety comprises one or more conjugation moieties.

Conjugation moieties include, but are not limited to, alkenes, alkynes, azides, aryl halides, hydrazones, oximes, other Schiff bases, and the products of any of the various click reactions. Exemplary hydrazino, oxyamino, and carbonyl conjugating reagents for use in forming the high-efficiency conjugation moieties are illustrated in U.S. Pat. No. 7,102,024 and can be adapted for use in the certain embodiments of the methods described herein.

Polymeric Moieties

In certain embodiments, the functional moiety comprises one or more polymeric moieties.

Aptly attachment of certain polymeric moieties (e.g., Polyethylene glycol (PEG)) to a modified polypeptide as describe therein, for example a pharmaceutically active (therapeutic) polypeptide can be desirable as such conjugation can increase therapeutic index by increasing serum half-life as a result of increased proteolytic stability and/or decreased renal clearance. Additionally, attachment of one or more polymers (e.g., PEGylation) can reduce immunogenicity of protein pharmaceuticals.

In one embodiment, the polymeric moiety is a water-soluble polymer. Aptly, the polymeric moiety is water-soluble, non-toxic, and pharmaceutically inert.

Polymeric moieties that may be attached to certain embodiments of the present invention can have a wide range of molecular weights, and polymer subunits. These subunits may include a biological polymer (e.g. polysaccharides, lipids, fatty acids, and the like), a synthetic polymer, or a combination thereof.

Examples of such polymers include but are not limited to, dextran and dextran derivatives, including dextran sulfate, P-amino cross linked dextrin, and carboxymethyl dextrin, cellulose and cellulose derivatives, including methylcellulose and carboxymethyl cellulose, starch and dextrines, and derivatives and hydroylactes of starch, polyalklyene glycol and derivatives thereof, including polyethylene glycol, methoxypolyethylene glycol, polyethylene glycol homopolymers, polypropylene glycol homopolymers, copolymers of ethylene glycol with propylene glycol, wherein said homopolymers and copolymers are unsubstituted or substituted at one end with an alkyl group, heparin and fragments of heparin, polyvinyl alcohol and polyvinyl ethyl ethers, polyvinylpyrrolidone, aspartamide, and polyoxyethylated polyols, with the dextran and dextran derivatives, dextrine and dextrine derivatives. It will be appreciated that various derivatives of the specifically recited polymers are also contemplated.

The polymeric moiety, may have any molecular weight, for example, a molecular weight of 500-60,000 Da, for example 500-10,000 Da, 1000-5000 Da, 10,000-20,000 Da, or 20,000-60,000 Da.

Aptly, the water-soluble polymeric moiety is a polyethylene glycol and in some embodiments, the modified polypeptide is "pegylated". As used herein, the terms "pegylated" and "pegylation" have their general meaning in the art and refer generally, for example, to the process of chemically modifying a polypeptide as described herein by covalent attachment of one or more molecules of polyethylene glycol or a derivative thereof.

Although "pegylation" is often carried out using polyethylene glycol or derivatives thereof, such as methoxy polyethylene glycol, the term as used herein also includes any other useful polyalkylene glycol, such as, for example polypropylene glycol. As used herein, the term "PEG" refers to polyethylene glycol and its derivatives as understood in the art (see for example U.S. Pat. Nos. 5,445,090, 5,900,461, 5,932,462, 6,436,386, 6,448,369, 6,437,025, 6,448,369, 6,495,659, 6,515,100, and 6,514,491).

The polymer used for pegylation can be of any molecular weight, and can be branched or unbranched. Aptly, the polyethylene glycol has a molecular weight between about 1000 Daltons and about 100,000 Da (the term "about" indicating that in preparations of polyethylene glycol, some molecules will weigh more, some less, than the stated molecular weight). For example, the polyethylene glycol can have an average molecular weight of about 1000, 5000, 10000, 15000, 20000, 25000, 30000, 35000, 40000, 50000, 60000, 70000, 80000, 90000 or 100000 Da.

In certain embodiments, the polymeric moiety comprises one or more spacers and/or linkers. Exemplary spacers and/or linkers include linear or branched moieties comprising one or more repeat units employed in a water-soluble polymer, diamino and/or diacid units, natural or unnatural amino acids or derivatives thereof, as well as aliphatic moieties, including alkyl, aryl, heteroalkyl, heteroaryl, alkoxy, and the like, which can contain, for example, up to 18 carbon atoms or even an additional polymer chain.

In certain embodiments, the polymeric moiety, or one or more of the spacers or linkers of the polymeric moiety when present, may include polymer chains or units that are biostable or biodegradable. For example, polymers with repeat linkages have varying degrees of stability under physiological conditions depending on bond lability. Polymers with such bonds can be categorized by their relative rates of hydrolysis under physiological conditions based on known hydrolysis rates of low molecular weight analogs, e.g., from less stable to more stable, e.g., polyurethanes, polyorthoesters, polyamides.

Synthetic Analogues

In certain embodiments, methods of the present invention may be used for the production of synthetic analogues of naturally occurring proteins that comprise post-translational modifications (PTM). For example, functional moieties may comprise naturally occurring polymers such as glycolipids, polysaccharides, lipids or fatty acids that may be conjugated to a protein of interest in order to mimic post translational modifications that may be present on a protein produced in vivo or via enzymatic methods. Such synthetic analogues may for use in therapeutic applications such as the treatment of a disease or condition. In certain embodiments, such synthetic analogues may be for use in research purposes. For example, in order to provide information on properties of proteins that are post-translationally modified in vivo but are not possible to reproduce using recombinant or enzymatic techniques.

In certain embodiments, methods of the present invention may be used to replicate one or more forms of posttranslational modification which include but are not limited to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, myristoylation, oxidation, proteolytic processing, phosphorylation, prenylation, racemization, selenoylation, sulfation, transfer-RNA mediated addition of amino acids to proteins such as arginylation, and ubiquitination.

Binding Moieties

In certain embodiments, the functional moiety comprises one or more binding moieties.

In certain embodiments, the functional moiety comprises one of a pair of binding partners (e.g., a ligand, a ligand-binding portion of a receptor, a receptor-binding portion of a ligand, etc.). For example, the functional moiety may comprise a polypeptide that serves as a viral receptor and, upon binding with a viral envelope protein or viral capsid protein, facilitates attachment of virus to a surface (e.g., cell surface, substrate surface etc.) on which the modified polypeptide is located. Alternatively, the functional moiety comprises an antigen that is specifically bound by an antibody (e.g., monoclonal antibody), to facilitate detection and/or separation of the modified polypeptide.

In certain embodiments, the binding moiety is a targeting moiety.

Embodiments comprising targeting moieties may be used to target modified polypeptides (e.g. therapeutic polypeptides or florescent polypeptides) to specific organs, tissues, cells and/or components of a cell. For example, in certain embodiments the targeting moiety comprises a folate moiety. Folate moieties include any molecules that are ligands for the folate receptor such as folate or derivatives thereof. As the folate receptor has a high affinity for folate and folate derivatives, and is often expressed on cancerous cells, certain embodiments of the present invention provide methods of targeting cancerous cells. Furthermore, certain embodiments provide methods of targeting peptide drugs to cancerous cells.

In certain embodiments, the targeting moiety comprises an antibody or a fragment thereof as described herein. For example, the targeting moiety may comprise a Fc-fragment, therefore forming an Fc-fusion protein.

Fusion Proteins (Protein Moieties)

In certain embodiments, the functional moiety comprises one or more further polypeptides. Therefore, certain embodiments of the present invention provide methods for the production of fusion proteins.

In certain embodiments, the functional moiety comprises a modified polypeptide as described herein.

The use of a β-hydroxy aldehyde moiety and/or α-oxoaldehyde as a method of linking two polypeptides may have a number of advantages over prior methods utilising peptide linker molecules. For example, β-hydroxy aldehyde moieties and/or α-oxoaldehyde moieties require minimal changes to the amino acid sequence of a polypeptide. The certain embodiments of the methods of the present invention also provide β-hydroxy aldehyde moiety and/or α-oxoaldehyde at a selected location allowing for one or more proteins to be conjugated via any residue in the amino acid chain of a polypeptide. This may allow for a greater range of orientations of the polypeptides in a fusion protein.

In certain embodiments, the functional moiety comprises an antibody or fragment thereof as described herein. Thus, certain embodiments of the present invention may be for producing humanized antibodies, multivalent antibodies, bispecific antibodies or any other immunoglobin fusion proteins.

In certain embodiments, the functional moiety comprises a Fc-fragment of an antibody and the methods of the present invention are for producing a Fc-fusion protein as described herein.

Therapeutic Moieties

In certain embodiments, the functional moiety comprises one or more therapeutic moieties. In certain embodiments, the therapeutic moiety comprises a drug moiety.

As used herein term "drug" refers to any active agent that affects any biological process. Active agents that are considered drugs for uses in certain embodiments of the present invention are agents that exhibit a pharmacological activity. Examples of drugs include active agents that are used in the prevention, diagnosis, alleviation, treatment or cure of a disease, disorder or condition. For example, drugs include, but are not limited, small molecule drugs, peptide drugs, chemotherapeutic agents, radiotherapy agents and the like.

As used herein the term "small molecule drug" refers to a compound, e.g., an organic compound, which exhibits a pharmaceutical activity of interest and which is generally of a molecular weight of no greater than about 800 Da, or no greater than 2000 Da, but can encompass molecules of up to 5 kDa and can be as large as about 10 kDa. A small inorganic molecule refers to a molecule containing no carbon atoms, while a small organic molecule refers to a compound containing at least one carbon atom.

As used herein the term "peptide drug" refers to amino-acid containing polymeric compounds, and encompasses naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight. Examples of peptide drugs include, but are not limited to, daptomycin, nesiritide, cetrorelix acetate and a combination thereof as well proteins or fragments thereof such as hormones, enzymes and/or antibodies that are naturally occurring, recombinant or chemically synthesized.

Therapeutic moieties that may be conjugated to modified polypeptides as described herein include but are not limited to cytotoxic moieties, chemotherapeutic agents, biologic agents, growth inhibitory agents, nanoparticle agents, agents used in radiation therapy, agents used in photodynamic therapy, agents used in hyperthermia therapy (e.g., radiofrequency ablation), anti-angiogenesis agents, apoptotic agents, anti-tubulin agents, siRNA agents, enzyme/pro-drug agents, nucleic acid agents, oligopeptide agents, anti-HER-2 antibodies, anti-CD20 antibodies, an epidermal growth factor receptor (EGFR) antagonist (e.g., a tyrosine kinase inhibitor), HER1/EGFR inhibitors (e.g., erlotinib (Tarceva®), platelet derived growth factor inhibitors (e.g., Gleeved® (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, or combination thereof.

As used herein, the term "biologic agent" is a generic term referring to any biological molecules derived from protein, carbohydrate, lipid or nucleic acid and is useful in the treatment of a disease or disorder. A non-exhaustive list of biologic agents include: TNF blockers (e.g., etanercept, infliximab, adalimumab, certolizumab pegol, and golimumab); interleukin 1 (IL-1) blockers such as anakinra; monoclonal antibodies (e.g., Trastuzumab (Herceptin), Bevacizumab (Avastin), Cetuximab (Erbitux), Panitumumab (Vectibix), Ipilimumab (Yervoy), Rituximab (Rituxan and Mabthera), Alemtuzumab (Campath), Ofatumumab (Arzerra), Gemtuzumab ozogamicin (Mylotarg), Brentuximab vedotin (Adcetris), 90Y-lbritumomab Tiuxetan (Zevalin) and 131I-Tositumomab (Bexxar)); T-cell co-stimulation blockers such as abatacept; Interleukin 6 (IL-6) blockers such as tocilizumab and antibodies against oxidized phospholipids and/or oxidized lipoproteins and/or fragments or derivatives thereof.

In certain embodiments, wherein the modified polypeptide is an antibody or fragment thereof as described herein, certain embodiments of the present invention provide a method for producing an antibody drug conjugate (ADC).

As used herein the term "antibody-drug-conjugate" or "ADC" refers to a binding protein, such as an antibody or antigen binding fragment thereof, chemically linked to one or more drug(s) that may optionally be therapeutic or cytotoxic moieties. Non-limiting examples of drugs that may be included in ADCs are mitotic inhibitors, antitumor antibiotics, immunomodulating agents, vectors for gene therapy, alkylating agents, antiangiogenic agents, antimetabolites, metabolic modulators, boron-containing agents, hormones, antihormone agents, corticosteroids, photoactive therapeutic agents, oligonucleotides, radionuclide agents, topoisomerase inhibitors, tyrosine kinase inhibitors, neurologically active compounds and radiosensitizers.

ADCs generally comprise antibodies or fragments thereof that target antigens that are overexpressed in disease cells (such as cancer cells) or antigens overexpressed in tissue associated with disease cells. For example, target antigens of cancer cells include but are not limited to, transmembrane glycoprotein NMB (GPNMB), CD56, Tumor Associated Calcium Signal Transducer 2 (TACSTD2), Carcinoembryonic antigen-related cell adhesion molecule (CEACAM5), Folate receptor-α, Mucin 1, Nectin 4, ectonucleotide pyrophosphatase/phosphodiesterase 3 (ENPP3), Guanylyl cyclase C (GCC), Solute Carrier Family 44 Member 4 (SLC44A4), Sodium-dependent phosphate transport protein 2B (NaPi2b), CD70, Carbonic anhydrase 9 (CA9), Trophoblast glycoprotein (TPBG), tissue factor, Zinc transporter LIV-1 (ZIP6), P-Cadherin, Fibronectin Extra-domain B, Endothelin receptor ETB, VEGFR2 (CD309), Tenascin c, Collagen IV, Periostin, HER 2, EGFR, CD30, CD22, CD79b, CD19, CD138, CD74, CD37, CD33, CD19 and CD98.

Examples of ADCs include but are not limited to trastuzumab emtansine (sold under the trade name Kadcyla) and brentuximab vedotin (sold under the trade name Adcetris) and see for example, Diamantis, Nikolaos, and Udai Banerji. British journal of cancer 114.4 (2016): 362.

In certain embodiments, the drug moiety comprises one or more anti-cancer agents. Anti-cancer agents that may be suitable for use in certain embodiments of the present invention, include non-peptidic (i.e., non-proteinaceous) compounds that reduce proliferation of cancer cells, and encompass cytotoxic agents and cytostatic agents.

Further examples can be found in US patent publications US20140134265A1 and US20120183566A1 which are incorporated herein by reference.

Methods of Treatment

Modified proteins as described herein and certain embodiments of conjugates thereof may be for use as a medicament.

In certain embodiments, the modified polypeptides as described herein and certain embodiments of the conjugates thereof may be for use in the treatment of a number of diseases or disorders due to the wide range of polypeptides that may be modified using the methods described herein and the wide range of functional moieties that may be conjugated to said modified polypeptides.

Examples of diseases that may be treated by the modified polypeptides as described herein and certain embodiments of the conjugates thereof include, but are not limited to: cancer as defined herein; autoimmune diseases (e.g., rheumatoid arthritis, multiple sclerosis, immune-mediated or Type I diabetes mellitus, inflammatory bowel disease (e.g., Crohn's disease or ulcerative colitis), systemic lupus erythematosus, psoriasis, scleroderma, autoimmune haemolytic anaemia, Addison's disease, nephritis and the like); inflammatory diseases (e.g., Alzheimer's disease, Ankylosing spondylitis, arthritis, asthma, atherosclerosis, Crohn's disease, colitis, cystic fibrosis, cardiovascular disease, sepsis and the like); neurological disorders (e.g., multiple sclerosis, Parkinson's disease, Huntington's disease, Alzheimer's disease, amyotrophic lateral sclerosis, motor neuron disease and the like); metabolic disorders (e.g., diabetes, hyperlipidaemia, insulin resistance and the like); liver diseases; renal diseases; and infectious diseases.

In certain embodiments, the modified polypeptides as described herein and certain embodiments of the conjugates thereof are for use in the treatment of cancer.

The modified polypeptides of the present disclosure and certain embodiments of the conjugates thereof may be formulated as pharmaceutical compositions prepared for storage or administration for use in the treatment and/or prevention of diseases or conditions as described herein. Such a composition typically comprises a therapeutically effective amount of a modified polypeptide described herein or conjugate thereof, in the appropriate form, in a pharmaceutically acceptable carrier.

The therapeutically effective amount of modified polypeptide described herein or conjugate thereof will depend on the route of administration, the type of animal being treated, and the physical characteristics of the specific animal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The modified polypeptides of the present disclosure and conjugates thereof may be particularly useful for treatment of humans.

An effective dosage and treatment protocol may be determined by conventional means, starting with a low dose in laboratory animals and then increasing the dosage while monitoring the effects, and systematically varying the dosage regime as well. Numerous factors may be taken into consideration by a clinician when determining an optimal dosage for a given subject. Such considerations are known to the person skilled in the art.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, arginine, lysine, or acetate or mixtures thereof. The term further encompasses any agents listed in the US Pharmacopeia for use in animals, including humans.

"Treatment" is an approach for obtaining beneficial or desired clinical results. For the purposes of the present disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder or disease as well as those in which the disorder or disease is to be prevented. By treatment is meant inhibiting or reducing an increase in pathology or symptoms when compared to the absence of treatment, and is not necessarily meant to imply complete cessation of the relevant condition.

The pharmaceutical compositions as described herein can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. In certain embodiments, packaged forms include a label or insert with instructions for use. Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intraocular and transdermal) administration. The formulations may conveniently be presented in unit dosage form and may be prepared by any of the methods well known in the art of pharmacy.

As used herein an "effective" amount or a "therapeutically effective amount" of a modified polypeptide as described herein or conjugate thereof refers to a nontoxic but sufficient amount of the modified polypeptide as described herein or conjugate thereof to provide the desired effect The amount that is "effective" will vary from subject to subject, depending on the age and general condition of the individual, mode of administration, and the like. An appropriate "effective" amount in any individual case may be determined by one of ordinary skill in the art using routine experimentation.

The terms "patient", "subject" and "individual" may be used interchangeably and refer to either a humans or non-human mammals. Aptly, the subject is a human.

The following examples refer to certain specific polypeptides. It will be appreciated that the methods used can be applied to other polypeptides including those referred to herein, such as for example antibodies and fragments thereof.

Example 1

Methods
Incorporation of Aldehyde Handle(s)
Materials and Reagents
Solvents and Starting Materials.

All solvents were dried prior to use according to standard methods, with the exception of solvents used for flash chromatography purposes, where GPR-grade solvents were used. All commercially-available reagents were used as received.

General Procedures.

All solution-phase reactions were carried out under a dry nitrogen atmosphere using oven-dried glassware unless otherwise stated. All concentrations were performed in vacuo unless stated otherwise. Analytical TLC was performed on silica gel 60-F$^{252}$ with detection by fluorescence and/or charring following immersion in a solution of ninhydrin (1.5 g in 100 mL n-butanol and 3 mL acetic acid). Flash column chromatography was carried out using Sigma silica (pore size 60 Å, 200-400 mesh).

Buffers
  A1: H$_2$O(HPLC grade), 0.1% (v/v) TFA. B1: MeCN (HPLC grade), 0.1% (v/v) TFA.
  A2: 4×PBS, pH 8.0, 10 mM imidazole. B2: 4×PBS, pH 8.0, 500 mM imidazole.
  C1: 100 mM phosphate buffer, 0.1 M NaCl, pH 7.0. C2: 100 mM phosphate buffer, pH 7.0.
  C3: 25 mM phosphate buffer, pH 7.5
  D1: 1×PBS, pH 7.4. D2: 10×PBS, pH 7.4.
  M1: 50:50:1 (v/v) MeCN (HPLC grade): H$_2$O(HPLC grade): formic acid.

Mass Spectrometry and NMR

Protein ESI mass spectra were obtained on a Bruker Solarix XR 9.4 T instrument. Samples of GFP were desalted and analysed at a final concentration of 0.4-10 µM in buffer M1. Small-molecule HRMS data were obtained at room temperature on a Bruker Daltonics micrOTOF. Small-molecule and peptide LCMS analysis was performed on a Dionex UltiMate 3000 Ci Rapid Separation LC system equipped with an UltiMate 3000 photodiode array detector probing at 250-400 nm using a Waters Symmetry C18 3.5 µm column, 4.6×75 mm, coupled to a HCT ultra ETD I ion trap spectrometer, in positive ion mode unless otherwise stated. All LCMS runs used Buffer A1 and Buffer B1 only.

$^1$H and $^{13}$C NMR spectra were recorded at 400 MHz and 101 MHz respectively on a JEOL ECS 400 instrument using an internal deuterium lock at room temperature. Chemical shifts are reported according to the following references:
  CDCl$_3$: $\delta_H$ 7.27 (CHCl$_3$), $\delta_C$ 77.0, centre of triplet (CDCl$_3$); D$_2$O: $\delta_H$ 4.79 (HOD); DMSO-d$_6$: $\delta_H$ 2.50 (DMSO-d$_5$), $\delta_C$ 39.52, centre of septet (DMSO-d$_6$); TFA-d: $\delta_H$ 11.5 (CF$_3$CO$_2$H), $\delta_C$ 116.6, centre of quartet (CF$_3$CO$_2$D).

Expression of GFP Containing Unnatural Amino Acids

The pBAD vector containing ampicillin resistance and either Ser-GFP(Y39TAG) or sfGFP(N150TAG) genes, together with the pEVOL vector containing tRNA$^{Pyl}$, pylRS (M. mazei, wild type) and chloramphenicol resistance genes, were co-transformed into electrocompetent E. coli Top10 cells and selected on LB agar plates containing ampicillin (100 µg/ml) and chloramphenicol (35 µg/ml). The pBAD GFP (Y39TAG) and pEVOL vectors were obtained from EMBL, and the pBAD sfGFP (N150TAG) was obtained from Addgene.

For small-scale expression, 0.5 mL of an overnight culture grown from a single colony was inoculated into 50 mL Terrific Broth Medium in a 250 mL non-baffled conical flask. At 37° C. with shaking (220 rpm), cells typically grew within 3 h to an OD$_{600}$ of 0.2-0.3, at which point unnatural amino acid (stock solution 80 mM in 0.1 M NaOH (aq.)) was added to a final concentration of 1.6 mM. The cultures were allowed to grow until an OD$_{600}$ of 0.4-0.6, at which point protein expression was induced by addition of L-arabinose (stock solution 20% (w/w)) at a final concentration of 0.02% (w/w). After further growth for 16-18 h (37° C., 220 rpm), the cultures were harvested by centrifugation (6 000×g, 4° C., 20 min). Pellets were resuspended in buffer A2 and a Pierce Protease Inhibitor (EDTA-free) tablet and then lysed by sonication on ice for 6×30 s with 30 s intervals. The lysate was clarified by centrifugation (20 000×g, 4° C., 20 min) and loaded onto Ni HiTrap Chelating HP column (1 ml, GE Healthcare) pre-equilibrated in buffer A2. The column was washed with 10 column volumes of A2 and then eluted using a gradient of 0-100% B2 over 7.5 column volumes, taking 0.5 mL fractions, and the column washed with 7.5 column volumes of B2, taking 0.5 mL fractions. Fractions containing full-length protein (as determined by SDS-PAGE) were pooled, dialysed into C1 and concentrated (Vivaspin centrifugal concentrator, 10000 MWCO) to a final concentration of 330 µM (as determined by UV-visible spectroscopy, $\varepsilon_{280}=2.0\times10^4$ $dm^3$ $mol^{-1}$ $cm^{-1}$) and stored at −80° C.

Pd-Mediated Thiazolidine Cleavage on GFP

Pd Reagent Screening Conditions

Palladium reagent 9 to 12 (stock 550 mM in DMSO, final concentration 33 mM) was added to 2b (stock 330 µM in buffer D1, final concentration 300 µM) in a 0.5 mL Eppendorf tube. The reaction mixture was vortex mixed for 1 s and incubated in a water bath at 37° C. The reaction was quenched by the addition of DTT (ca. 5 mg) and centrifuged (5000×g, 2 min). The supernatant was decanted and desalted using a PD SpinTrap G25 column (GE Healthcare Life Sciences) into $H_2O$ for mass spectrometry analysis or further manipulation.

Optimised Procedure for Decaging Using $Pd_2Dba_3$ 11 (stock 400 mM in DMSO, final concentration 30 mM, 8% (v/v) DMSO) was added to 2A/2B (stock 330 µM in buffer D1, final concentration 330 µM), mixed by pipette tip swirling, and incubated at 37° C. for 24 h. The reaction mixture was quenched by the addition of DTT (ca. 5 mg) and centrifuged (5000×g, 2 min). The supernatant was decanted, diluted to 500 µL and desalted using a PD Minitrap G-25 (GE Healthcare) into $H_2O$ for analysis and further manipulation.

Optimised Procedure for Decaging Using [Pd(Allyl)Cl]2

10 (stock 30 mM in DMSO, final concentration 0.30 mM, 1% (v/v) DMSO) was added to 2A (stock 300 µM in buffer D1, final concentration 0.30 µM), mixed by pipette tip swirling, and left at rt for 1 h. The reaction mixture was quenched by 3-mercaptopropanoic acid (stock 1% (v/v) in D2, final concentration 0.1% (v/v)) and left at rt for 15 min. The reaction mixture was diluted up to 500 µL and desalted using a PD Minitrap G-25 (GE Healthcare), gravity method, into $H_2O$ for analysis and further manipulation.

$NaIO_4$-Mediated Serine Cleavage on GFP

A solution of 2B/14 (stock 100 µM in buffer D1, final concentration 94 µM) was cooled to 0° C. on ice. Freshly prepared solutions of L-methionine (stock 66 mM in buffer C1, 3 µL) and $NaIO_4$ (stock 330 µM in buffer C1, 3 µL) were added to the reaction vessel. After vortex mixing (1 s), the reaction mixture was left in the dark at 0° C. on ice for 5 min. The reaction mixture was desalted using a PD SpinTrap G25 column (GE Healthcare) into $H_2O$ for mass spectrometry analysis and further manipulation.

Solid-Phase Peptide Synthesis

General Procedures

Preloaded Resin Preparation.

The preloaded 2-chlorotrityl resin was weighed out into a 2 mL SPPS cartridge fitted with a PTFE stopcock, swollen in DCM for 30 min and then filtered.

Fmoc Deprotection.

A solution of 20% piperidine in DMF was added to the resin and gently agitated by rotation for 2 minutes. The resin was filtered off and repeated four more times, followed by washes with DMF (5×2 min with rotation).

Amino Acid Coupling.

DIPEA (11 eq.) was added to a solution of amino acid (5 eq.) and HCTU (5 eq.) dissolved in the minimum volume of DMF and the solution added to the resin. The reaction mixture was gently agitated by rotation for 1 h, and the resin filtered off and washed with DMF (3×2 min with rotation).

Cleavage Cocktails:

Deprotection and resin cleavage: 95:2.5:2.5 (v/v) TFA:$H_2O$:triisopropylsilane.

Cleavage and Isolation:

The resin was washed with DCM (3×2 min with rotation) and MeOH (3×2 min with rotation). The resin was dried on a vacuum manifold and further dried on a high vacuum line overnight. A solution of cleavage cocktail was added to the resin and gently agitated by rotation for 60 min.

For peptides cleaved and deprotected: the reaction mixture was drained into ice-cold $Et_2O$ and centrifuged at 4000 rpm at 4° C. until pelleted (ca. 5-10 min). The supernatant was carefully decanted and subsequently resuspended, centrifuged and supernatant decanted three more times. The precipitated peptide pellet was dissolved in 10% aq. AcOH and lyophilised.

Solution-Phase Synthesis

Thiazolidine 2-Carboxylic Acid (Racemate)

SCHEME 1

A solution of 2-aminoethane thiol hydrochloride 3 (2.84 g, 25 mmol) in 5:2 (v/v) ethanol:pyridine (14 mL) was added to a stirred solution of glyoxylic acid 4 (50% solution in water, 3.7 g, 25 mmol, 1 eq.) in ethanol (5 mL). The reaction was left to stir for 2 h at rt, after which the off-white precipitate was isolated by filtration and washed with ethanol, yielding racemic thiazolidine-2-carboxylic acid 5 as a white powder (2.67 g, 80%), used without further purification; δH (400 MHz, $D_2O$): 5.10 (s, 1H, CH), 3.68-3.74 (m, 1H), 3.57-3.63 (m, 1H), 3.16-3.20 (m, 2H); $\delta_C$ (101 MHz, $D_2O$): 171.7 ($RCO_2H$), 62.3 (CH), 49.3 ($CH_2$), 29.5 ($CH_2$); IR: 3109.8 (Nh HRMS: Found $[M+H]^+$ 134.0270; $C_4H_8NO_2S$ requires 134.0270 (Δ=0.2 ppm).

3-(tert-butoxycarbonyl)thiazolidine-2-carboxylicacid (racemate)

SCHEME 2

A stirred solution of thiazolidine-2-carboxylic acid 5 (2.7 g, 20 mmol) in THF (70 mL) was cooled to 0° C. with stirring and di-tert-butyl dicarbonate (11.0 g, 50 mmol, 1 eq.) added, followed immediately by a solution of sodium hydrogencarbonate (10.0 g, 120 mmol, 2.2 eq.) in water (70 mL). The mixture was allowed to warm to room temperature and left stirring for 18 h. The reaction mixture was concentrated to remove organic solvent, diluted with water (70 mL), and washed with Et$_2$O (2×30 mL). The aqueous layer was acidified with 6 M HCl to pH 1 and washed with DCM (3×30 mL). The organic layers were combined, dried over MgSO$_4$ and concentrated to yield the crude product 6 as a thick pale yellow oil in quantitative yield used without further purification; $\delta_H$ (400 MHz, DMSO-d$_6$): 5.07 (s, 1H, CH, rotamers present), 3.71 (m, 2H, CH$_2$), 3.05 (br s, 2H, CH$_2$), 1.46 (s, 9H, CH$_3$); $\delta^C$ (101 MHz, CDCl$_3$): 169.9 (CO$_2$H), 152.9 (NHCO$_2$), 82.0 and 81.1 (C(CH$_3$)$_3$), 60.9 and 60.3 (CH), 49.9 and 49.6 (CH$_2$), 30.7 and 29.6 (CH$_2$), 28.3 and 27.9 (CH$_3$); HRMS: found [M+Na]$^+$ 256.0610; C$_9$H$_{15}$NO$_4$SNa requires 256.0614 (Δ=1.9 ppm).

Methyl (2S)-2-(tert-butoxycarbonyamino)-6-(thiazoidine-2-carboxamido-3-(tert-butoxycarbonyl)) hexanoate (mixture of diastereomers)

SCHEME 3

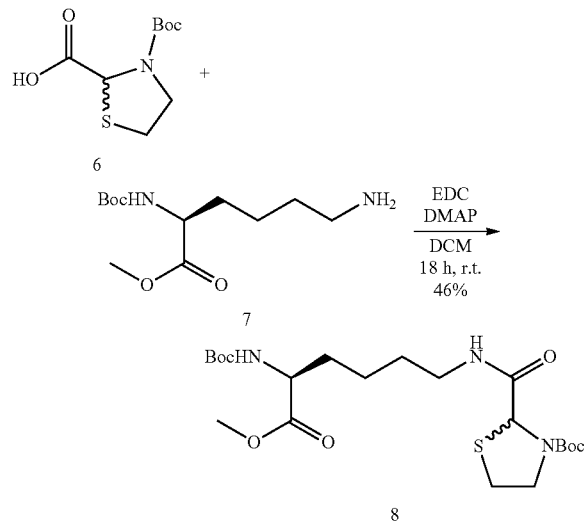

3-(tert-butoxycarbonyl)thiazolidine-2-carboxylic acid 6 (2.0 g, 8.6 mmol, 1.0 eq.) in dry DCM (2 mL) was added to a stirred solution of methyl 2-(tert-butoxycarbonylamino) hexanoate 7 (2.7 g, 10.4 mmol, 1.2 eq.) in dry DCM (5 mL) under nitrogen atmosphere. The reaction vessel was cooled to 0° C. and 1-ethyl-3-(3-dimethylaminopropyl)carbodiimide hydrochloride (1.5 g, 7.9 mmol, 1.0 eq.) and 4-dimethylaminopyridine (400 mg, 3.3 mmol, 0.4 eq.) were added sequentially in one portion. The reaction vessel was left to warm to r.t. and stirred under nitrogen atmosphere for 18 h. Concentration of the reaction material afforded a pale yellow oil, which was purified by flash chromatography (silica, DCM:MeOH (v/v) 20:0→19:1) to afford the product 8 as a colourless oil (2.34 g, 57%); $\delta_H$ (400 MHz, CDCl$_3$): 6.09 and 5.67 (2×s, total 1H, N$_\varepsilon$H), 5.23 (s, 1H, Thz CH), 5.09 (d, 1H, $^3J_{H-H}$ 7.0 Hz, NaH), 4.26 (m, 1H, H$_\alpha$), 3.85-3.95 (br m, 1H, Thz CH$_2$), 3.74-3.79 (m, 1H, Thz CH$_2$), 3.73 (s, 3H, OCH$_3$), 3.06-3.34 (br m, 3H, H$_\varepsilon$ and Thz CH$_2$), 2.93 (ddd, 1H, 2J$_{H-H}$ 11.0 Hz, $^3$H$_{H-H}$ 6.0 Hz, $^3J_{H-H}$ 5.0 Hz, Thz CH$_2$), 1.71-1.87 (m, 2H, H$_\beta$), 1.49-1.57 (m, 2H, H$_\delta$), 1.44 (s, 18H, Boc), 1.30-1.40 (m, 2H, H$_\gamma$); $\delta_C$ (101 MHz, CDC): 173.4 (CO$_2$R), 170.3 (CONHR), 155.6 (RHNCO$_2$R), 81.7 (OCMe$_3$), 55.3 (Thz CH), 52.5 (Cα), 52.44 (OCH$_3$), 50.3 (Thz CH$_2$), 39.4, 32.4 (Lys CH$_2$), 29.2 (Thz CH$_2$), 28.4 (Boc CH$_3$), 23.4, 22.5 (Lys CH$_2$); HRMS: found [M+Na]$^+$ 498.2251; C$_{21}$H$_{37}$N$_3$O$_7$SNa requires 498.2244 (Δ=−0.8 ppm).

Methyl 2-amino-6-(thiazoidine-2-carboxamido) hexanoate (mixture of diastereomers)

SCHEME 4

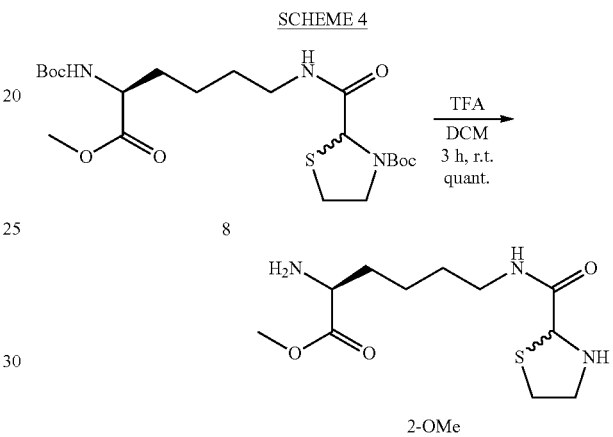

Trifluoroacetic acid (0.5 mL) was added dropwise to a stirred solution of methyl 2-(tert-butoxycarbonylamino)-6-(thiazolidine-2-carboxamido-3-(tert-butoxycarbonyl)) hexanoate 8 (210 mg, 0.44 mmol) in DCM (1 mL) at 0° C. Once the reaction was determined complete by TLC, usually within 3 h, the solvent was removed in vacuo. The resulting yellow oil was redissolved in 10% (v/v) aqueous acetic acid and lyophilised to afford the product 2-OMe (1) as a thick yellow oil in quantitative yield and in purity sufficient for further manipulations; $\delta_H$ (400 MHz, TFA-d): 5.58 and 5.54 (2×s, total 1H, Thz CH, mixture of diastereomers), 4.17-4.28 (m, 1H, H$_\alpha$), 3.99-4.05 (m, 1H, Thz CH$_2$), 3.83 and 3.87 (s, 3H, OCH$_3$), 3.69-3.78 (m, 1H, Thz CH$_2$), 3.28-3.36 (m, 2H, H$_\varepsilon$), 3.15-3.27 (m, 2H, Thz CH$_2$), 1.96-2.12 (m, 2H, H$_\beta$), 1.62-1.54 (m, 2H, H$_\delta$) 1.43-1.53 (m, 2H, H$_\gamma$); $\delta_C$ (101 MHz, TFA-d): 171.5 (C$_2$R), 168.8 (CONHR), 63.2 (Thz CH), 55.1 (C$_\alpha$), 52.1 (OCH$_3$), 41.1 (Thz CH$_2$), 30.5 (Lys CH$_2$), 30.2 (Thz CH$_2$), 28.3, 22.6 (Lys CH$_2$); HRMS: found [M+H]$^+$ 276.1387; C$_{11}$H$_{22}$N$_3$O$_3$S requires 276.1376 (Δ=−3.2 ppm).

2-OMe 1 was incorporated into Green Florescent Protein (GFP) and superfolder Green Fluorescent Protein (sfGFP) using the unnatural amino acid mutagenesis method, amber codon suppression technology. Green fluorescent protein (GFP) and superfolder green fluorescent protein (sfGFP) are highly useful test systems for protein modification as denaturation can be observed through the loss of fluorescence and green colouration. Two GFP mutants containing amber stop codons at surface-exposed sites were selected: sfGFP (N150TAG) (Miyake-Stoner et al, Biochemistry, 2010, 49, 1667-1677) (and Ser-GFP(Y39TAG) (Plass et al, Angew, Chem, Int, Ed, 2011, 50, 3878-3881) with the latter protein containing an additional mutation to install a serine residue at the N terminus for periodate-mediated oxidation.

The GFP protein (SEQ ID NO: 2-Ser-GFP(Y39TAG)) comprises a terminal serine residue which was mutated using standard DNA mutation methods (QuikChange II Site-Directed Mutagenesis Kit, Agilent) using primers 5'-cactttatcatcatcatctttgtaagacatggttaattcctcctgttagccc-3' and 5'-gggctaacaggaggaattaaccatgtcttacaaagatgatgatgataaagtg-3'), and a surface exposed tyrosine (Tyr) 39 residue which was mutated to the amber stop codon Thymidine, Adenosine and Guanine (TAG). The GFP(Y39TAG) (SEQ ID NO: 1) was expressed in E. Co/i cells using the method as described in Plass et al. with the *E. coli* cells co-expressing *Methanosarcina. mazei* wild type pyrrolysine tRNAcu-tRNA synthetase (pylRS) with the supplementation of 2-OMe (1) in 0.1 M aqueous sodium hydroxide at a final amino acid concentration of 5 mM.

Figure 2:
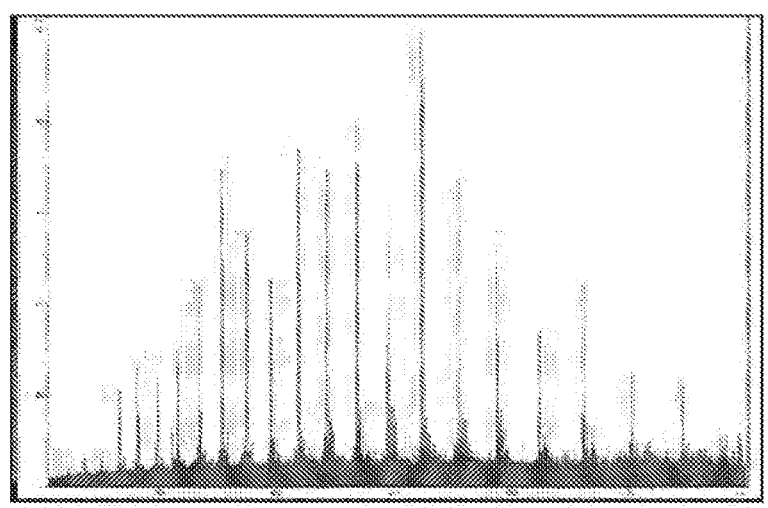
FIG. 2 shows a raw Electrospray Ionization Fourier Transform Ion Cyclotron Resonance Mass Spectrometry (ESI-FTICR-MS) spectrum of 2B.
Figure 3:
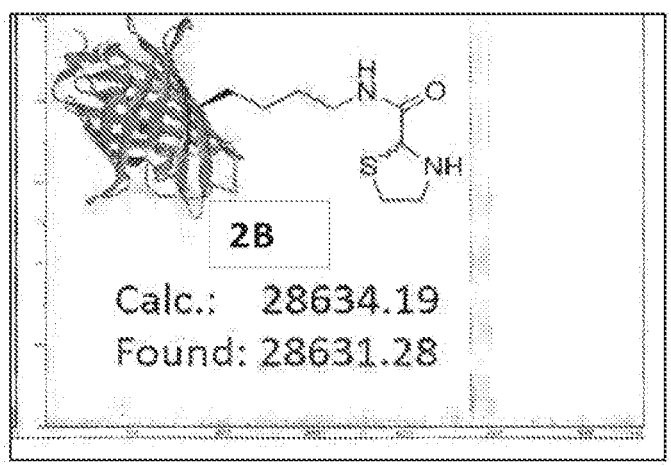
FIG. 3 shows the structure of 2B with the deconvoluted ESI-FTCIR-MS spectrum of 2B shown in FIG. 2.
Figure 4:
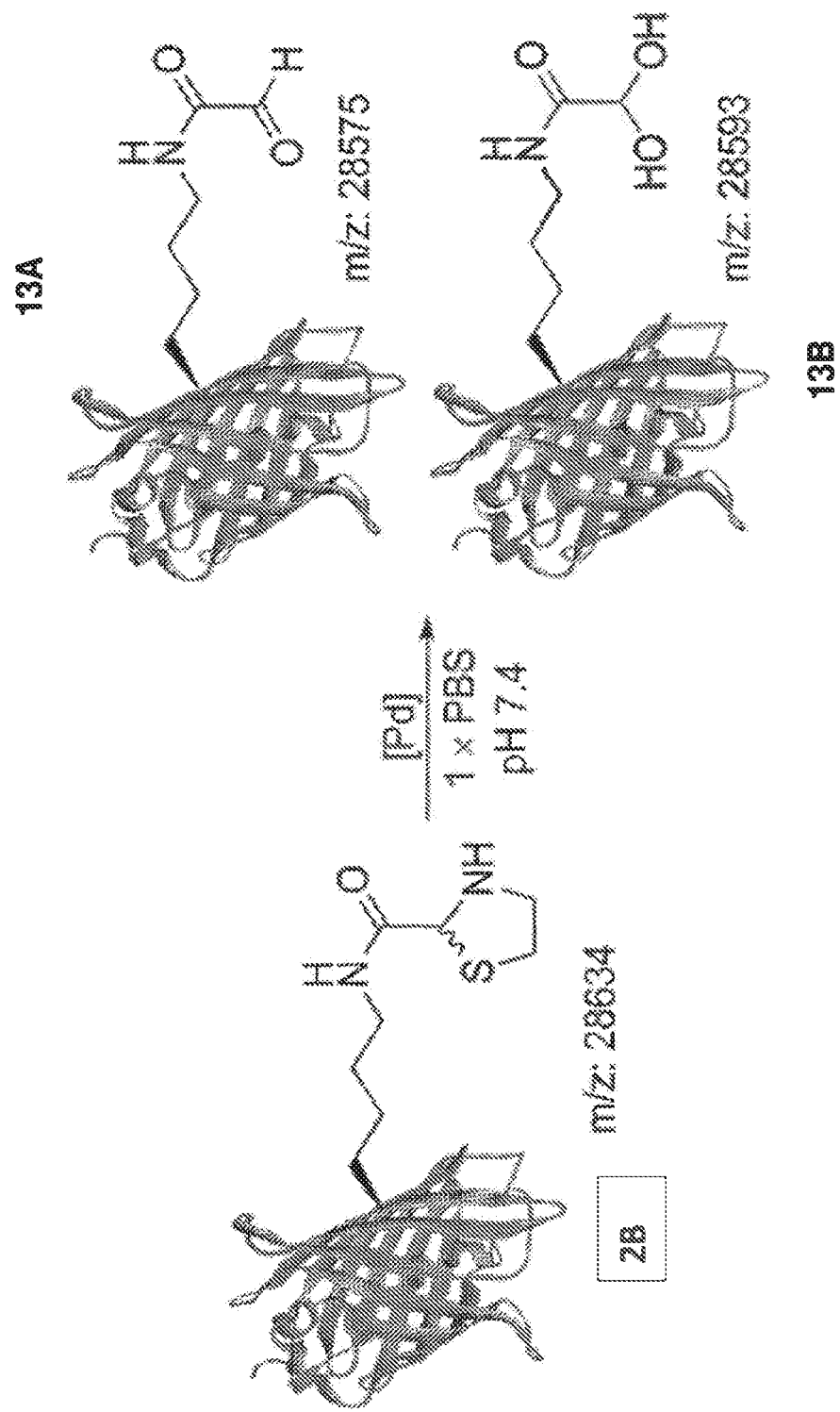
FIG. 4 illustrates a decaging reaction of 2B using palladium containing compounds. The reaction involves palladium containing compounds ([Pd]) and is carried out at pH 7.4 in phosphate buffered saline (PBS). Decaging breaks the thiazolidine ring and forms an aldehyde 13A (also referred to as GFP(Y39GlyoxylK)) and a hydrate 13B which was also formed in low quantities in equilibrium.
Figure 5:
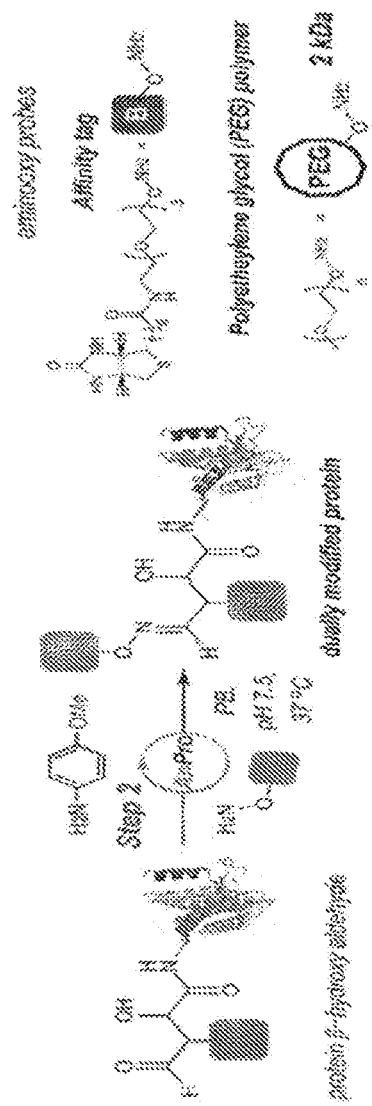
FIG. 5 is a generic depiction of oxime formation on protein β-hydroxy aldehydes, and aminoxy reagents utilised in modification of fluorescently labelled thioredoxin and myoblobin proteins.
Figure 6:
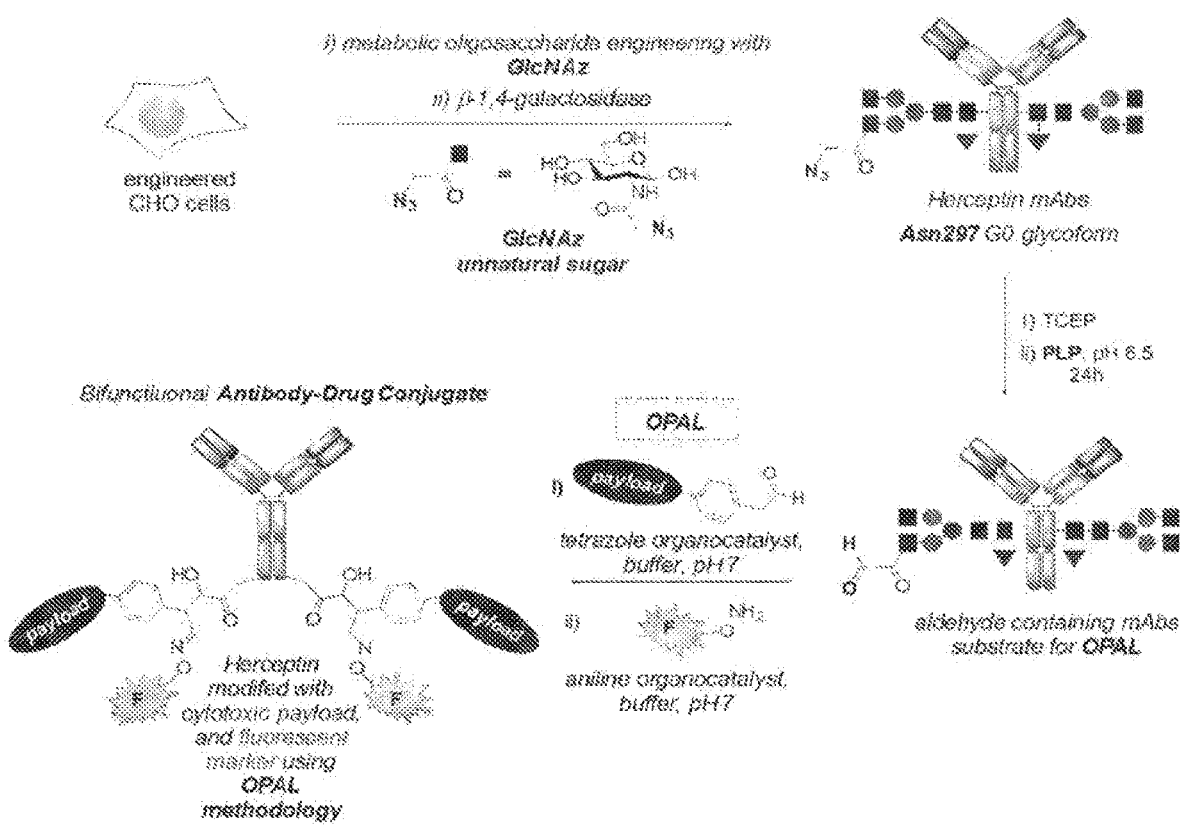
FIG. 6 is a schematic representation of using the methods described herein using glycans to install glyoxyl groups into antibodies without the need to mutate the underlying DNA molecule.

Expression of GFP was confirmed by florescence of the harvested cells. The GFP with tyrosine 39 mutated to thiazolidine lysine (ThzK) (GFP(Y39ThzK)) 2B (SEQ ID NO: 1) was purified from samples using standard nickel affinity purification. Purity was confirmed by SDS-PAGE (FIG. 1) and ESI-FTICR-MS (FIG. 2 & FIG. 3). The structure of the 2B can be seen in FIG. 3.

GFP Purification

For a typical 50 mL culture scale preparation, cells were harvested by centrifugation (8000×g, 20 min) and the pellet resuspended in ca. 12 mL in 4×PBS, 10 mM imidazole, pH 8.0 with protease inhibitors. Cells were lysed by sonication, 30 s bursts with 30 s rest intervals, until lysis was complete and subsequently centrifuged (17 000×g, 20 min). The supernatant was loaded onto a 1 mL Ni HiTrap Chelating HP column (GE Healthcare) column pre-equilibrated in 4×PBS, 10 mM imidazole, pH 8.0. The column was washed with 10 column volumes of 4×PBS, 10 mM imidazole, pH 8.0 and then eluted using a gradient of 0-100% 4×PBS, 500 mM imidazole, pH 8.0 over 7.5 column columes, taking 0.5 mL fractions, and the column washed with 7.5 column volumes of 4×PBS, 500 mM imidazole, pH 8.0, taking 0.5 mL fractions. Fractions containing full-length protein (as determined by SDS-PAGE) were pooled, dialysed into 1×PBS, pH 7.4 and concentrated using a Vivaspin centrifugal concentrator (Sartorius Stedim Biotech).

Final concentrations of all starting materials are given below the respective compounds in the figure. The final volume of the reaction is below the reaction arrow. Each component described in the text follows 'concentration of stock solution, volume taken of stock solution, solvent of stock solution'. Plasmid containing sfGFP N150TAG gene (which is renamed sfGFP (N150ThzK) once unnatural ThzK amino acid has been incorporated was acquired from addgene plasmid pBad-sfGFP 150TAG, addgene #85483.

Decaging of sfGFP(N150ThzK)

SCHEME 5

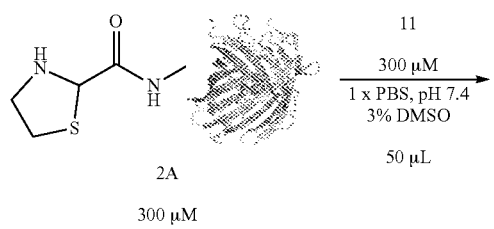

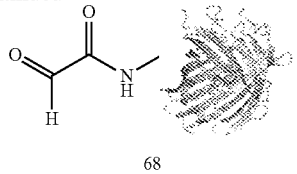

68

An aliquot of sfGFP(N150ThzK) 2A (330 μM, 45 μL, 1×PBS, pH 7.4) was charged with 1×PBS pH 7.4 (4.5 μl). The solution was then charged with allylpalladium(II) chloride dimer 11 (10 mM, 1.5 μL, DMSO). The solution was mixed by gentle pipetting, and allowed to sit at room temperature for 60 min without further agitation. The reaction was then quenched with 3-mercaptopropanoic acid (1% (v/v) in 10×PBS, pH 7.4, 10 μl), mixed by gentle pipetting, and allowed to sit at room temperature for 15 min without further agitation. The reaction was immediately purified using a PD MiniTrap G25 desalting column (GE Healthcare Life Sciences), eluting into MQ H$_2$O. Conversion to the decaged protein aldehyde, sfGFP(N150GlyoxylK) 68 was confirmed by ESI-MS analysis.

Further Optimisation of Pd Mediated Decaging of Thiazolidine Containing Proteins Further experiments were performed using a range of concentrations of palladium catalysts 9 to 12 and a range of concentrations of 2B.

Initially a reaction was set up using 25 μM of 2B (final concentration), 100 μM palladium catalyst (final concentration) in PBS pH 7.4. The reaction mix was then incubated at 37° C. for 1 hour before addition of 1 μl of 1% 3-mercaptopropanoic acid solution for every 10 μl of reaction solution in order to quench excess catalyst. Quenched solution was then incubated at room temperature for 15 minutes and then desalted using a PD SpinTrap G25 column (GE Healthcare Life Sciences) into H$_2$O for mass spectrometry analysis or further manipulation. Efficiency of decaging was determined by ESI-MS.

This reaction process was repeated using protein concentrations of 2B up to 300 μM and catalyst concentrations.

Incorporation of Aldehyde Handle into SLYRAG Peptide Using Sodium Periodate

Oxidation of SLYRAG 15 (SEQ ID NO: 5) to Glyoxyl-LYRAG 16A was carried out by dissolving a desired amount of 15 in 1 ml of 25 mM phosphate buffer (PB) pH 7.0, followed by addition of 2 equivalents of NaIO$_4$ (see Scheme 6 below).

Scheme 6

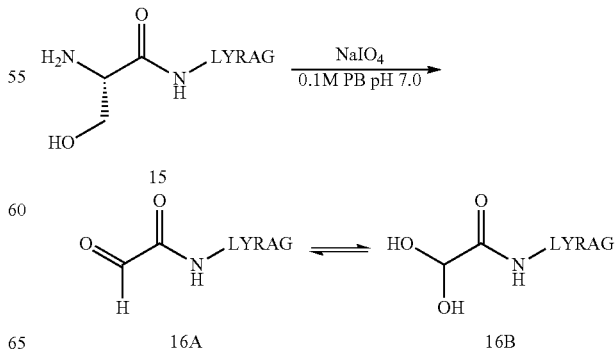

The solution was vortexed, then allowed to sit at room temperature in the dark for 1 hour. The solution was then loaded onto a solid phase extraction cartridge (Grace Davison Extract Clean, 8 ml reservoir, Fisher Scientific) equilibrated with water/acetonitrile. After initial washing with water, the product was eluted over a gradient of acetonitrile. Fractions containing pure, oxidised peptide (as determined by Liquid-chromatography mass spectrometry (LC-MS) analysis) were pooled and subsequently lyophilised to give Glyoxyl-LYRAG as an orange-pink powder.

Figure 7:
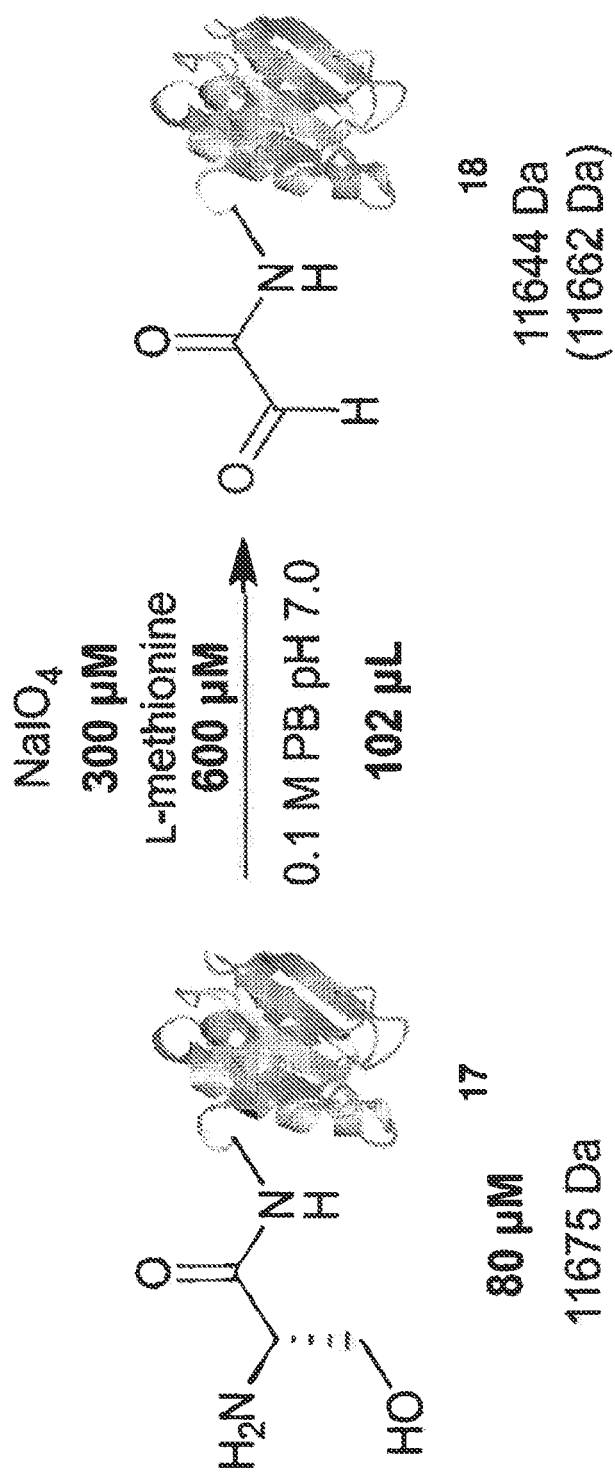
FIG. 7 illustrates oxidation of the terminal serine residue of thioredoxin 17 to a glyoxyl group forming glyoxyl-thioredoxin (also referred to as α-oxo-aldehyde thioredoxin) 18. The reaction utilises sodium periodate (NaIO$_4$) and L-methionine as a quenching agent to remove excess periodate and prevent oxidation of methionines in the protein. The reaction conditions are shown below the reaction arrow. The molecular weight of the substrate and product are also shown in Daltons (Da)

Incorporation of Aldehyde Handle into Thioredoxin Using Sodium Periodate (FIG. 7)

An aliquot of thioredoxin 17 (85 μM thioredoxin in 100 μL of 25 mM Phosphate Buffer (PB) at pH 7.5) was charged with L-methionine (66 mM in 1 μL of 0.1 M PB and 0.1 M NaCl), and NaIO$_4$ (33 mM in 1 μL of 0.1 M PB and 0.1 M NaCl at pH 7.0). The solution was mixed by gentle pipetting, and allowed to sit on ice in the dark for 4 minutes. The reaction was immediately purified by size-exclusion chromatography (SEC) using a PD SpinTrap G25 column (GE Healthcare Life Sciences), eluting into 25 mM PB pH 7.5. Oxidation to glyoxyl-thioredoxin 18 was confirmed by LC-MS analysis.

Figure 8:
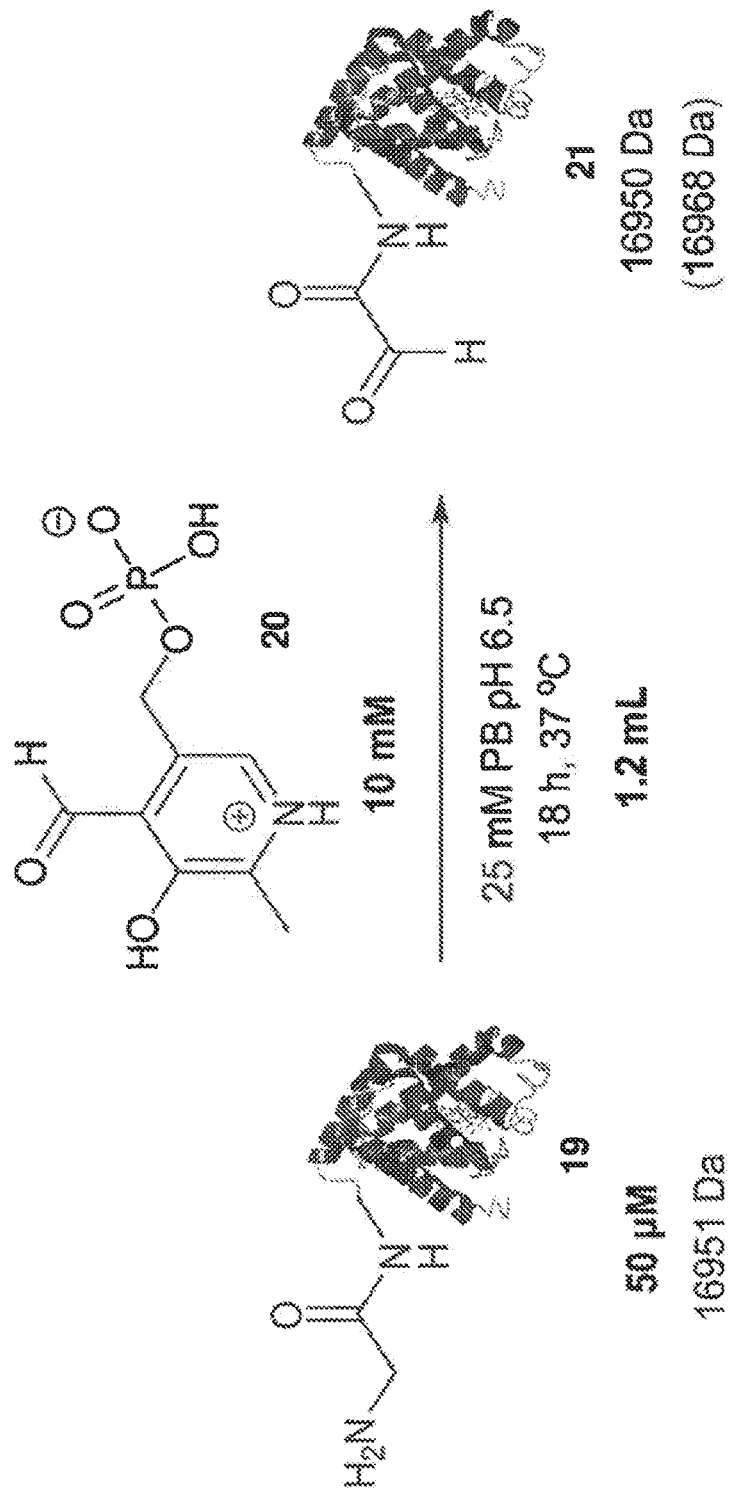
FIG. 8 illustrates oxidation of the terminal glycine residue of horse heart myoglobin 19 to a glyoxyl group forming glyoxyl-myoglobin (also referred to as α-oxo-aldehyde myoglobin) 21. The reaction utilises pyridoxal-5-phosphate (PLP) 20 as a catalyst for transamination of the terminal glycine residue. The reaction conditions are shown below the reaction arrow. The molecular weight of the substrate and product are also shown in Daltons (Da)

Incorporation of Aldehyde Handle into Horse Heart Myoglobin pyridoxal-5-phosphate (PLP) (FIG. 8)

A 2.0 ml Eppendorf was charged a solution of horse heart myoglobin 19 (250 μM myoglobin in 240 μL of 25 mM PB at pH 6.5), pyridoxal-5-phosphate (PLP) 20 (20 mM in 600 μL of 25 mM PB pH 6.5, pH adjusted to 6.5 using concentrated NaOH), and 25 mM PB pH 6.5 (360 μL). Final pH of solution was checked either by pH probe or pH paper. The mixture was briefly agitated, and incubated at 37° C. without further agitation for 24 hours. PLP 20 was removed via spin concentration (10,000 Molecular weight cut off (MWCO)) and the glyoxyl-myoglobin 21 solution was concentrated to 200 μM, eluting with water. Oxidation to glyoxyl-myoglobin 21 was confirmed by LC-MS analysis.

Figure 9:
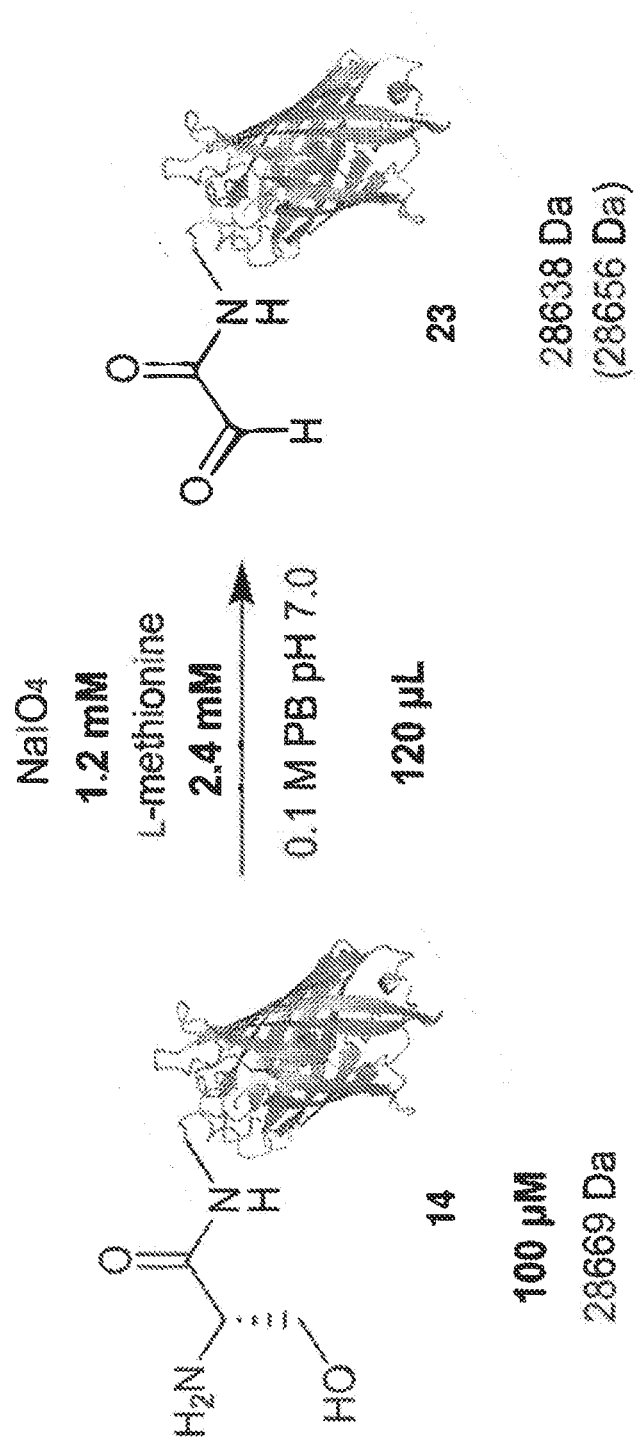
FIG. 9 illustrates oxidation of the terminal serine residue of GFP 14 to a glyoxyl group forming glyoxyl-GFP (also referred to as α-oxo-aldehyde GFP) 23. The reaction utilises sodium periodate (NaIO$_4$) and L-methionine as a quenching agent. The reaction conditions are shown below the reaction arrow. The molecular weight of the substrate and product are also shown in Daltons (Da)

Incorporation of Aldehyde Handle into GFP Using Sodium Periodate (FIG. 9)

An aliquot of GFP with tyrosine 39 mutated to 2-cyclooctynyloxycarbonyl lysine (GFP(Y39CycloOK)) 14 (100 μM, 100 μl, PBS pH 7.4) was charged with L-methionine (66 mM, 3 μl, 0.1 M PB, 0.1 M NaCl), and NaIO$_4$ (33 mM, 3 μl, 0.1 M PB, 0.1 M NaCl, pH 7.0). The solution was mixed, and allowed to sit on ice in the dark for 5 minutes. The reaction was immediately purified by size-exclusion chromatography (SEC) using a PD SpinTrap G25 column (GE Healthcare Life Sciences), eluting into 25 mM PB pH 7.5. Oxidation to glyoxylLAG-GFP(Y39CycloOK) 23 was confirmed by LC-MS analysis.

Bioconjugation of Functional Groups

Figure 10:
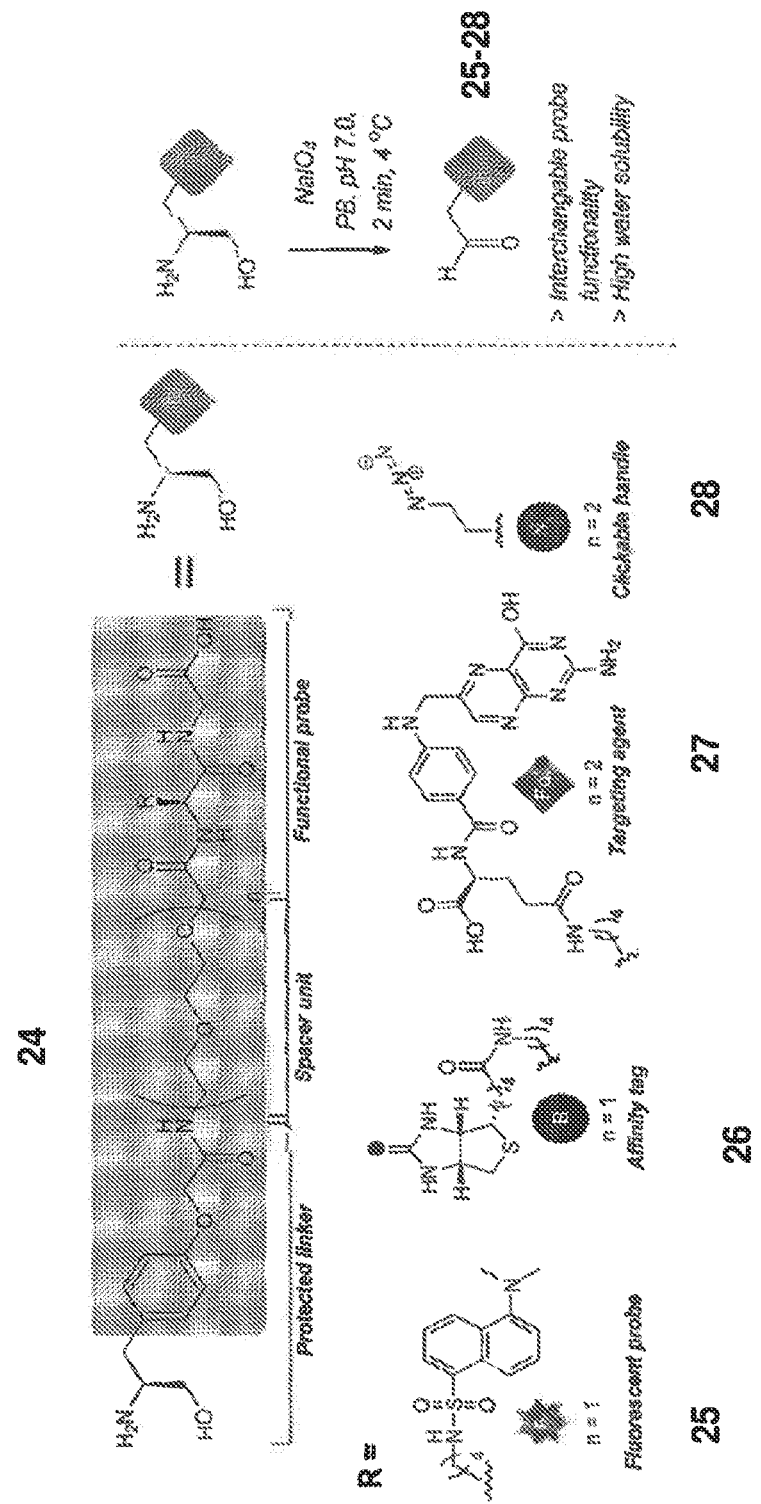
FIG. 10 illustrates the basic structure of an aldehyde donor comprising a functional aldehyde donor 24 which was synthesised by solid phase peptide synthesis (SPPS). R groups that were utilised as functional moieties are shown below 24 which included a fluorescent moiety 25, a biotin moiety 26, a folate moiety 27 and an azide moiety 28 (A). (B) illustrates the sodium periodate oxidation used to unmask the aldehyde group of 24.

Site-selective bioconjugation of a range of proteins was performed using functionalized α-aryl aldehyde donors (also referred to as probes). Functional groups, which are shown in FIG. 10A, were constructed by solid phase peptide synthesis (SPPS) using commercially available building blocks and an aldehyde precursor to form 24, which was unmasked using a biologically compatible periodate oxidation (FIG. 10B). Functional groups (R groups) attached to the aldehyde donor included, a fluorescent label 25, a biotin affinity tag 26, a folate targeting moiety 27, and a bioorthogonal azide handle 28. These functional groups were then deployed in a site-selective organocatalyst-mediated protein aldol ligation (OPAL) modification of a variety of α-oxo-aldehyde (e.g. glyoxyl) containing proteins.

Determination of OPAL Reaction Conditions

An aliquot of glyoxyl-myoglobin 21 (200 μM, 100 μl, MilliQ H$_2$O) was charged with an aliquot of 50 mM PB pH 7.5 (50 μl), and then charged with aliquot of L-proline 33 (200 mM, 25 μl, 50 mM PB pH 7.5). The solution was then charged with an aliquot of butyraldehyde 30 (200 mM, 25 μl, 50 mM PB pH 7.5). Following mixing by pipetting, the reaction was allowed to sit at 37° C. for 6 hours without further agitation to produce 31. Trypsin digest and LC-MS/MS analysis of fragments produced by the trypsin digested was used to confirm the site of the OPAL reaction. UV/Vis spectroscopic measurements of the haem group were also used to determine protein tertiary structure.

Screening of Catalysts and Aldehyde Donors for OPAL Reaction

Initially a panel of secondary amines was screened to investigate their ability to catalyse the ligation using a model peptide substrate, glyoxyl-LYRAG 16A and acetaldehyde as an aldehyde donor 32. Second order rate constants for each catalyst (33-38) at 1, 10, and 25 mM loadings were obtained. Next the nature of the α-carbon substituent of the aldehyde donor was investigated by performing reactions using aldehyde donors bearing an aryl substituent (e.g. phenyl acetylaldehyde). Reactions were as shown in Scheme 7 below.

Scheme 7

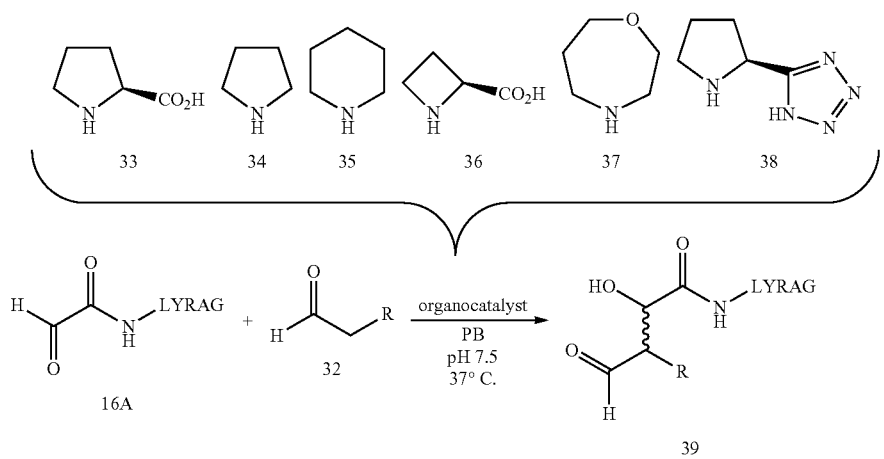

Figure 11:
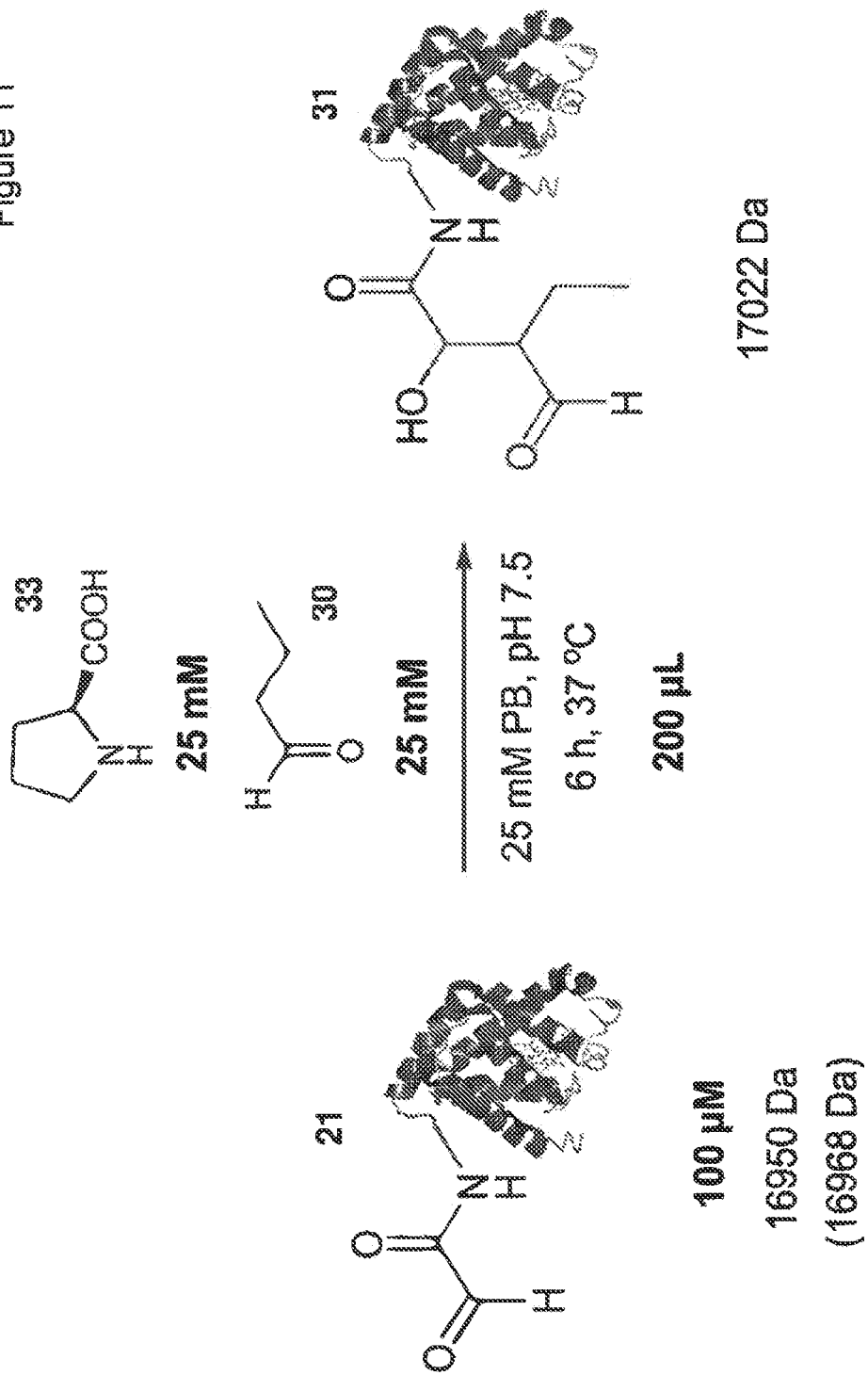
FIG. 11 illustrates a site-selective organocatalyst-mediated protein aldol ligation (OPAL) (also referred to as an enamine/protein (EnPro) activation) of glyoxyl-myoglobin 21 with butyraldehyde 30 using L-proline 33 as a catalyst to produce 31. The reaction conditions are shown below the reaction arrow. Molecular weights of the substrate and product are also shown in Da.

Bioconjugation of Butyraldehyde to Glyoxyl-Myoglobin by OPAL (FIG. 11)

An aliquot of glyoxyl-myoglobin 21 (200 μM, 100 μl, MilliQ H$_2$O) was charged with an aliquot of 50 mM PB pH 7.5 (50 μl), and then charged with aliquot of L-proline 33 (200 mM, 25 μl, 50 mM PB pH 7.5). The solution was then charged with an aliquot of butyaldehyde 30 (200 mM, 25 μl, 50 mM PB pH 7.5). Following mixing by pipetting, the reaction was allowed to sit at 37° C. for 6 hours without further agitation. The resulting OPAL product 31 was characterised by LC-MS.

Figure 12:
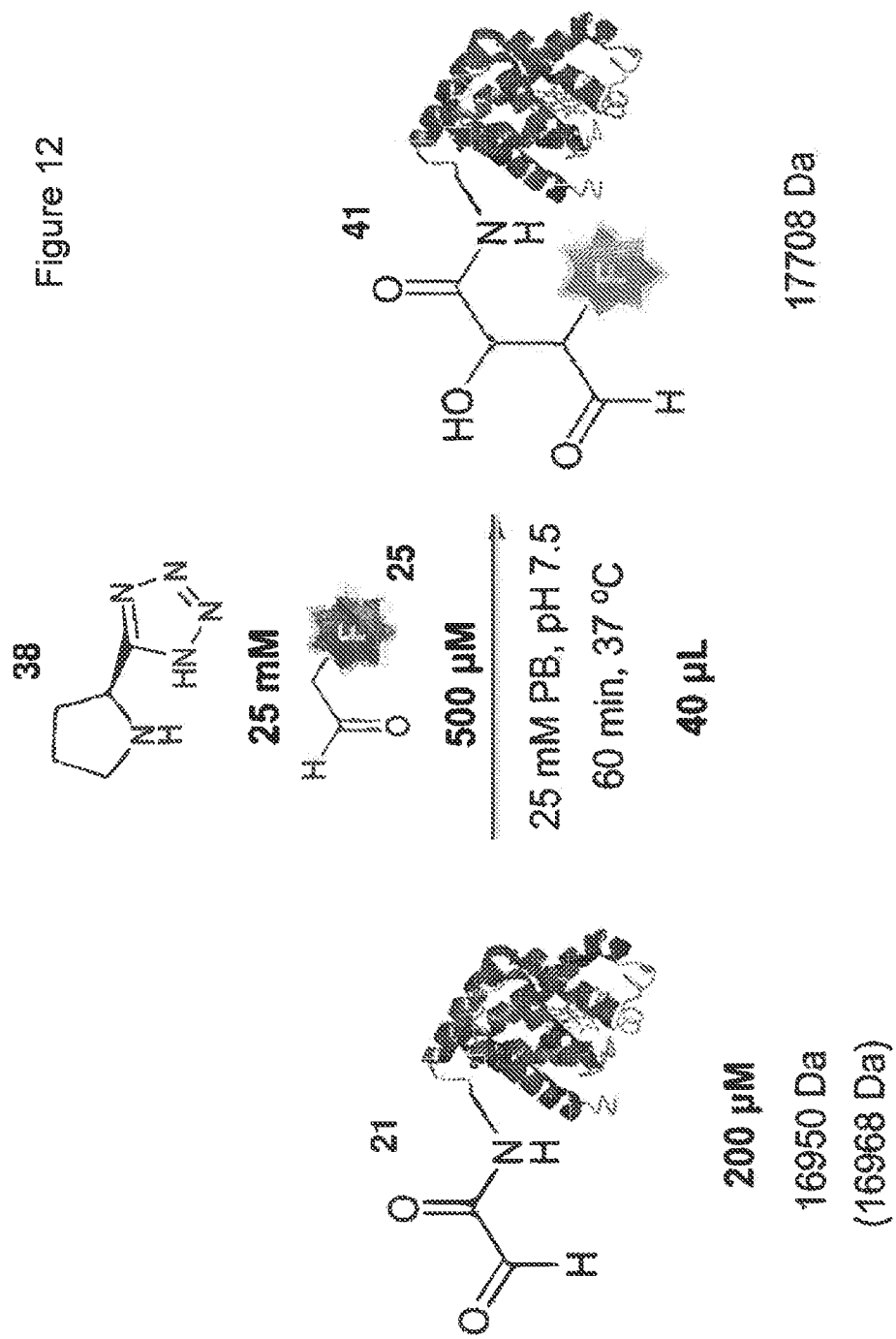
FIG. 12 illustrates an OPAL modification of glyoxyl-myoglobin 21 with the aldehyde donor comprising a fluorescent moiety 25 using proline tetrazole 38 as a catalyst to produce 41. The reaction conditions are shown below the reaction arrow. Molecular weights of the substrate and product are also shown in Da.

Bioconjugation of Florescent Group to Glyoxal-Myoglobin by OPAL (See FIG. 12)

An aliquot of glyoxyl-myolgobin 21 (200 μM, 25 μl, 25 mM PB pH 7.5) was charged with an aliquot of proline tetrazole 38 (200 mM, 5 μl, 25 mM PB pH 7.5). The solution was then charged with fluorescent aryl probe 25 (2 mM, 10 μl, 25 mM PB pH 7.5). Following mixing by pipetting, the reaction was allowed to sit at 37° C. for 60 minutes without further agitation. The resulting OPAL product 41 was characterised by LC-MS.

Figure 13:
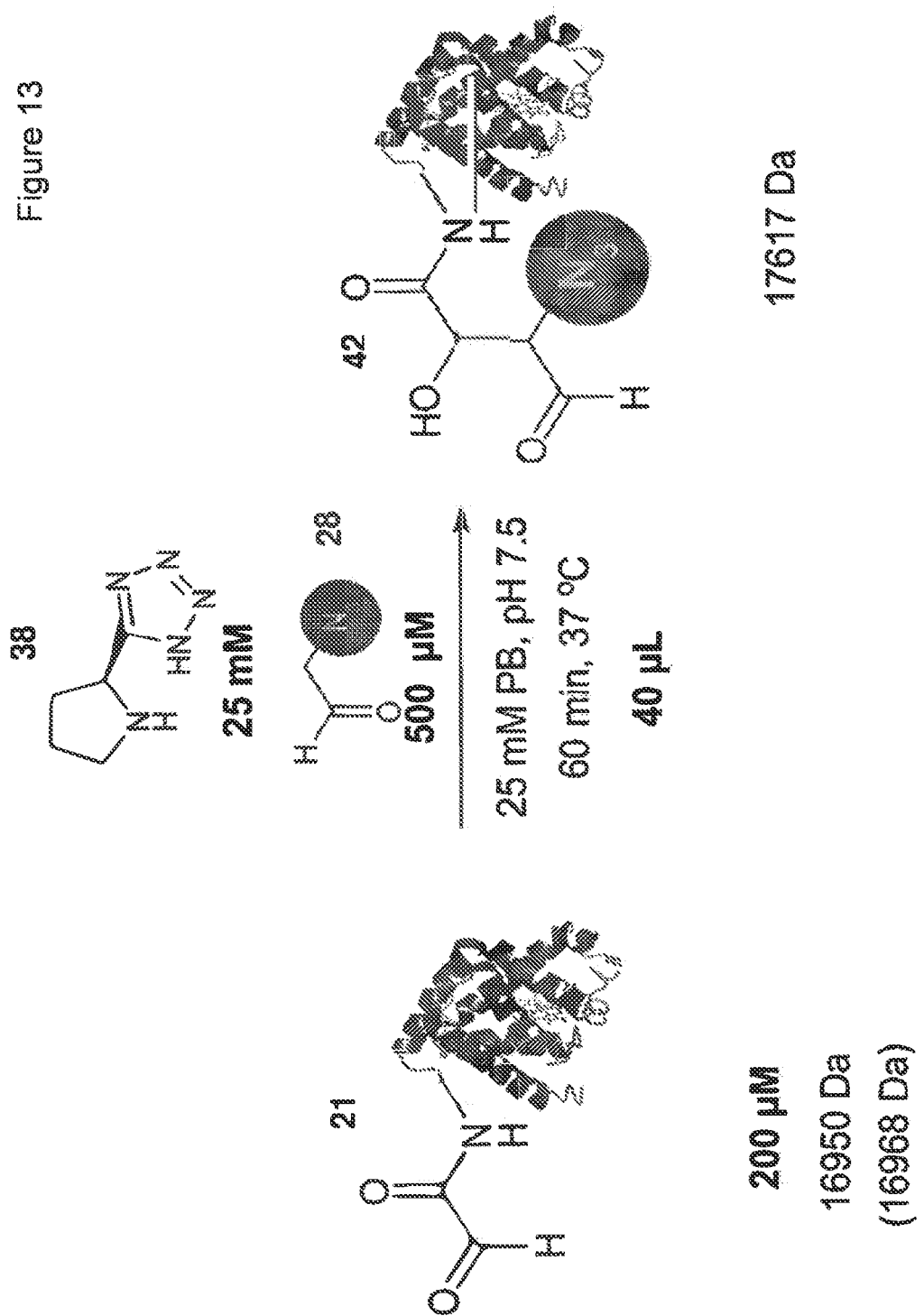
FIG. 13 illustrates an OPAL modification of glyoxyl-myoglobin 21 with the aldehyde donor comprising an azide moiety 28 using proline tetrazole 38 as a catalyst to produce 42. The reaction conditions are shown below the reaction arrow. Molecular weights of the substrate and product are also shown in Da.

Bioconjugation of Azide Group to Glyoxal-Myoglobin by OPAL (See FIG. 13)

An aliquot of glyoxyl-myolgobin 21 (200 μM, 25 μl, 25 mM PB pH 7.5) was charged with an aliquot of proline tetrazole 38 (200 mM, 5 μl, 25 mM PB pH 7.5). The solution was then charged with azide aryl probe 28 (2 mM, 10 μl, 25 mM PB pH 7.5). Following mixing by pipetting, the reaction was allowed to sit at 37° C. for 60 minutes without further agitation. The resulting OPAL product 42 was characterised by LC-MS.

Figure 14:
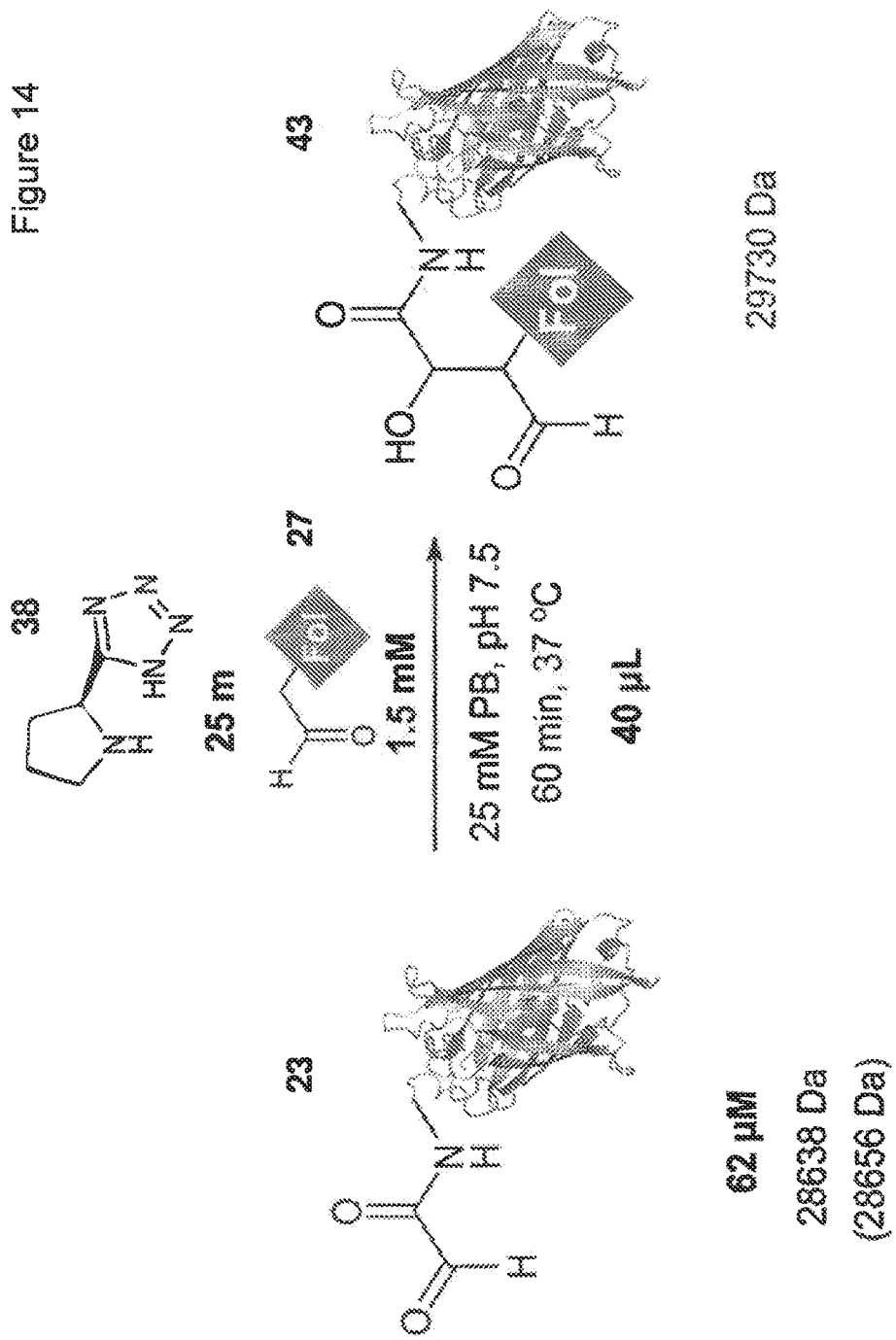
FIG. 14 illustrates an OPAL modification of glyoxyl-GFP 23 with the aldehyde donor comprising a folate moiety 27 using proline tetrazole 38 as a catalyst to produce 43. The reaction conditions are shown below the reaction arrow. Molecular weights of the substrate and product are also shown in Da.

Bioconjugation of Folate to GFP by OPAL (See FIG. 14)

An aliquot of glyoxyl-GFP 23 (100 μM in 25 μL of 25 mM PB pH 7.5) was charged with an aliquot of proline tetrazole 38 (200 mM in 5 μL of 25 mM PB pH 7.5). The solution was then charged with a folate aryl probe 27 (5 mM in 10 μL 25 mM PB pH 7.5). Following mixing by pipetting, the reaction was allowed to sit at 37° C. for 60 minutes without further agitation. The resulting OPAL product 43 was characterised by LC-MS.

Figure 15:
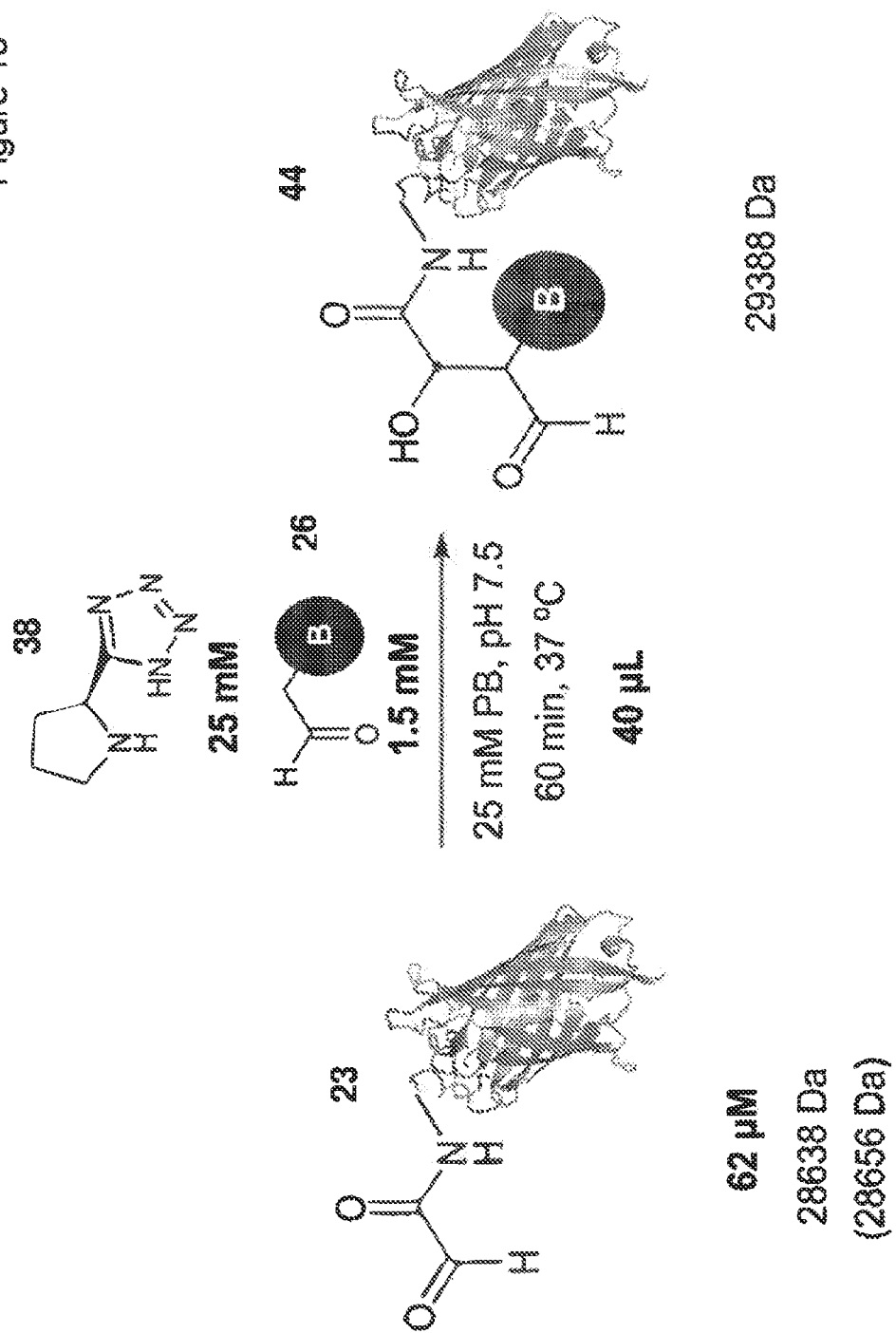
FIG. 15 illustrates an OPAL modification of glyoxyl-GFP 23 with the aldehyde donor comprising a biotin moiety 26 using proline tetrazole 38 as a catalyst to produce 44. The reaction conditions are shown below the reaction arrow. Molecular weights of the substrate and product are also shown in Da.

Bioconjugation of Biotin to GFP by OPAL (See FIG. 15)

An aliquot of 23 (100 μM in 25 μL of 25 mM PB pH 7.5) was charged with an aliquot of proline tetrazole 38 (200 mM in 5 μL of 25 mM PB pH 7.5). The solution was then charged with a biotin aryl probe 26 (2 mM in 10 μL, 25 mM PB pH 7.5). Following mixing by pipetting, the reaction was allowed to sit at 37° C. for 60 minutes without further agitation. The resulting OPAL product 44 was characterised by LC-MS.

Figure 16A:
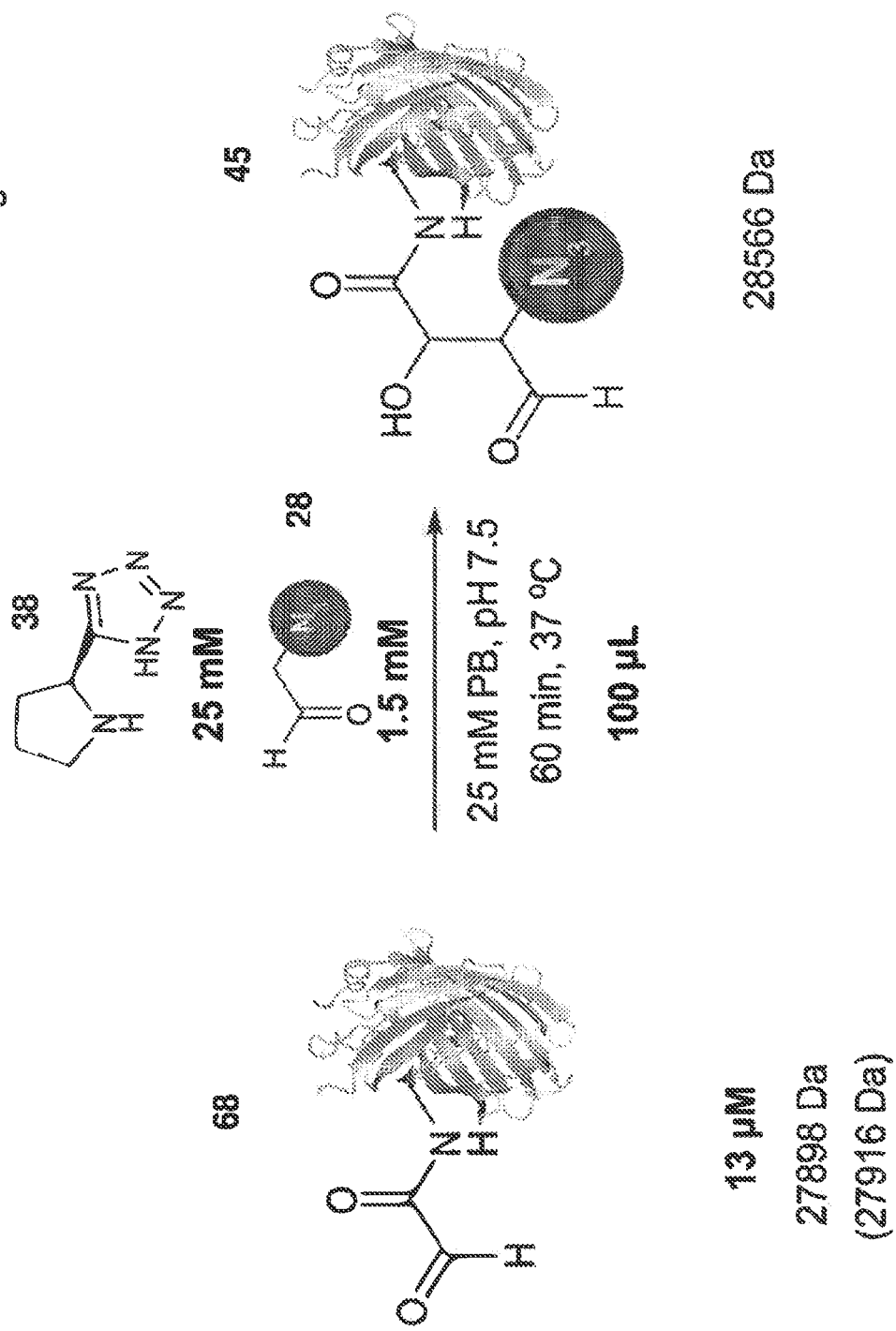
FIGS. 16A and B illustrates an OPAL modification of sfGFP (N150GlyoxylK) 68 with the aldehyde donor comprising an azide moiety 28 using proline tetrazole 38 as a catalyst to produce 45. The reaction conditions are shown below the reaction arrow.
Figure 16B:
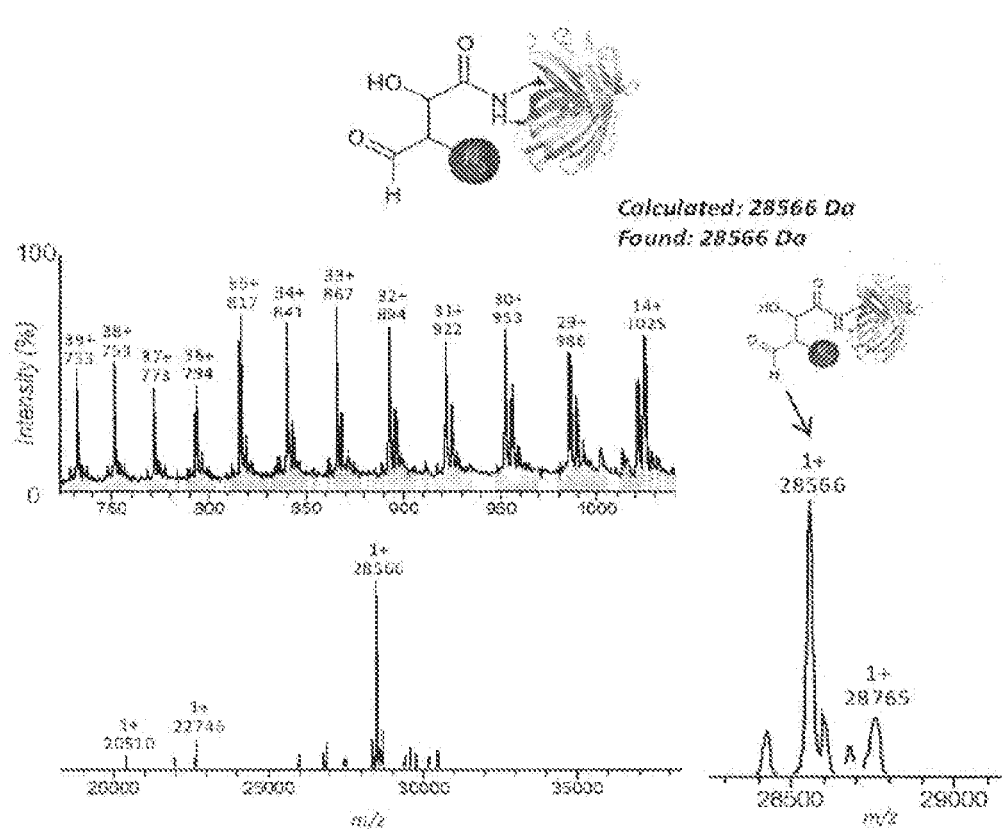

Bioconjugation of Azide Group to sfGFP by OPAL (FIG. 16A and FIG. 16B)

An aliquot of sfGFP(N150GlyoxylK) 68 prepared as described previously (15 μM, 87 μL, MQ H$_2$O) was charged with proline tetrazole 38 (200 mM, 12.5 μL, 25 mM PB pH 7.5) and aryl azide probe 28 (50 mM, 3 μL, MQ H$_2$O). Following mixing by pipetting, the solution was allowed to sit at 37° C. for 60 min without further agitation. Quantitative labelling to internally azide labelled sfGFP 45 was confirmed by ESI-MS analysis. (see FIGS. 16A and B)

Bioconjugation of Butyraldehyde to Glyoxyl-LYRAG Peptide by OPAL

An aliquot of glyoxyl-LYRAG 16A (5 mM in 200 μl of 25 mM PB pH 7.5 (690 μl), and then charged with an aliquot of L-proline 33 solution (200 mM in 100 μl of 25 mM PB pH 7.5) (see Scheme 8 below).

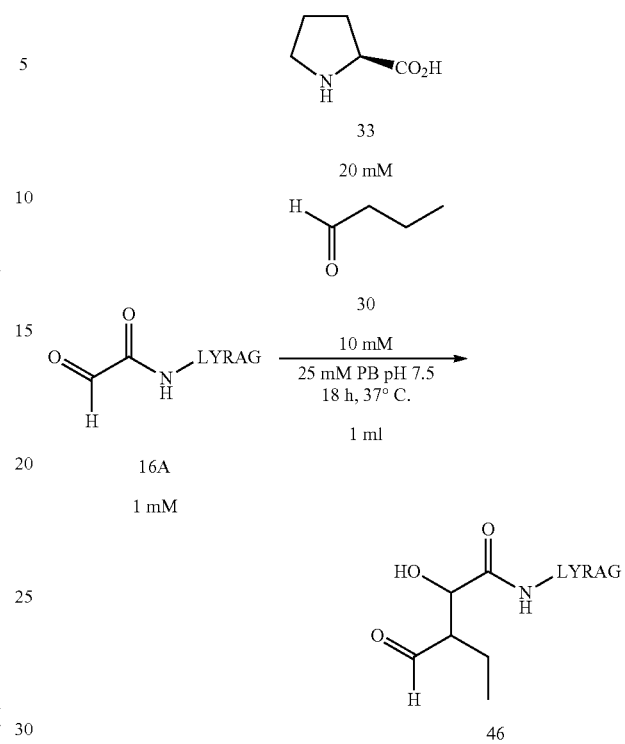

Scheme 8

The solution was then charged with an aliquot of butyraldehyde 30 (1M in 10 μl of 25 mM PB pH 7.5). The reaction was vortexed, and allowed to sit at 37° C. overnight without further agitation. The resulting OPAL product 46 was characterised by LC-MS.

Figure 17:
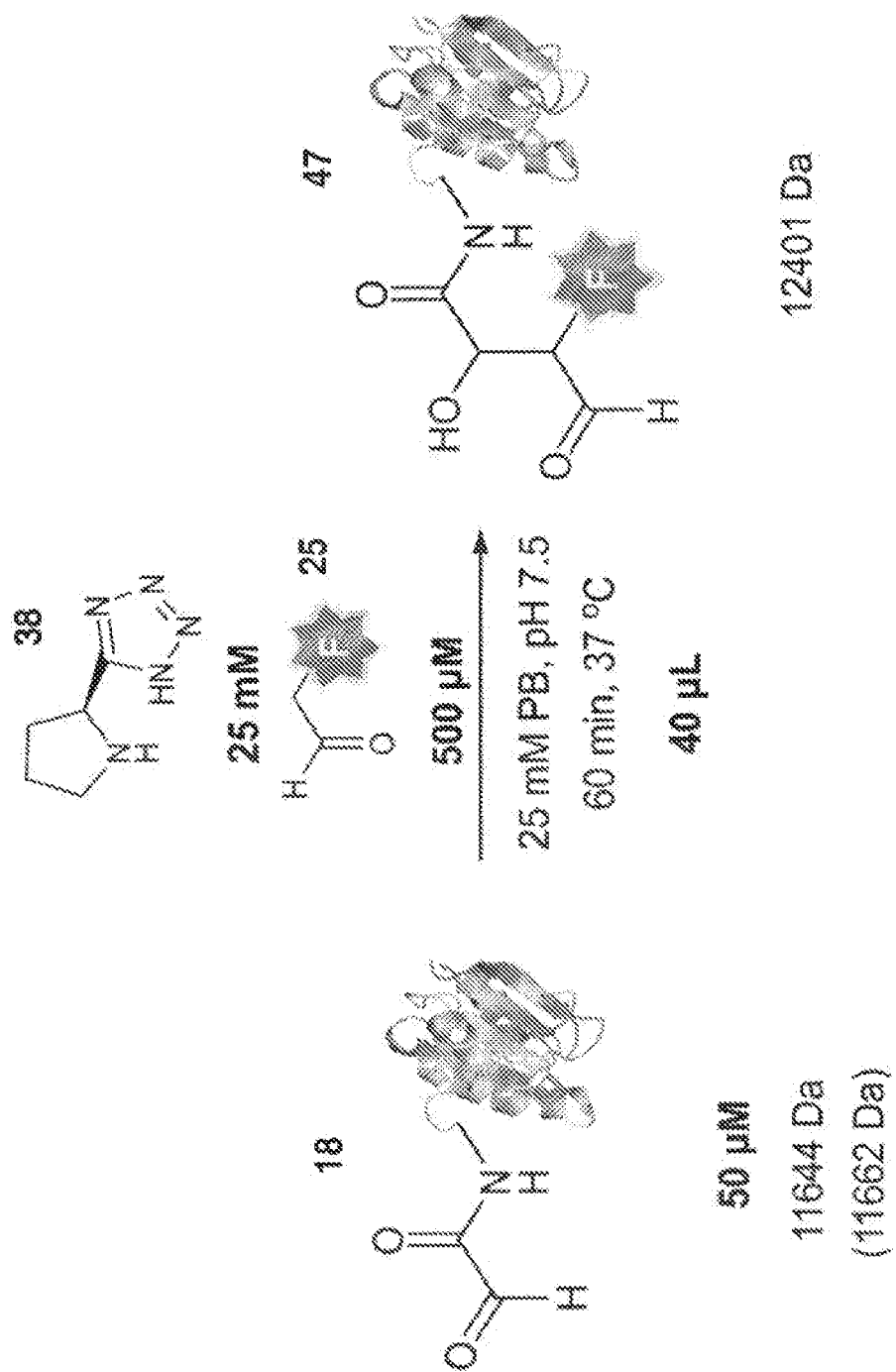
FIG. 17 illustrates an OPAL modification of glyoxyl-thioredoxin 18 with the aldehyde donor comprising a florescent moiety 25 using proline tetrazole 38 as a catalyst to produce 47. The reaction conditions are shown below the reaction arrow. Molecular weights of the substrate and product are also shown in Da.

Bioconjugation of Florescent Group to Thioredoxin by OPAL (See FIG. 17)

An aliquot of glyoxyl-thioredoxin 18 (85 μM in 25 μl of 25 mM PB pH 7.5) was charged with an aliquot of proline tetrazole 38 (200 mM in 5 μl of 25 mM PB pH 7.5). The solution was then charged with fluorescent aryl probe 25 (2 mM in 10 μl of 25 mM PB pH 7.5). Following mixing by pipetting, the reaction was allowed to sit at 37° C. for 60 minutes without further agitation. The resulting OPAL product 47 was characterised by LC-MS.

Figure 18:
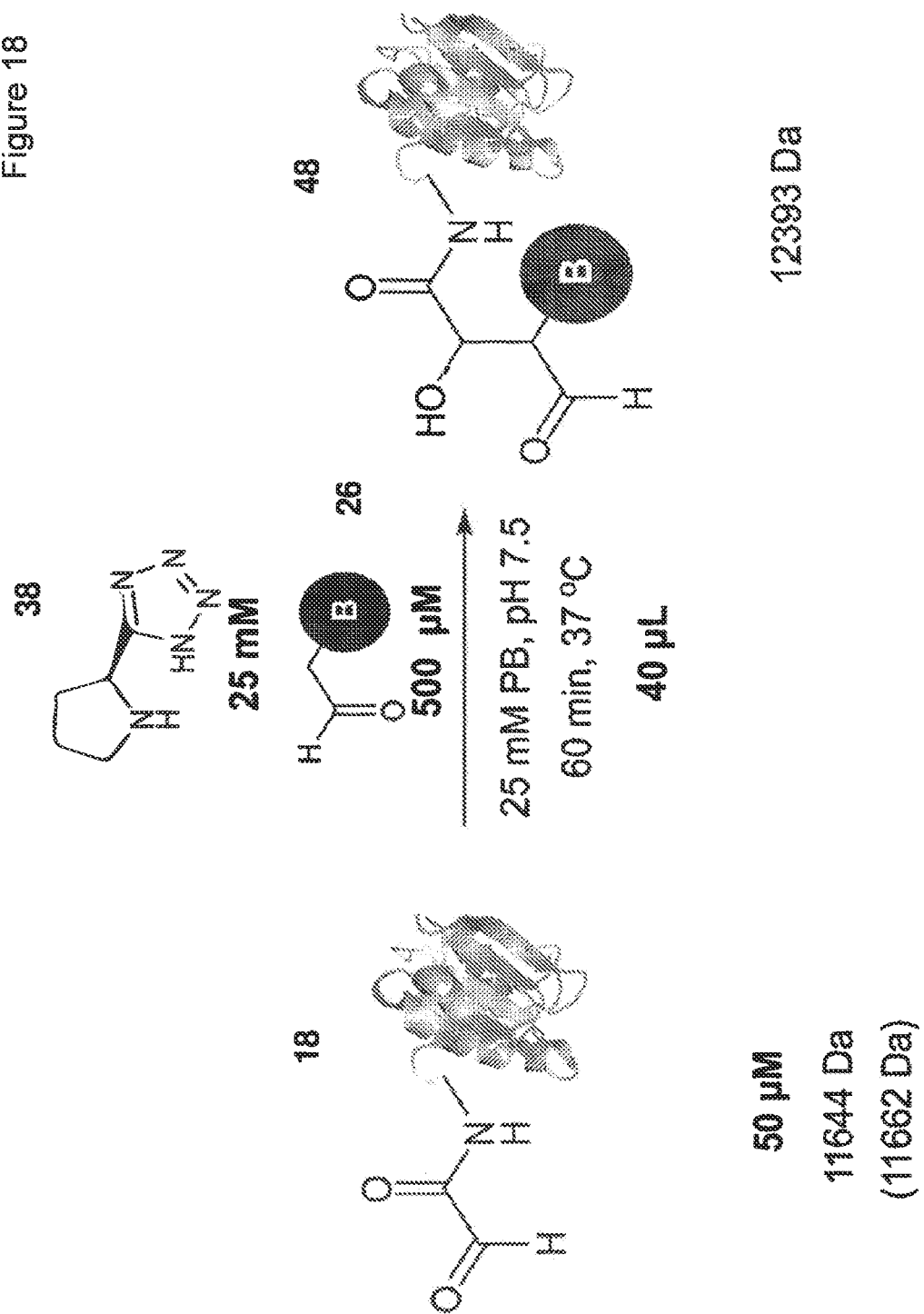
FIG. 18 illustrates an OPAL modification of glyoxyl-thioredoxin 18 with the aldehyde donor comprising a biotin moiety 26 using proline tetrazole 38 as a catalyst to produce 48. The reaction conditions are shown below the reaction arrow. Molecular weights of the substrate and product are also shown in Da.

Bioconjugation of Biotin to Thioredoxin by OPAL (See FIG. 18)

An aliquot of glyoxyl-thioredoxin 18 (85 μM in 25 μl of 25 mM PB pH 7.5) was charged with an aliquot of proline tetrazole 38 (200 mM in 5 μl of 25 mM PB pH 7.5). The solution was then charged with biotin aryl probe 26 (2 mM in 10 μl of 25 mM PB pH 7.5). Following mixing by pipetting, the reaction was allowed to sit at 37° C. for 60 minutes without further agitation. The resulting OPAL product 48 was characterised by LC-MS.

Figure 19:
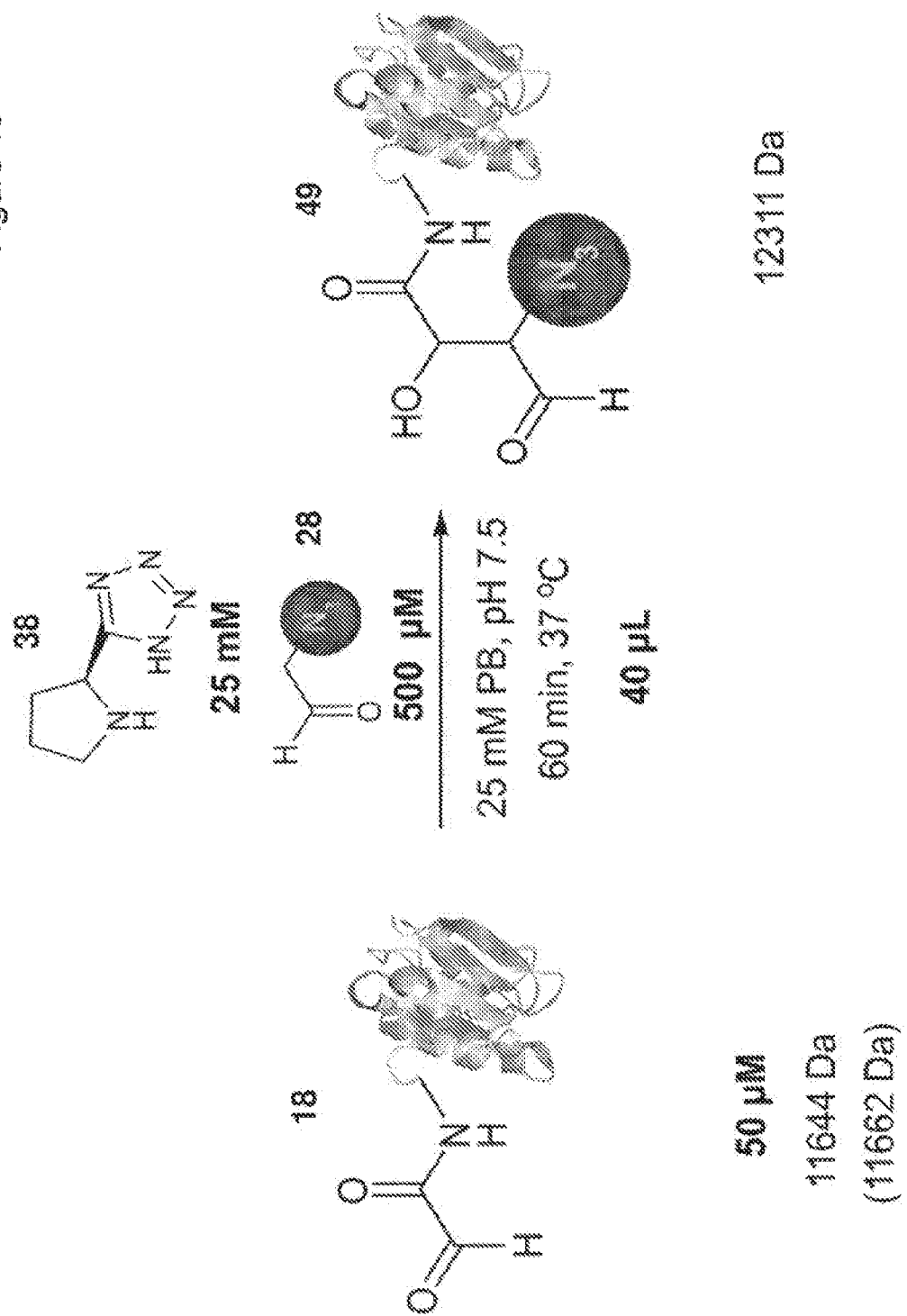
FIG. 19 illustrates an OPAL modification of glyoxyl-thioredoxin 18 with the aldehyde donor comprising an azide moiety 28 using proline tetrazole 38 as a catalyst to produce 49. The reaction conditions are shown below the reaction arrow. Molecular weights of the substrate and product are also shown in Da.

Bioconjugation of Azide Group to Thioredoxin by OPAL (See FIG. 19)

An aliquot of glyoxyl-thioredoxin 18 (85 μM in 25 μl of 25 mM PB pH 7.5) was charged with an aliquot of proline tetrazole 38 (200 mM in 5 μl of 25 mM PB pH 7.5). The solution was then charged with azide aryl probe (2 mM in 10 μl of 25 mM PB pH 7.5). Following mixing by pipetting, the reaction was allowed to sit at 37° C. for 60 minutes without further agitation. The resulting OPAL product 49 was characterised by LC-MS.

Testing Hydrolytic Stability of Azide Labelled Thioredoxin

An aliquot of azide labelled thioredoxin 49 (25 μM, 25 μl, 25 mM PB pH 7.5) was incubated at 37° C. over the course of 72 hours. LC-MS data of the sample was collected at 24-hour intervals. No hydrolysis of azide labelled thioredoxin 49 to give glyoxyl-thioredoxin 18 was observed as judged by LC-MS, highlighting the hydrolytic stability of the OPAL products.

Screening of Aniline Catalysts for Aniline Organocatalyst-Mediated Oxime Ligation of Aldol-LYRAG An aliquot of α-phenyl-s-hydroxy aldehyde-LYRAG 50 (5 mM, 10 μl, H$_2$O) was charged with an aliquot of buffer (0.1 M NaOAc pH 4.5 or 0.2 M PB pH 7.0, 439.5 μl), and then charged with O-benzylhydroxylamine 51 (0.5 μl) (see Scheme 9 below). The solution as then charged with an aniline catalyst 56-59 (1M, 50 μl, DMSO). The reaction was vortexed, and allowed to sit at 37° C. for 18 hours without further agitation. Conversion to the product 52 was confirmed by LC-MS analysis.

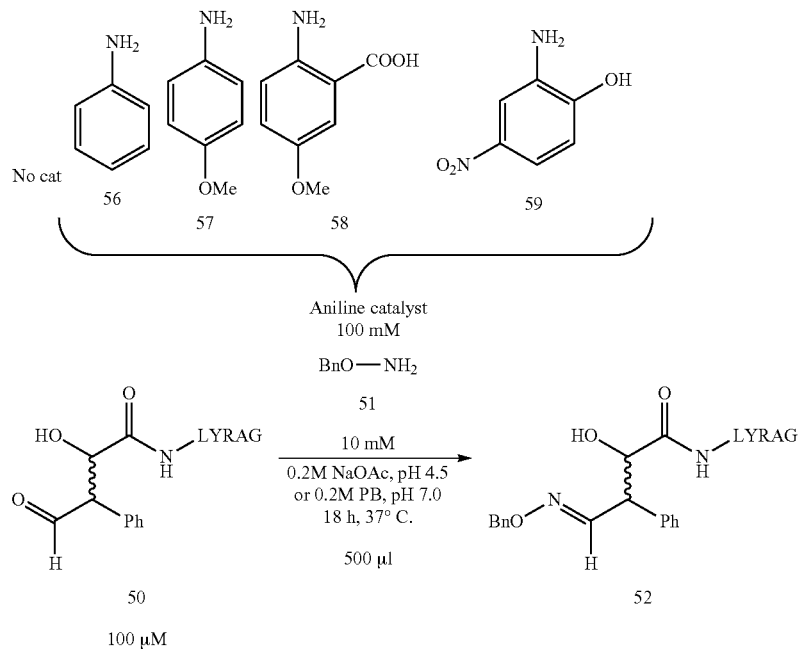

Scheme 9

Figure 20:
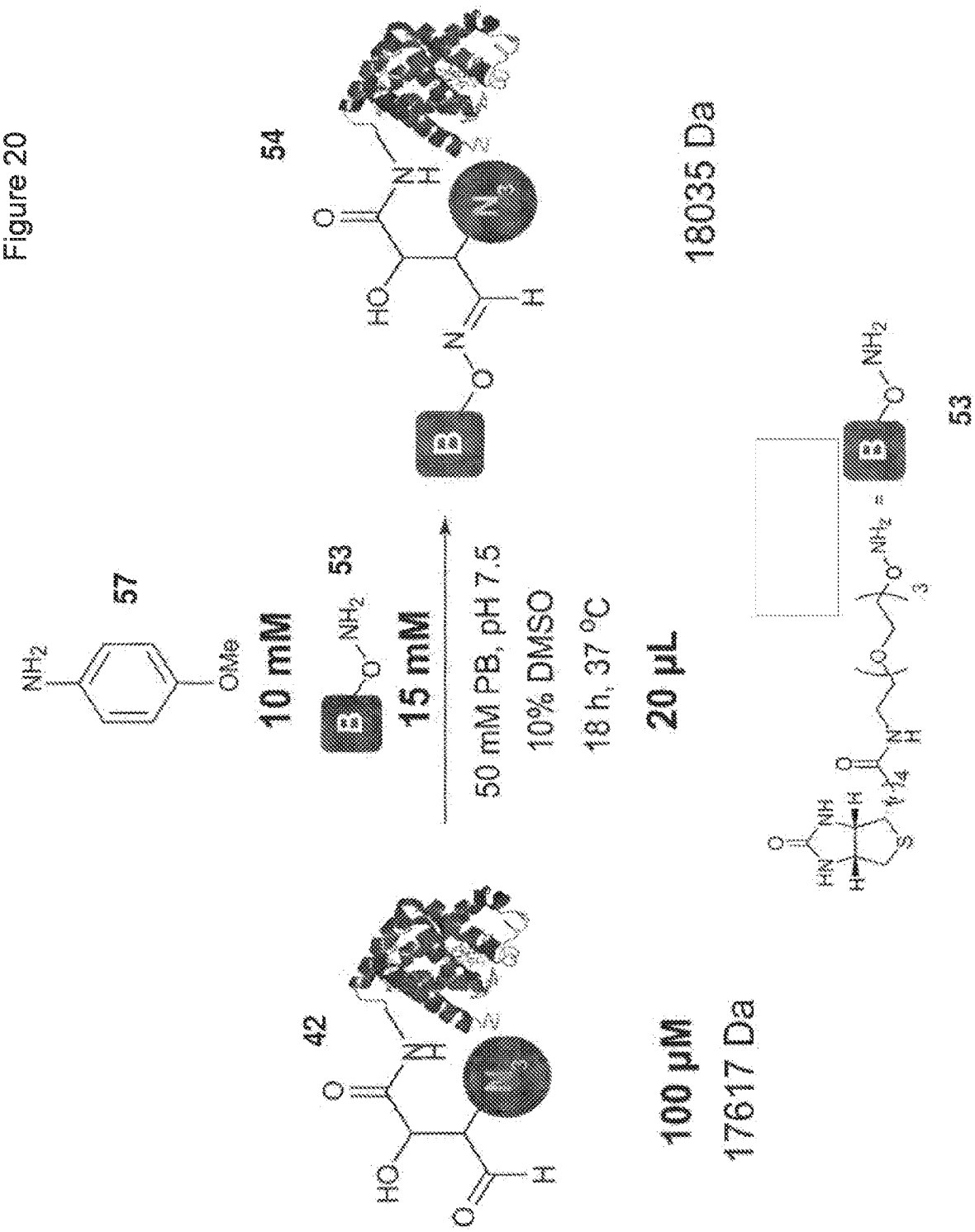
FIG. 20 illustrates an aniline organocatalyst-mediated oxime ligation reaction (also referred to as an anilinium/protein (AnPro) activation) using myoglobin conjugated to a functional group comprising an azide moiety 42 as a substrate with the aminooxy biotin donor molecule 53 using aniline catalyst 57 to produce the dual conjugated product 54. The reaction conditions are shown below the reaction arrow as well as the structure of 53.

Synthesis of Azide Labelled, Biotinylated Myoglobin (FIG. 20)

An aliquot of azide labelled myoglobin 42 prepared as described earlier (200 μM, 10 μl, 5 mM PB pH 7.5) was charged with 0.2 M PB pH 7.5 (3.8 μl) aminooxy biotin 53 (250 mM, 1.2 μl, 0.2 M PB pH 7.5, pH adjusted to pH 7.0 using 1M NaOH). The solution was then charged with p-anisidine 57 (100 mM, 0.4 μl, DMSO,) and H$_2$O (4.6 μl). Following mixing by pipetting, the reaction was allowed to sit at 37° C. for 42 hours without further agitation. Conversion to the product 54 was confirmed by LC-MS analysis.

Figure 21:
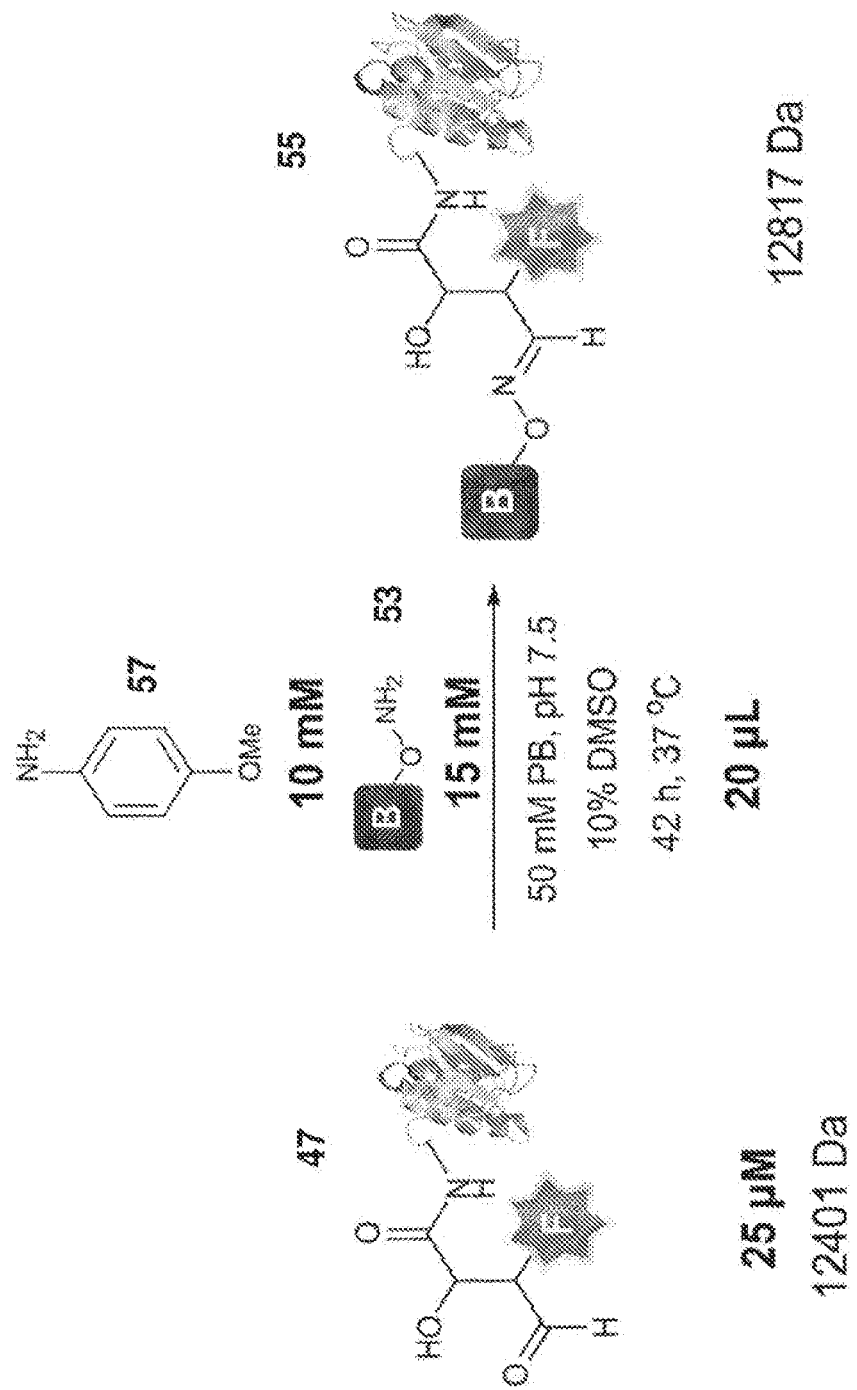
FIG. 21 illustrates an aniline organocatalyst-mediated oxime ligation reaction using thioredoxin conjugated to a functional group comprising a fluorescent moiety 47 as a substrate with the aminooxy biotin donor molecule 53 using aniline catalyst 57 to produce the dual conjugated product 55. The reaction conditions are shown below the reaction arrow.

Synthesis of Fluorescently Labelled, Biotinylated Thioredoxin (FIG. 21)

An aliquot of fluorescently labelled thioredoxin 47 prepared as described earlier (50 μM, 10 μl, 5 mM PB pH 7.5) was charged with 0.2 M PB pH 7.5 (3.8 μl) aminooxy biotin 53 (250 mM, 1.2 μl, 0.2 M PB pH 7.5, pH adjusted to pH 7.0 using 1M NaOH). The solution was then charged with p-anisidine 57 (100 mM, 0.4 μl, DMSO,) and H$_2$O (4.6 μl). Following mixing by pipetting, the reaction was allowed to sit at 37° C. for 42 hours without further agitation. Conversion to the product 55 was confirmed by LC-MS analysis.

Screening Aniline Catalysts for Retro-Aldol Mediated Decomposition of Aldol-LYRAG An aliquot of aldol-LYRAG 50 (5 mM, 10 μl, H$_2$O) was charged with an aliquot of buffer (0.2 M NaOAc 4.5, or 0.2 M PB, pH 7.0, 440 μl). The solution was then charged with an aniline catalyst (1M in 50 μl DMSO) selected from compounds 56, 57, 58 and 59 as shown in Scheme 10 below. The reaction was vortexed, and allowed to sit at 37° C. for 18 hours without further agitation. Conversion to the product 16A/16B was confirmed by LC-MS analysis.

Scheme 10

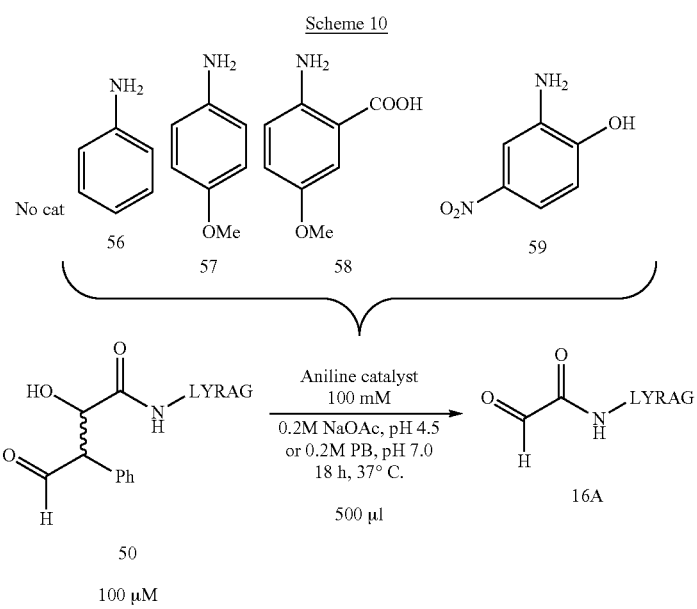

Screening of Buffer Conditions for Retro-Aldol Mediated Decomposition of Aldol-LYRAG An aliquot of α-phenyl-β-hydroxy aldehyde-LYRAG 50 (5 mM in 10 μl of $H_2O$) was charged with an aliquot of buffer (0.2 M NaOAc 4.5, or 0.2 M PB, pH 7.0, 440 μl). The solution was then charged with p-anisidine catalyst 57 (1M, 50 μl, DMSO). The reaction was vortexed, and allowed to sit at 37° C. for 18 hours without further agitation (Scheme 11). Conversion to the product 16A/16B was confirmed by LC-MS analysis.

Scheme 11

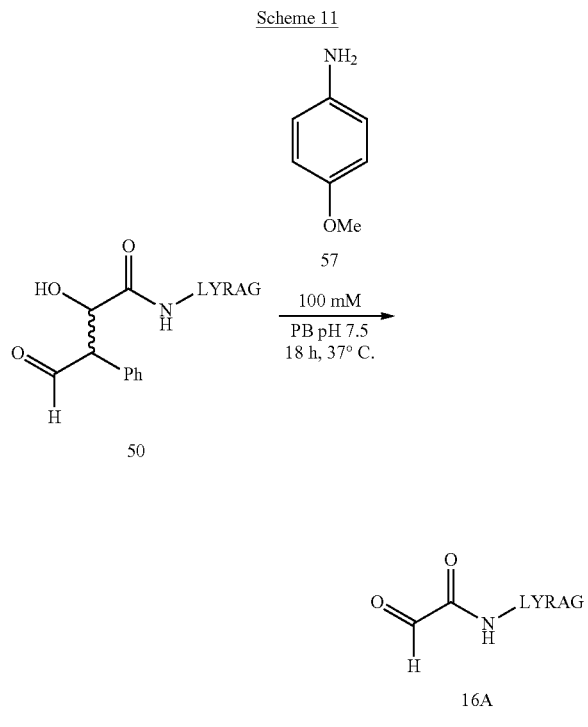

Figure 22:
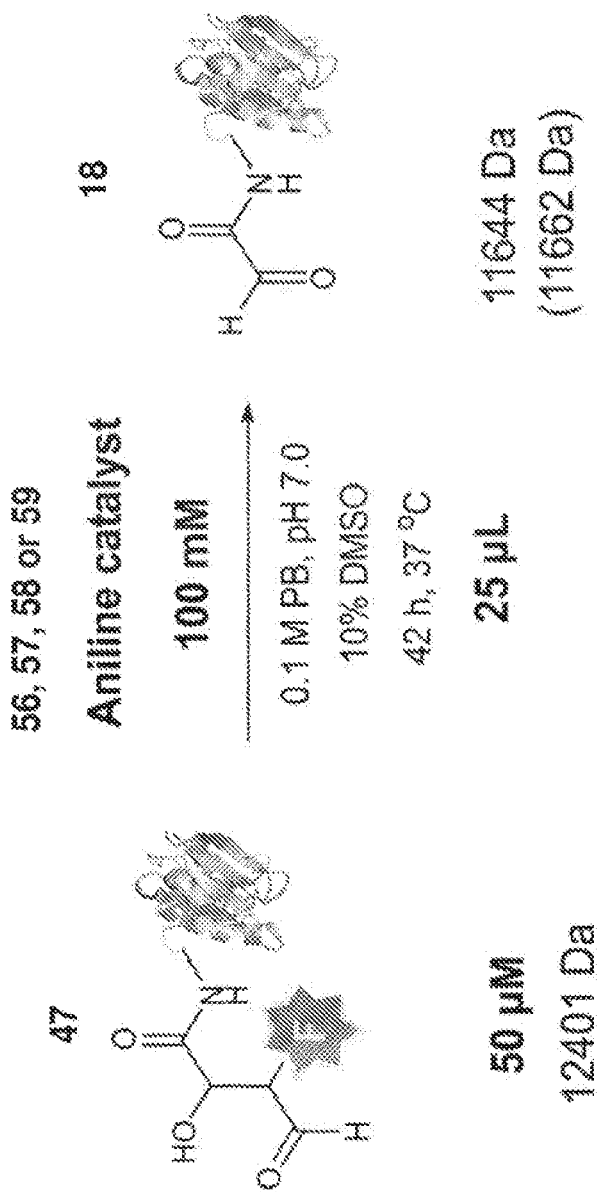
FIG. 22 illustrates a retro-aldol reaction using thioredoxin conjugated to a functional group comprising a fluorescent moiety 47 as a substrate and an aniline catalyst selected from compounds 56, 57, 58, and 59 to remove the conjugated functional group comprising a florescent moiety and produce glyoxyl-thioredoxin 18. The reaction conditions are shown below the reaction arrow.

Screening Aniline Catalysts for Retro-Aldol Mediated Decomposition of Fluorescently Labelled Thioredoxin (FIG. 22)

An aliquot of fluorescently labelled thioredoxin 47 (50 μM, 12.5 μl, 0.1 M PB pH 7.0) was charged with 0.1 M PB pH 7.0 (10 μl). The solution was then charged with either DMSO (2.5 μl), or aniline catalyst 56-59 (1M, 2.5 μl, DMSO). Following mixing by pipetting, the reaction was allowed to sit at 37° C. for 42 hours without further agitation. Conversion to the product 18 was confirmed by LC-MS analysis.

Results and Discussion

Incorporation of Aldehyde Handle(s)

Incorporation of Thiazolidine Lysine (ThzK) & Uncaging of Aldehyde Handle

The mutants were each individually expressed with the supplementation of 2-OMe at 1.5 mM in growth media and the green fluorescence of the harvested cell pellets confirmed the presence of full-length protein, demonstrating that ThzK can be encoded by the *M. mazei* pyrrolysine tRNA-RS pair. Following nickel affinity purification of the cell lysate, both mutants Ser-GFP(Y39ThzK) 2B and sfGFP (N150ThzK) 2a could be isolated and purity confirmed by SDS-PAGE and ESI-FTICR-MS (data not shown).

With expression succeeding, 2B was selected as a test system to screen reagents for decaging to yield Ser-GFP (Y39GyoxylK) 23

9-12 were trialled at 37° C. at pH 7.4 in order to maintain biocompatibility over a range of concentrations and time intervals (Table 1). These reagents are a mixture of palladium(0) and palladium(II). At 100 equivalents, addition of 9 and 11 led to immediate denaturation and eventual precipitation, although some decaging was observed with 11. 10 was found to be inert, neither denaturing nor decaging.

Success emerged with 12, with complete decaging observed after 48 hours. Condition optimisation led to completion of decaging within 24 hours. Curiously, under these conditions 23 appeared to exist predominantly as the aldehyde, whilst glyoxyl aldehydes in aqueous conditions generally exist as the hydrate (+18 Da) form. The same conditions were then repeated on proteins 68. This decaging procedure was be repeated on 2A to yield sfGFP (N5GlyoxylK) 68 with complete conversion as well, with this protein, the decaged glyoxyl exists mostly as the hydrated form rather than the aldehyde form (3:1). The observation that 11 denatured GFP seemed unusual given its successful use for other types of decaging with GFP. Screening showed that at concentrations greater than 0.5 mM, 11 will denature GFP, but not at lower concentrations. Hence further screening was carried out using lower equivalents of 11 at the same concentration of 14 and full decaging could be observed within one hour with just one equivalent of 11, whilst use of 12 under the same conditions led to nodetectable decaging. One equivalent of 11 strikes the balance between minimal protein denaturing and maximum extent of decaging, as lower equivalents result in poorer conversions.

TABLE 1

A) Reagents screened to decage protein thiazolidine to afford protein aldehyde/hydrate.
B) approximately 40% decaging seen at 6 hour 12 and complete decaging seen within 1 hour using 11

| Pd source | Equiv. [Pd] | t/h | % conversion | GFP fluorescence |
|---|---|---|---|---|
| 9 | 100 | 6 | — | Yes |
| 9 | 100 | 24 | — | Yes |
| 10 | 100 | 6 | 0 | No |
| 10 | 100 | 24 | 0 | No |
| 11 | 100 | 6 | 30 | No |
| 11 | 100 | 24 | — | No |
| 11 | 1 | 1 | 100 | Yes |
| 12 | 1 | 1 | 40 | Yes |
| 12 | 100 | 6 | 40 | Yes |
| 12 | 200 | 6 | 40 | Yes |
| 12 | 100 | 24 | 80 | Yes |
| 12 | 100 | 68 | 90 | Yes |
| 12 | 100 | 40 | 100 | Yes |

As further confirmation of the exposed aldehyde reactivity, aniline-catalysed oxime ligation was performed upon the protein glyoxyl species 23/68, uncaged by both palladium reagents, to form oximes using aminooxy biotin probe 53. When decaged by 12, even over 24 h 23 barely converted to the oxime product, although the aniline imine was formed in roughly 50% conversion. 70% conversion to the oxime product was observed using 68 decaged by 12. Greater conversions could be seen from protein glyoxyls decaged by 11, with both proteins undergoing complete oxime ligation in 24 hours (Table 2).

TABLE 2

| Protein | [Pd] decaging reagent | % oxime conversion |
|---|---|---|
| 23 | 12 | <5 |
| 68 | 12 | 70 |
| 23 | 11 | 100 |
| 68 | 11 | 100 |

Figure 23:
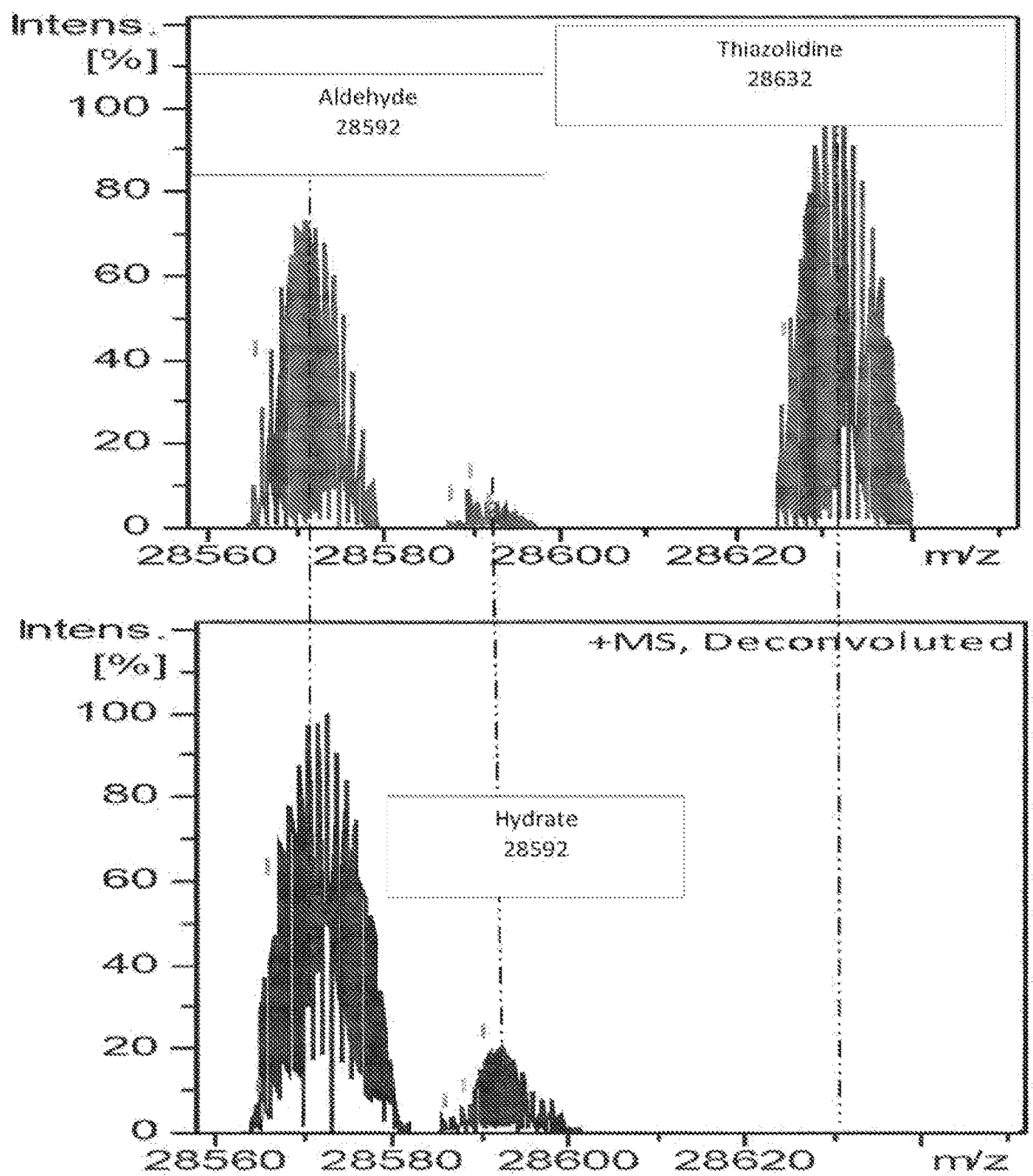
FIG. 23 shows deconvoluted ESI-FTICR-MS spectra of GFP(Y39GlyoxylK) 13A (aldehyde) and 13B (hydrate). The top panel shows a spectrum collected at 6 hours after the start of the reaction and the bottom panel shows a spectrum collected at 36 hours. It can be seen from the spectra that there is an increased level of consumption of the thiazolidine group and formation of GFP(Y39GlyoxylK) 13A (and 13B) over time.

In initial investigations, compounds 10 and 12 did not lead to GFP unfolding, with fluorescence visible at all times. Reagent 12 had increasing levels of conversion with increasing reaction time. Increases in the concentration of palladium had no observable effect on conversion. Without being bound by theory, this may be due to the limited solubility of the palladium in aqueous solution (6% DMSO co-solvent), with undissolved palladium exerting little effect on the thiazolidine. Following decaging. GFP(Y39GlyoxylK) 13A could be seen clearly by ESI-FTICR-MS (FIG. 23), predominantly in the aldehyde form 13A but with some hydrate 13B visible, and in sufficient quantities to carry forward to further experiments. Conversion of 2B to 13A/B was determined to be >95% by ESI-MS analysis after 24 h under these conditions.

Upon further investigation however, using altered reactants and concentrations of palladium catalyst it was noted that 90 to 95% decaging of GFP proteins could be achieved using palladium catalyst 11 at stoichiometric concentrations. The use of palladium catalyst 11 provided 90 to 95% decaging within 1 hour, in comparison to 24 hours as was seen for palladium catalyst 12. The conditions used also remove the need for a centrifugation step to remove quenched catalyst.

Figure 24:
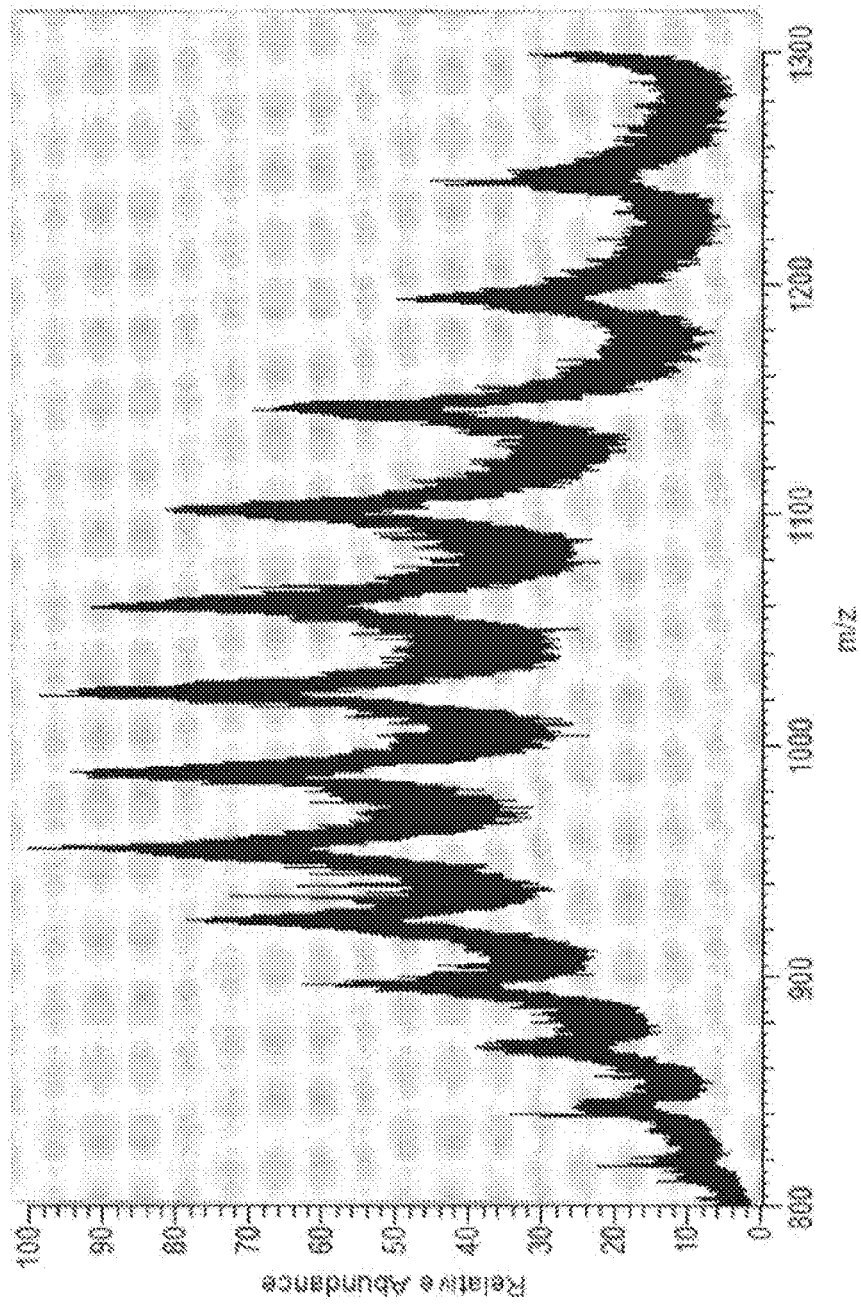
FIG. 24 shows raw ESI-Orbitrap-MS spectrum of GFP (Y39ThzK) 8 that has undergone a sodium periodate mediated serine cleavage reaction.
Figure 25:
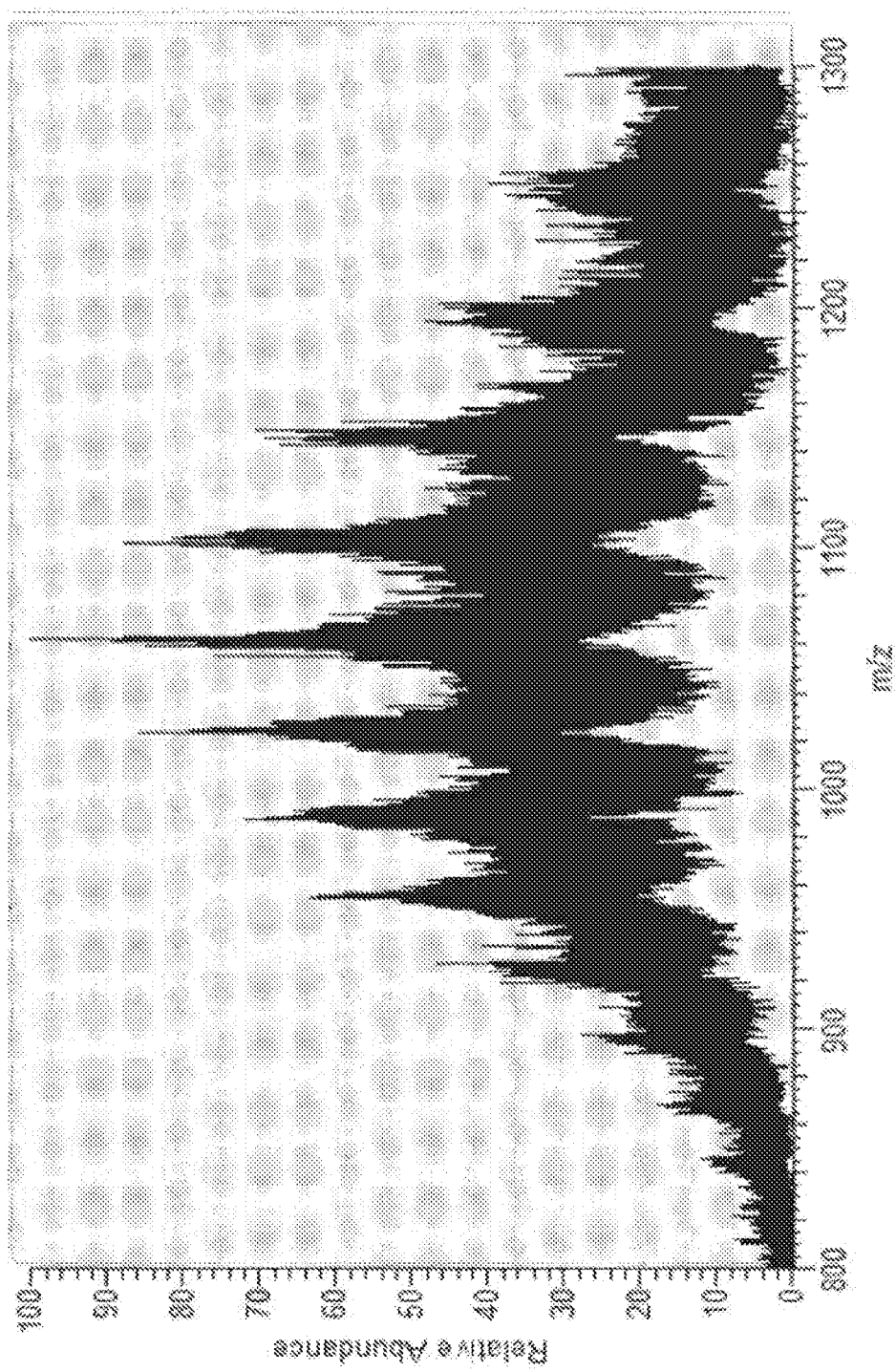
FIG. 25 shows raw ESI-Orbitrap-MS spectrum of Ser-GFP(Y39CycloOK) 14 that has undergone a sodium periodate mediated serine cleavage reaction. The clear and defined peaks can be assigned to a mixture of the corresponding aldehyde and hydrate species.
Figure 26:
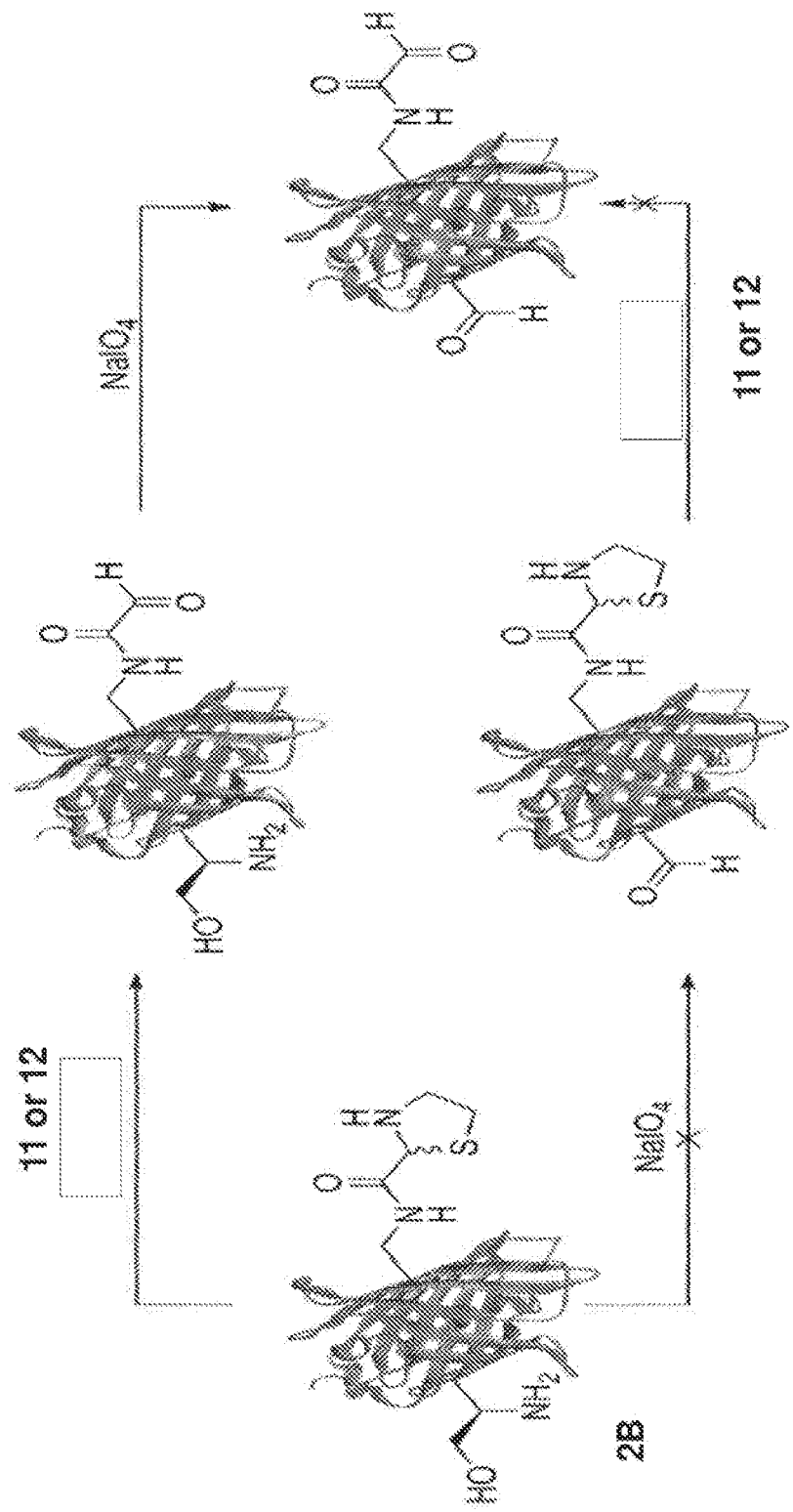
FIG. 26 illustrates a dual aldehyde decaging and modification process. It can be seen that for optimal converison palladium-mediated decaging may be performed before periodate-mediated cleavage to reduce unwanted oxidation of the thiazolidine, likely preventing palladium-mediated decaging and inhibiting the efficiency of serine cleavage.
Figure 28:
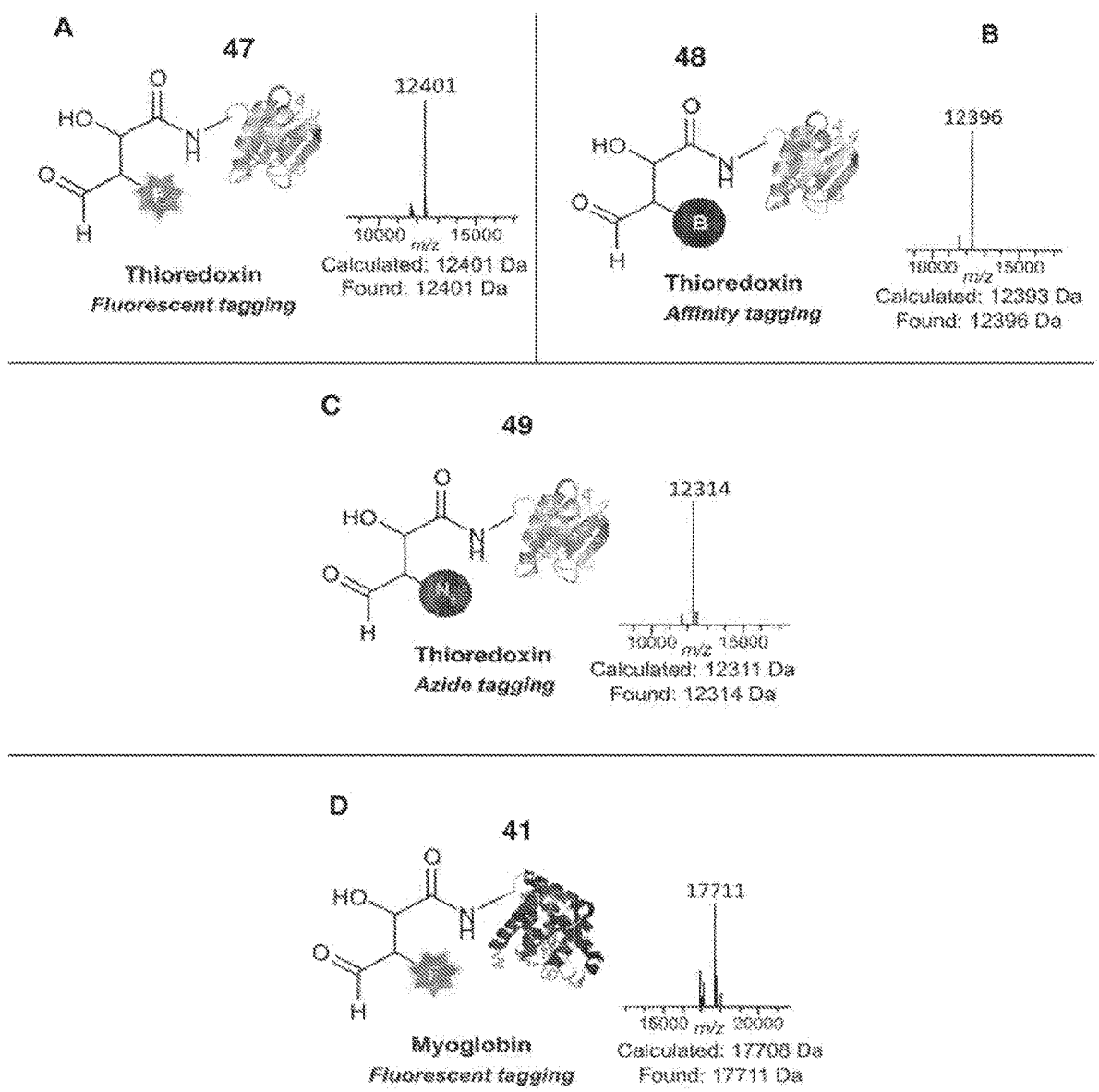
FIG. 28 illustrates the structures of protein conjugates 47 (A), 48 (B), 49 (C) and 41 (D) formed by OPAL reactions. Shown next to each structure is the LC-MS spectra for each corresponding species with the calculated and actual molecular weights indicated below each spectrum.

The orthogonality of the two aldehyde precursors, the thiazolidine lysine and the N-terminal serine, was tested. The previous MS decaging results obtained for 2B demonstrate clearly that the serine residue, and indeed all other residues, are unaffected by palladium decaging. However, although no GFP fluorescence was quenched, broadening of peaks in the charge ladder suggests the presence of multiple species beyond the expected aldehyde 13A and hydrate 13B (FIG. 24), was observed when 2B was subjected to $NaOI_4$ oxidation prior to decaging. As a reference, Ser-GFP (Y39CycloOK) 14 (an analogue of 2B) was prepared using commercially available 2-cyclooctynyloxycarbonyl lysine in the same manner that ThzK was inserted into 2, with the non-canonical amino acid (2-cyclooctynyloxycarbonyl lysine) being inert to oxidation. Upon undergoing $NaOI_4$-mediated serine cleavage of 2B, clear and defined peaks can be seen in the ESI-Orbitrap-MS spectrum (FIG. 25), which can be assigned to a mixture of the corresponding aldehyde and hydrate. Some of the additional peaks broadening the signals in the oxidation of 2B can be assigned as 2B+16 m/z, implying sulfoxidation on the thiazolidine. Sulfoxidation of thiazolidines using $NaOI_4$ in aqueous conditions has been well documented. The consequence of this observation is that any dual modification strategy taking advantage of both aldehyde precursors selectively may be optimally achieved through palladium-decage and modification the internal aldehyde first, prior to oxidation of the N-terminal serine residue (FIG. 26).

In conclusion, a new way to uncage a genetically encoded aldehyde precursor has been demonstrated, permitting access to internally-modified proteins without the need for a recognition sequence. This method also provides a decaging reaction that can be performed at approximately neutral or biological pH and does not cause degradation of the protein target.

Incorporation of Aldehyde Handle(s) into Proteins and Peptides

In addition to Pd decaging of ThzK unnatural amino acids, glyoxyl moieties were also installed into proteins using sing sodium periodate oxidation of N-terminal serine, or transamination of N-terminal glycine. Table 3 shows the comparable percentage conversion of the proteins to the glyoxyll form by different methods and also indicates the amino acid modified. Also shown is the molecular weight (MW) of the original protein and the MW of the modified protein.

TABLE 3

Conversion % for incorporation of glyoxyl moieties into proteins

| Protein | Target Residue | Conversion Percentage (by EC-MS) | MW (Da) | MW after MW of product (Da) |
|---|---|---|---|---|
| Thioredoxin | Serine 1 | >95% | 11675 | 11644 |
| Horse heart Myoglobin | Glycine 1 | >95% | 16951 | 16950 |
| SLYRAG | Serine 1 | >95% | — | — |
| GFP | Serine 1 | >95% | 28669 | 28638 |
| GFP | Y39ThzK | 90% | 28634 | 28575 |
| sfGFP | N150ThzK | >95% | 27916 | 27916 |

It can be seen from the results in Table 3 that conversion to the Glyoxyl form is highly efficient whether performed by insertion of ThzK or by sodium periodate oxidation, or transamination.

Bioconjugation of Functional Groups

To establish conditions for the OPAL reaction, studies were initially performed on two protein systems, horse heart myoglobin and disulfide bond containing thioredoxin, both bearing non-enolisable α-oxo-aldehydes as produced as previously described. Preliminary ligations in phosphate buffer (PB) afforded full conversion to the desired β-hydroxy protein aldehydes within 6 hours at neutral pH with 100 mM L-proline 33 organocatalyst, using butyraldehyde as an aldehyde donor (FIG. 11). Notably, only one aldol modification occurred, confirming the stability of the β-hydroxy aldehyde motif to further aldol reactions, and no transformation was observed in the absence of organocatalyst. Additionally, trypsin digest and LC-MS/MS analysis of the resulting peptide fragments confirmed the site-selective nature of the OPAL), and UV/Vis spectroscopic measurements of the haem group in the modified myoglobin confirmed that the protein's tertiary structure had not been compromised.

Encouraged by the biological compatibility and site selectivity in these preliminary ligations, attention next turned to optimizing the OPAL by focusing on the choice of organocatalyst and aldehyde donor species. Initially a panel of secondary amines (33-38) were screened to investigate their ability to catalyse the ligation using a model peptide substrate α-oxo-aldehyde-LYRAG 16A and acetaldehyde 32, and second order rate constants were obtained for each catalyst at 1, 10, and 25 mM loadings (Table 4).

The rate constants differed depending on the choice of catalyst, with a 60-fold variance across the panel with tetrazole 38 exhibiting the highest rate constants, with similar reactivity correlations evident using a protein substrate. Further peptide screens also demonstrated that the nature of the α-carbon substituent of the aldehyde donor could significantly affect the rate of ligation, with phenyl acetylaldehyde, a donor bearing an aryl substituent, participating in the reaction with L-proline 33 and tetrazole 38 with at least a 240-fold increase in rate over aldehyde donors bearing alkyl substituents. Overall, the maximum rate constant measured for the ligation was ~24 $M^{-1}$ $s^{-1}$ using tetrazole 38 which is comparable to the fastest aldehyde ligations reported in the prior art, demonstrating that judicious choice of organocatalyst as well as donor species is important for achieving optimal rates of ligation.

Figure 29:
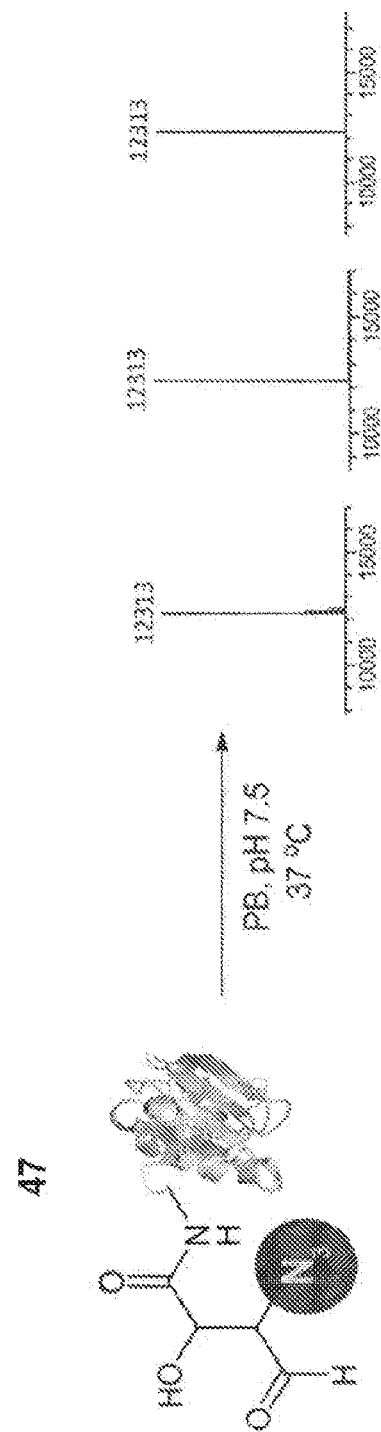
FIG. 29 illustrates the stability of the protein conjugates formed by the OPAL reaction. Conjugate 47 was incubated in PB at pH 7.5 at 37° C. for 72 hours. Shown to the left of the figure is spectra collected at 24, 48 and 72 hours. No reduction in the peak corresponding to conjugate 47 can be seen, indicating that the conjugate remains stable over time in biologically relevant conditions.

Having established both the increased reactivity of aldehyde donors bearing aryl substituents and tetrazole as the most effective organocatalyst for the OPAL, the scope of these optimized conditions was investigated in the site-selective bioconjugation of a range of proteins using functionalized α-aryl aldehyde donors. Guided by a desire to simplify protein chemical modification procedures, a practical synthetic route to access α-aryl substituted aldehyde donors bearing functional probes, such as a fluorescent moiety, a biotin moiety, a bioorthogonal azide moiety, and a folate targeting moiety were used. Proteins including thioredoxin, myoglobin and green fluorescent protein (GFP), bearing α-oxo-aldehydes at their N-termini, were all modified in uniformly excellent conversion within 60 min using 5-10 equivalents of aldehyde donor. The data also shows (FIG. 27C) that hindered internal α-oxo-aldehydes installed using unnatural amino acid mutagenesis could also be rapidly modified at neutral pH using the OPAL, and proteins bearing additional unnatural amino acid handles such as bioorthogonal strained alkynes were also compatible with the OPAL conditions, using GFP as the protein scaffold in both these instances. Notably, in all cases no modification was observed on proteins that did not bear the required aldehyde functionality, and OPAL products showed no degradation after incubation in 25 mM PB pH 7.5 for at least 72 hours at 37° C. highlighting their stability (FIG. 29).

Table 5 below shows the percentage conversion for a number of bioconjugates formed. The data includes the original molecular weights of the proteins including the aldehyde handle, the expected molecular weight after conjugation and the measured molecular weight after conjugation. The Figures listed in the table show the mass spectrometry traces for each of the protein conjugates.

TABLE 4

Second order reactions rates for different organocatalysts and aldehyde donor groups.

| | Second Order Rate Constant ($M^{-1}$ $s^{-1}$) | | | | | | | |
|---|---|---|---|---|---|---|---|---|
| | Donor R group = $CH_3$ | | | | | | Donor R group = Phenyl-alanine | |
| Organocatalyst loading | | | | | | | | |
| Organocatalyst | 33 | 34 | 35 | 36 | 37 | 38 | 33 | 38 |
| 1 mM | 0.00009 | 0.0005 | >0.0001 | 0.0004 | 0.0022 | 0.0092 | 1.684 | 3.792 |
| 10 mM | 0.0033 | 0.0037 | 0.0009 | 0.0024 | 0.0166 | 0.0551 | 4.366 | 11.820 |
| 25 mM | 0.0100 | 0.0058 | 0.0016 | 0.0052 | 0.0252 | 0.0997 | 7.899 | 23.947 |

TABLE 5

Percentage conversion and MWs determined by EC-MS of bioconjugates formed by OPAL.

| Protein | Percentage conversion | Functional group | Original MW | Calculated MW | Measured MW | FIG. |
|---|---|---|---|---|---|---|
| GFP | >95 | Folate 27 | 28638 | 29730 | 29731 | 27A |
| GFP | >95 | Biotin 26 | 28638 | 29388 | 29388 | 27B |
| GFP | 40 | Azide 28 | 28638 | 29242 | 29241 | 27C |
| Myo-globin | >95 | Florescent 25 | 16950 | 17708 | 17711 | 28A |
| Myo-globin | >95 | Azide 28 | 16950 | — | 17617 | 28B |
| Thiore-doxin | >95 | Florescent 25 | 11644 | 12401 | 12401 | 28C |
| Thiore-doxin | >95 | Biotin 27 | 11644 | 12393 | 12396 | 28D |
| Thiore-doxin | >95 | Azide 28 | 11644 | 12311 | 12314 | — |

In accordance with the observations made in small molecule cross aldol reactions, the β-hydroxy aldehyde product of the OPAL also displayed no reactivity in further aldol reactions, however it was sought to determine whether this aldehyde may be reactive under alternative biologically compatible conditions which could enable construction of difficult to access differentially bi-functionalized proteins.

Screening of Aniline Catalysts for Aniline Organocatalyst-Mediated Oxime Ligation of β-Hydroxy Aldol-LYRAG Using peptide β-hydroxy-aldehyde-LYRAG 50 reactivity of the aldehyde as an electrophilic partner was screened in two high yielding literature bioconjugation reactions, the iso-Pictet-Spengler ligation and the 2-amino benzamidoxime (ABAO) ligation (both with optimal reactivity below pH 7) and although some conversion to bi-functionalized product was observed in both cases, yields were low (data not shown), reinforcing the relative stability of the β-hydroxy-aldehyde moiety compared to other aldehydes previously used in bioconjugation studies. Attention therefore was turned to the classical acid-catalyzed oxime ligation (pH 4.5 optimum), which proceeds more slowly at neutral pH but can be accelerated by the addition of aniline 56 as an organocatalyst. Studies using β-hydroxy-aldehyde-LYRAG 50, and an aminooxy nucleophile at pH 4.5 afforded an increased conversion (61%) to bi-functionalized product in the presence of 100 mM aniline 56, but unexpectedly conversion to the oxime product was further increased to 95% when the reaction was performed at neutral pH, which is a reversal of the precedent for oxime formation with other aldehyde handles (Table 6).

TABLE 6

Yields of oxime ligated glyoxyl-LYRAG.

| | | Conjugation Yield (%) | | | |
|---|---|---|---|---|---|
| pH | Catalyst | 56 | 57 | 58 | 59 |
| | 4.5 | 61 | 81 | 34 | precipitates |
| | 7.5 | 95 | 92 | 97 | 97 |

This trend was also evident when screening alternative aniline catalysts which have been previously reported for catalysis in hydrazone/oxime ligation, and also with alternative peptide and protein 1-hydroxy aldehyde substrates, suggesting a general trend in reactivity and improved biological compatibility.

Having established an unexpected pH dependence for accelerating oxime formation, the potential utility of the aniline organocatalyst-mediated oxime ligation in tandem with the OPAL for the construction of differentially functionalized proteins was tested.

Following the organocatalyst-mediated modification of both thioredoxin and myoglobin at neutral pH firstly using the OPAL to quantitatively install a fluorescent label into both proteins using 25 mM tetrazole 38, oxime ligation under optimized reaction conditions of 100 mM p-anisidine 57 organocatalyst in PB (50 mM, pH 7.5) was performed to install a biotin handle into thioredoxin, and a 2 kDa PEG chain into myoglobin, affording bi-functional constructs in excess of 70% overall conversion in both examples.

In order to further analyse dually modified protein constructs, SDS PAGE analysis, fluorescent imaging, and Western Blotting of thioredoxin 17, glyoxyl-thioredoxin 18, fluorescently labelled thioredoxin 47, and fluorescently, biotinylated thioredoxin 55 was performed. All proteins were observed by Coomassie stain, whilst only the fluorescently labelled samples 47 and 55 were detected in fluorescent imaging. Finally, only biotinylated sample 55 is observed by western blot following detection using a Streptavidin-HRP conjugate (FIG. 39).

Additionally, the bifuctionalized myoglobin construct was also analysed SDS-PAGE (FIG. 40). Coomassie staining of myoglobin 19, glyoxyl-myoglobin 21, mono-PEGylated myoglobin 67, fluorescently labelled myoglobin 41, and fluorescently labelled, PEGylated myoglobin 69 labelled proteins 41 and 69 were detected in the fluorescent imaging experiment. For protein samples treated with aminooxy PEG 2k 67 two protein bands are observed. Based on previously reported data of proteins that have been site-selectively modified with aminooxy PEG 67, a single addition of the polymer unit to the protein results in the observed protein band shifting by approximately 5 kDa. The results obtained for this experiment were therefore consistent with samples containing both unmodified protein (19 or 21) and PEGylated protein (67 or 69).

Figure 38:
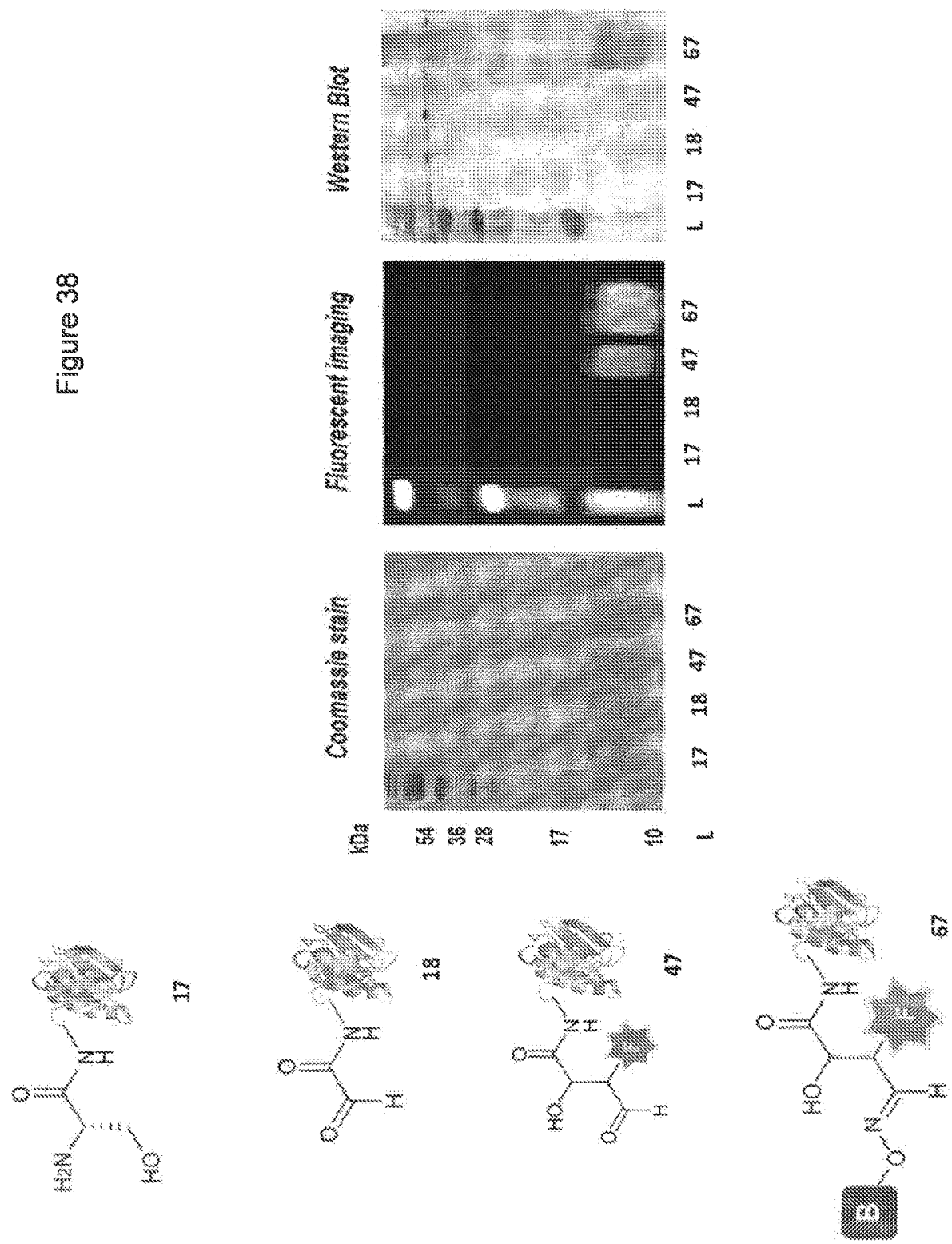
FIG. 38: is a schematic representation of the structures of thioredoxin 17, glyoxyl-thioredoxin 18, fluorescently labelled thioredoxin 47, and fluorescently, biotinylated thioredoxin 67 (left) and subsequent SDS-PAGE, fluorescent, and Western Blot analysis of each protein (L=Ladder).

Fluorescent Labeling and PEGylation of Myoglobin (FIG. 38)

An aliquot of glyoxyl-myolgobin 21 prepared as described according to literature (200 μM, 25 μl, 25 mM PB pH 7.5) was charged with an aliquot of tetrazole 38 (200 mM, 5 μl, 25 mM PB pH 7.5). The solution was then charged with fluorescent aryl probe 25 (2 mM, 10 μl, 25 mM PB pH 7.5). Following mixing by pipetting, the reaction was allowed to sit at 37° C. for 60 min without further agitation. Successful labelling was confirmed by LC-MS analysis.

An aliquot of fluorescently labelled myoglobin 41 (120 μL, prepared as described earlier) was buffer exchanged using a PD SpinTrap G-25 column (GE Healthcare Life Sciences, eluting into 5 mM PB pH 7.5). A 10 μL aliquot of the purified protein 41 was then charged with 0.2 M PB pH 7.5 (3.8 μL), p-anisidine 57 (1M, 0.4 μL, DMSO), and then charged with aminooxy PEG 2k (250 mM, 1.2 μL, 50 mM PB pH 7.0, pH adjusted to pH 7.0 using 1M HCl) and $H_2O$ (4.6 μL). Following mixing by pipetting, the reaction was allowed to sit at 37° C. for 42 h without further agitation.

Screening Aniline Catalysts for Retro-Aldol Mediated Decomposition of Aldol-LYRAG It was further considered whether a 'biomimetic' retro-aldol reaction of the β-hydroxy-aldehyde OPAL product may also be possible in the presence of an aniline 'organo-catalyst-trigger'.

In the absence of an aminoxy nucleophile, α-phenyl-β-hydroxy-aldehyde-LYRAG 50 underwent a retro-aldol reaction to regenerate the α-oxo-aldehyde 16A starting material at neutral pH in PB (200 mM) in the presence of aniline organocatalysts (56-59), with p-anisidine 57 the most effective with 52% conversion as is shown in Table 7.

TABLE 7

Percentage conversion of α-phenyl-β-hydroxy aldehyde-LYRAG 50 to glyoxyl-LYRAG 16A at different pH values with different aniline catalysts.

| | | Retro-aldol conversion (%) | | | | |
|---|---|---|---|---|---|---|
| pH | Catalyst | — | 56 | 57 | 58 | 59 |
| 4.5 | | 0 | 0 | 25 | 0 | precipitates |
| 7.5 | | 0 | 25 | 52 | 8 | 0 |

Intriguingly the retro-aldol reaction showed a buffer concentration dependence, with little or no retro-aldol release observed below 50 mM PB concentration, and no significant increase in conversion above 100 mM salt concentration (Table 8).

TABLE 8

Percentage conversion of α-phenyl-β-hydroxy aldehyde-LYRAG 50 to glyoxyl-LYRAG 16A at different buffer concentrations.

| Catalyst | PB, pH 7.5, conc. (Mm) | Retro-aldol conversion (%) |
|---|---|---|
| 57 | 10 | 0 |
| 57 | 50 | 13 |
| 57 | 100 | 50 |

Figure 31:
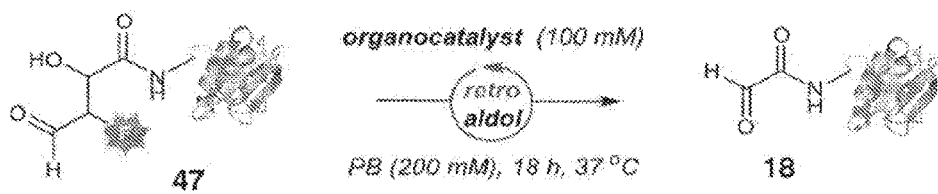
FIG. 31 illustrates a retro-aldol reaction carried out on conjugate 47 to produce glyoxal-thioredoxin 18 using an aniline catalyst.
Figure 32:
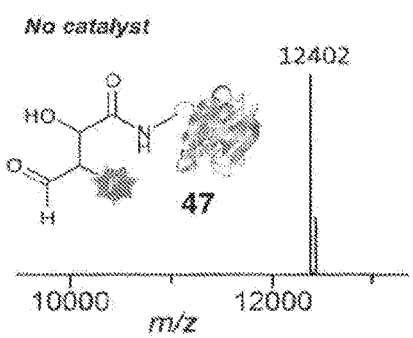
FIG. 32 shows a LC-MS spectrum of reaction products from the retro-aldol reaction shown in FIG. 31 when no catalyst is present. It can be seen that there is a single peak that corresponds to conjugate 47 indicating that with no catalyst present there is no removal of the functional group comprising the florescent moiety.
Figure 33:
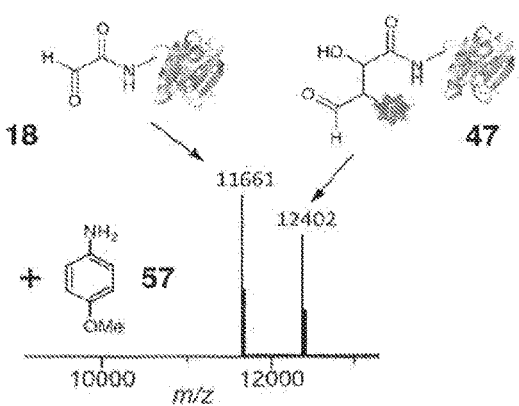
FIG. 33 shows an LC-MS spectrum of reaction products formed by the retro-aldol reaction shown in FIG. 31 using a p-anisidine 57 catalysts. The two peaks seen correspond to conjugate 47 including the florescent moiety and glyoxyl-thioredoxin 18 which has had the fluorescent moiety removed.

This retro-aldol mechanism was similarly operative on protein substrates, with thioredoxin bearing an OPAL derived fluorescently labelled β-hydroxy aldehyde 47, converted back to α-oxo-aldehyde starting material 18 in the presence of 100 mM p-anisidine 57 (FIG. 31). Notably no other degradation of the OPAL product was observed under the reaction conditions, and no retro-aldol observed in the absence of organocatalyst. This was confirmed by LC-MS analysis which with no catalysts present only showed only a single peak corresponding to the fluorescently labelled compound 47 (FIG. 32) and when a catalyst was present two peaks, one corresponding to the glyoxyl-thioredoxin 18 (m/z 11661) and one corresponding to the fluorescently labelled compound 47 (m/z 12402) where observed (FIG. 33).

In summary, an organocatalyst-mediated protein aldol ligation (OPAL) that proceeds rapidly at neutral pH has been designed. Furthermore, the reaction has been shown to be capable of installing a β-hydroxy-aldehyde handle which can provide access to differentially modified bioconjugates via a tandem-organocatalysed ligation accelerated at neutral pH. These bioconjugations have been validated using functional groups for the mild and rapid modification of a range of proteins. The ability to add and remove functional groups via the tandem aniline organocatalyst-mediated oxime ligation and retro-aldol reactions allows for site specific control of conjugation to a broad range of proteins and these reactions will likely prove broadly applicable in the reversible functionalization, multi-functionalization and immobilization of a broad range of biomolecules.

Example 2

Methods
Chemical Modification of hydrophilic acylated surface protein A (HASPA)
Preparation of liposomes for HASPA experiments Liposomes were prepared in order to investigate whether chemically myristoylated and palmitoylated HASPA associates with membrane lipids. Liposomes were prepared by using 1,2-Diacyl-s-glycero-3-phosphocholine (PC) and cholesterol (Ch). Lipids were solubilised in 9:1 chloroform-methanol (v/v), stocks were prepared at a 7:1 ratio of PC to Ch and the solvent was evaporated under $N_2$. Dried lipids were hydrated to a final concentration of 1 mM in lipid rehydration buffer (100 mM NaCl, 1 mM $CaCl_2$, and 50 mM Tris-Cl [pH 7.4]) or PBS+1 mM $CaCl_2$) for 30 min at room temperature. The rehydrated lipids were subjected to four freeze/thaw cycles in liquid nitrogen and a 45° C. water bath, and extruded through a 100 nm Nanosizer Liposome mini extruder (T & T Scientific Corporation) to produce liposomes. Dynamic light scattering (DLS) was used to confirm the size of the liposomes (data not shown).

Figure 34:
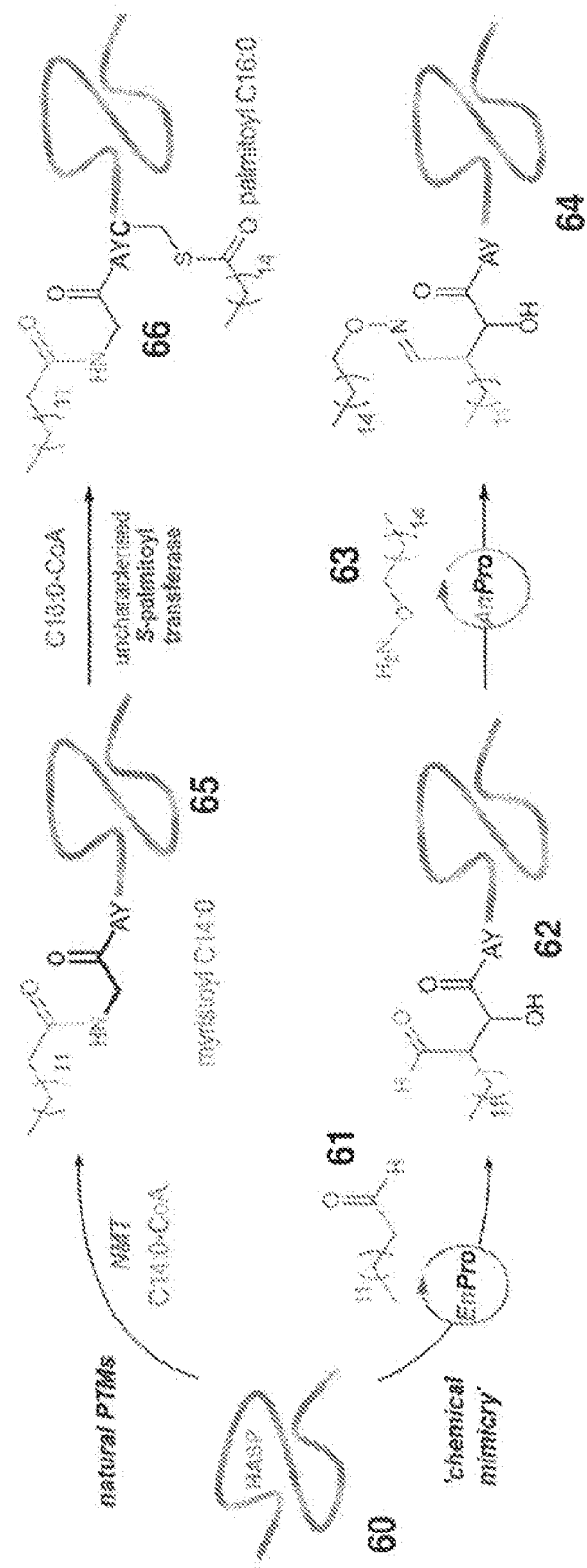
FIG. 34 illustrates the natural (top) and chemical (bottom) acylation of hydrophilic acylated surface protein A (HASPA) 60. Referring to the natural process, myristoyl-CoA (C14:0-CoA) is utilised as a precursor to attach myristoyl to glycine residue 1 (G1) of HASPA by the enzyme N-myristoyl transferase (NMT) to form 65. Subsequently the uncharacterised enzyme S-palmitoyl transferase attaches palmitoyl to cysteine residue 4 (C4) using palmitoyl-CoA (C16:0-CoA) as a precursor. This forms a dually acylated HASPA 66. The process designed to mimic this acetylation (chemical mimicry) utilises an OPAL reaction to conjugate myristaldehyde 61 to a glyoxyl-HASPA to form mono-acylated HASPA 62. The mono-acylated HASPA 62 is then subjected to an aniline organocatalyst-mediated oxime ligation using an aniline catalyst to ligate a palmitoyl aminoxy nucleophile 63 forming a dually acylated HASPA 64.

Formation of Myristoylated-G2S HASPA (FIG. 34)

An aliquot of glyoxyl-HASPA (formed using method previously described) (2.8 mM, 10 µl, 25 mM PB pH 7.5) was charged with an aliquot of L-proline 33 (800 mM, 8 µl, 25 mM PB pH 7.5). The solution was then charged with DMSO (6 µl) and myristaldehyde 61 (25 mM, 36 µl, DMSO). Following mixing by pipetting, the reaction was allowed to sit at 37° C. overnight without further agitation. Successful labelling was confirmed by LC-MS analysis (>95% conversion as judged by LC-MS).

To determine the ability of the bioconjugate 62 to effectively mimic myristoylation we next characterized, using 2D (1H,15N) HSQC protein NMR, an unmodified HASPA 60 and enzymatically myristoylated HASPA 65, acylated in vitro using purified recombinant N-myristoyltransferase.

The chemically myristoylated HASPA 62 was next subjected to tandem aniline organocatalyst-mediated oxime ligation using palmitoyl aminoxy nucleophile 63 to afford the dually acylated chemical mimic 64 in 100% conversion by ESI-MS.

The mono myristoylated mimic 62 and the dual acylated chemical mimic 64 were characterised using liposome sedimentation assays to assess their ability to mimic lipid modified HASPs in vivo.

Myristoylated HASPA

Figure 36:
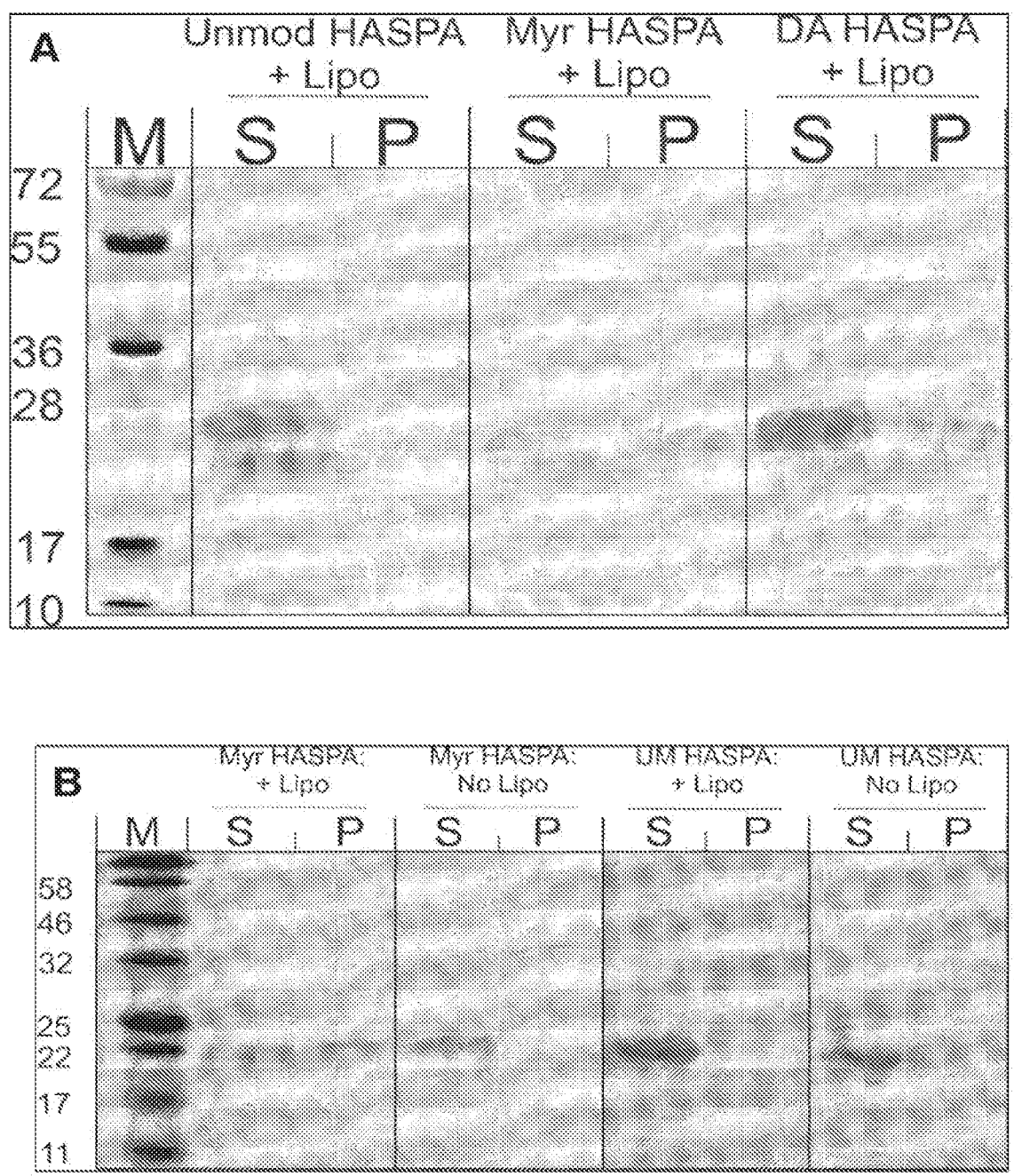
FIG. 36 shows SDS-PAGE gel analysis of chemically mono-acylated HASPA 62 (Myr HASPA) and chemically dual acylated HASPA 63 (DA HASPA) subjected to a liposome sedimentation assay in comparison to unmodified HASPA 60 (Unmod HASPA). M stands for markers, S stands for supernatant and P stands for liposome pellet. It can be seen from (A) that both the mono-acylated 62 and dual-acylated 63 HASPAs show lipid membrane association, whereas the unmodified HASPA 60 does not. This is further confirmed by the controls shown in (B) which includes samples that did not include liposomes (No Lipo).

Myristoylated G2S HASPA was dialysed into phosphate buffer saline using a Slide-A-Lyzer dialysis cassette (MwCO 3500 Da). After dialysis, the myristoylated G2S HASPA was quantified after SDS-PAGE analysis, by comparison to a known amount of unmodified G2S HASPA. ~40 µg of myristoylated G2S HASPA was recovered after dialysis. The recovered protein was lyophilised and stored at −20° C. For the lipid sedimentation assay, myristoylated G2S HASPA and unmodified G2S HASPA (20 µg) were incubated at room temperature for 45 min with PC:Ch liposomes (0.66 mM final conc.) in 75 µL of lipid rehydration buffer. No lipid and no protein controls were analysed alongside the binding assay. 10% of each sample was saved as the loading control. The samples were ultracentrifuged at 100 000 rpm (4° C.) for 1 h and the unbound fraction removed. The pellet was suspended in 65 µl of lipid rehydration buffer and the samples incubated at 37° C. for 30 min. The unbound and pellet fractions were analysed by SDS-PAGE (FIG. 36.) Approximately 50% of the myristoylated HASPA was retained in the liposome pellet fraction (FIG. 36, lane: 3). None of the unmodified G2S HASPA was retained in the lipid pellet fraction as expected (FIG. 36, lane: 3). The no liposome and no protein negative controls were as expected. These findings suggest that the chemically myristoylated HASPA is binding to the POPC: cholesterol liposomes.

Chemically Myristoylated and Palmitoylated HASPA

The chemically myristoylated G2S HASPA was desalted, lyophilised and resuspended in nickel binding buffer (PBS+

Figure 37A:
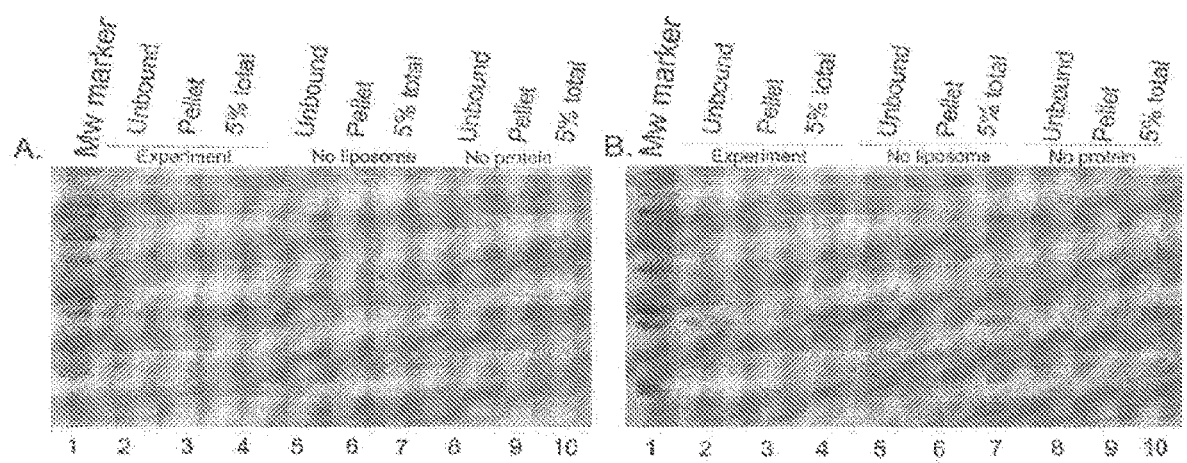
FIG. 37a is an SDS-PAGE gel illustrating that chemically myristoylated HASPA binds PC:Ch liposomes.
Figure 37B:
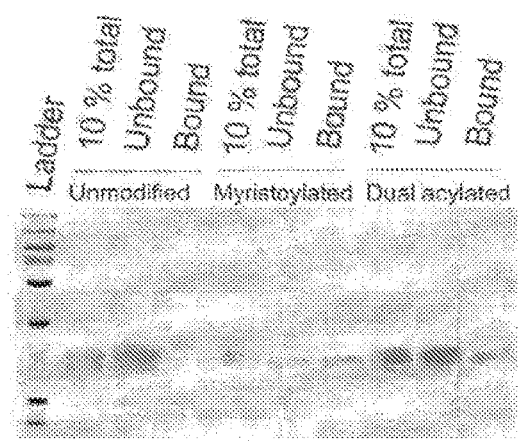
FIG. 37b shows an SDS-PAGE gel illustrating that chemically myristoylated and dual acylated G2S HASPA bind PC:Ch liposomes.

1% w/v sodium cholate, 20 mM imidazole). The dual acylated G2S HASPA was diluted to 20% v/v EtOH in nickel binding buffer. In order to remove any unreacted lipid/reagents, both the chemically myristoylated and the dual acylated G2S HASPA were purified using His Spintrap columns (GE Healthcare). The proteins were eluted from the His Spintrap columns using nickel elution buffer (PBS+1% w/v sodium cholate, 500 mM imidazole). The proteins were quantified after analysis by SDS-PAGE, by comparison to a known amount of unmodified G2S HASPA. For the liposome binding assays, unmodified, chemically myristoylated or dual acylated G2S HASPA (20 µg) was added to PC:Ch liposomes (50 µL of 1 mM suspension in PBS+1 mM $CaCl_2$) and made up to 100 µL in nickel elution buffer. The protein/liposome suspensions were dialysed into PBS for 16 h at 4° C. using D-tube Dialyzer Midi dialysis casettes (MERCK, MwCo 3.5 kDa). Due to precipitation of the dual acylated G2S HASPA in the absence of liposomes after dialysis, it was not possible to set up no liposome controls. After dialysis, the liposomes were sedimented by ultracentrifugation (100 000×g, 45 min, 4° C.). The liposome pellet was resuspended in 100 µL of PBS and the samples incubated at 37° C. for 30 min. The unbound and pellet fractions were analysed by SDS-PAGE. (FIG. 37b) Both the chemically myristoylated and the dual acylated G2S HASPA bound to PC:Ch liposomes. No liposome binding was observed in reactions with the unmodified G2S HASPA.

Results and Discussion

Figure 35:
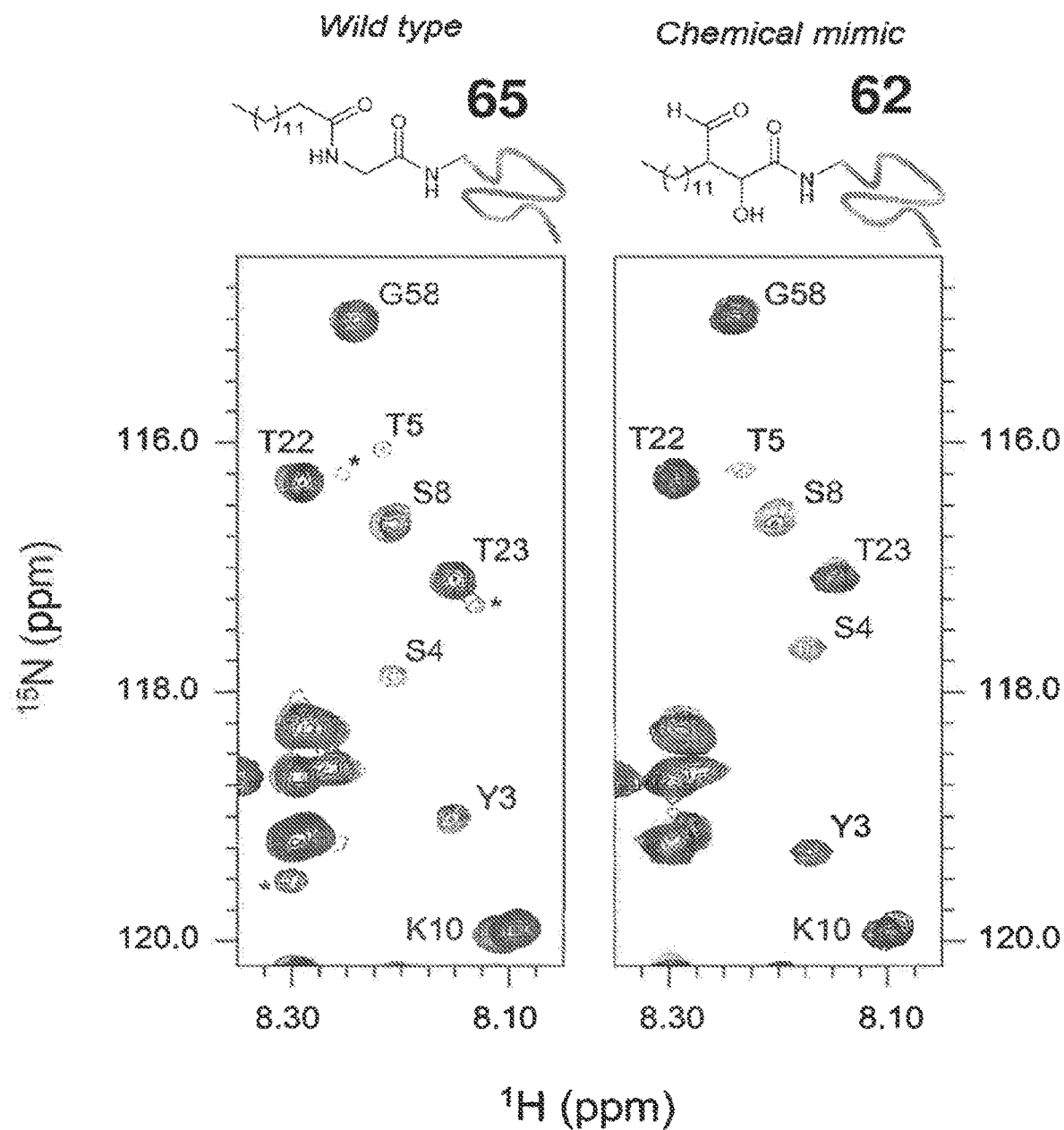
FIG. 35 shows spectra from 2D (1H,15N) heteronuclear single quantum coherence (HSQC) protein nuclear magnetic resonance (NMR) of mono-acylated HASPA 65 (enzymatically formed) (left panel) and mono-acylated HASPA 62 (chemically formed) (right panel). Light grey resonances on each spectrum correspond to unmodified HASPA 60. Both acylated proteins showed characteristic exchange broadening of resonances for residues near the N-terminus upon myristoylation, presumably due to self-association caused by the addition of the hydrophobic myristate moiety. Similarly, HSQC characterisation of the chemically myristoylated HASPA 62 is highly comparable to the spectrum of the enzymatically modified protein 65, demonstrating that the chemical modification of HASPA seemingly replicates the solution properties and structure of the enzymatically modified protein.

It was sought to explore the suitability of the tandem OPAL-oxime ligation in the 'chemical mimicry' of a natural dual post-translational modification (PTM) integral to the pathogenesis of the tropical disease Leishmaniasis. Highly immunogenic hydrophilic acylated surface proteins (HASPs) are present in all human infective *Leishmania* parasites, and although their expression is stage regulated during human infection, their exact role in the parasite lifecycle has yet to be determined. HASPs are non-classically, dually acylated at the N-terminus with both myristoyl (at Gly1) and palmitoyl (at Cys4) PTMs, thought to govern their ability associate with the plasma membrane. However, whilst co-translational myristoylation by the parasitic N-myristoyl transferase (NMT) can be recapitulated in vitro, the S-palmitoyltransferase enzyme and mechanism are unknown, which limits recombinant access to the natural dual acylated proteins for further study. Using myristoyl aldehyde as a donor and recombinantly expressed *Leishmania donovani* HASPA bearing an N-terminal α-oxo-aldehyde as a substrate we employed the OPAL to synthesise a chemical mimic 62 of the native acylated protein in quantitative conversion at neutral pH, with characterization by ESI-MS. To determine the ability of this bioconjugate to effectively mimic myristoylation the unmodified HASPA 60 and enzymatically myristoylated HASPA 65, acylated in vitro using purified recombinant N-myristoyl transferase, 2D (1H,15N) HSQC protein NMR was used. Following assignment of backbone nuclei, comparison of the spectra of both proteins revealed characteristic exchange broadening of resonances for residues near the N-terminus upon myristoylation (FIG. 35). Without being bound by theory, this may be due to self-association caused by the addition of the hydrophobic myristate moiety. Similarly, HSQC characterisation of the chemically myristoylated HASPA 62 was also performed and shown to be highly comparable to spectra of enzymatically modified protein 64, demonstrating that the chemical modification of HASPA seemingly replicates the solution properties and structure of the enzymatically modified protein.

Mono myristoylated mimic 62 and the dual acylated chemical mimic 64 were characterised using liposome sedimentation assays to assess their ability to mimic lipid modified HASPs in vivo, and shown to display far greater levels of in vitro association to model membranes than the unmodified HASPA 60. This can be seen by the difference in the distribution of protein seen in FIG. 36. This reinforces the putative in vivo role for the lipid PTMs in facilitating attachment to the parasite plasma membrane.

In conclusion, it is shown that the OPAL and aniline organocatalyst-mediated oxime ligation reactions can be used to produce synthetic analogues of protein conjugates not previously studied. The reactions can be performed in conditions that preserve the integrity of the protein and are simple and quick to perform.

REFERENCES

Plass, Tilman, et al. "Genetically Encoded Copper-Free Click Chemistry." Angewandte Chemie International Edition 50.17 (2011): 3878-3881.

Bi, Xiaobao, et al. "Thiazolidine-Masked α-Oxo Aldehyde Functionality for Peptide and Protein Modification." *Bioconjugate chemistry* 28.2 (2016): 325-329.

Diamantis, Nikolaos, and Udai Baneri. "Antibody-drug conjugates—an emerging class of cancer treatment." British journal of cancer 114.4 (2016): 362.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

SEQUENCES
GFP(Y39TAG)(Aequorea victoria): Lemke et al, 10.1002/
anie.201008178.X = amber stop codon. Base protein: P42212.
N-terminal FLAG tag (leading to decreased Met cleavage) and
C-terminal His tag, as well as Y39 (position 48 in sequencing
due to Met-FLAG) mutated to amber stop codon.

```
                                                      SEQ. ID. NO 1
         10         20         30         40         50         60
[M]DYKDDDDKV SKGEELFTGV VPILVELDGD VNGHKFSVSG EGEGDATXGK LTLKFICTTG 70         80         90        100        110        120
KLPVPWPTLV TTLTYGVQCF SRYPDHMKQH DFFKSAMPEG YVQERTIFFK DDGNYKTRAE 130        140        150        160        170        180
VKFEGDTLVN RIELKGIDFK EDGNILGHKL EYNYNSHNVY IMADKQKNGI KANFKIRHNI 190        200        210        220        230        240
EDGSVQLADH YQQNTPIGDG PVLLPDNHYL STQSALSKDP NEKRDHMVLL EFVTAAGITL

250
GMDELYKHHH HHH
```

S-GFP(Y39TAG): adapted from the above via site-directed mutagenesis
(Quikchange Lightning Multi-Site, Agilent).

```
                                                      SEQ. ID. NO 2
         10         20         30         40         50         60
[M]SYKDDDDKV SKGEELFTGV VPILVELDGD VNGHKFSVSG EGEGDATXGK LTLKFICTTG 70         80         90        100        110        120
KLPVPWPTLV TTLTYGVQCF SRYPDHMKQH DFFKSAMPEG YVQERTIFFK DDGNYKTRAE 130        140        150        160        170        180
VKFEGDTLVN RIELKGIDFK EDGNILGHKL EYNYNSHNVY IMADKQKNGI KANFKIRHNI 190        200        210        220        230        240
EDGSVQLADH YQQNTPIGDG PVLLPDNHYL STQSALSKDP NEKRDHMVLL EFVTAAGITL

250
GMDELYKHHH HHH
``` sfGFP(N150TAG): Addgene 85483.

```
                                                      SEQ. ID. NO 3
         10         20         30         40         50         60
[M]VSKGEELFT GVVPILVELD GDVNGHKFSV RGEGEGDATN GKLTLKFICT TGKLPVPWPT 70         80         90        100        110        120
LVTTLTYGVQ CFSRYPDHMK RDFFKSAMP EGYVQERTIS FKDDGTYKTR AEVKFEGDTL 130        140        150        160        170        180
VNRIELKGID FKEDGNILGH KLEYNFNSHX VYITADKQKN GIKANFKIRH NVEDGSVQLA 190        200        210        220        230        240
DHYQQNTPIG DGPVLLPDNH YLSTQSVLSK DPNEKRDHMV LLEFVTAAGI THGMDELYKG

SHHHHHH
```

---

The invention claimed is:

1. A method of modifying a polypeptide, the method comprising:
   a. contacting a first polypeptide comprising a first aldehyde moiety with:
      i. an aldehyde donor molecule comprising a second aldehyde moiety; and
      ii. a catalyst molecule, under conditions sufficient for an aldol reaction to occur between the first aldehyde group and the second aldehyde group, such that a second polypeptide is formed;
   wherein the second polypeptide comprises a third aldehyde moiety which is a beta-hydroxy aldehyde moiety and further wherein the catalyst molecule comprises a secondary amine moiety or an acid addition salt thereof.

2. The method of claim 1, wherein the polypeptide comprises at least one accessible aldehyde moiety.

3. The method according to claim 2, wherein the catalyst molecule comprises a cyclic secondary amine molecule.

4. The method according to claim 3 wherein the catalyst molecule comprises a secondary amine moiety of the formula $HNR^1R^2$ wherein $R^1$ and $R^2$ together with the nitrogen atom to which they are attached form a 3 to 7 membered ring.

5. The method according to claim 4, wherein the catalyst molecule is selected from the group consisting of:

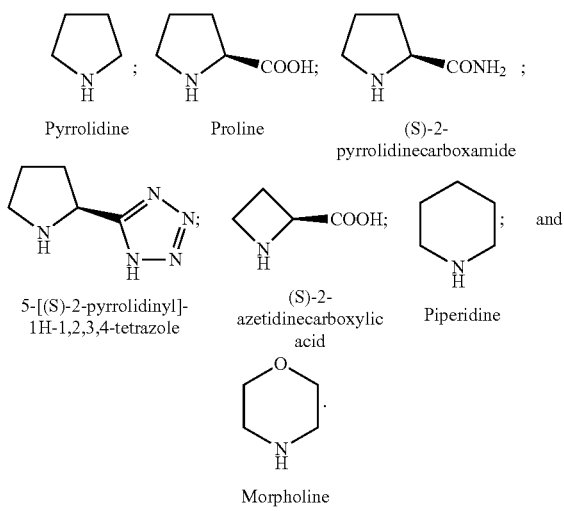

Pyrrolidine; Proline; (S)-2-pyrrolidinecarboxamide; 5-[(S)-2-pyrrolidinyl]-1H-1,2,3,4-tetrazole; (S)-2-azetidinecarboxylic acid; Piperidine; and Morpholine 6. The method according to claim 4, wherein the catalyst molecule comprises a substituted cyclic secondary amine molecule, wherein optionally the substituted cyclic secondary amine molecule is substituted pyrrolidine.

7. The method according to claim 6, wherein the catalyst molecule comprises a tetrazole-substituted cyclic secondary amine molecule.

8. The method according to claim 7, wherein optionally the tetrazole-substituted cyclic molecule is pyrrolidine substituted with tetrazole.

9. The method according to claim 8, wherein the tetrazole-substituted cyclic molecule is 2S-tetrazolylpyrrolidine.

10. The method according to claim 1, which comprises contacting the first polypeptide, the aldehyde donor molecule and the catalyst molecule in a buffer solution having a pH of between about 7 and 8 and/or at a temperature of between about 35° C. and about 38° C.

11. The method according to claim 1, wherein the first polypeptide comprises the first aldehyde moiety at an internal sequence of the first polypeptide; at a terminal loop, a C-terminus, or an N-terminus of the first polypeptide; on a solvent-accessible region of the first polypeptide when folded; and/or at a site of post-translational modification of the first polypeptide that is native or non-native to the amino acid sequence of the first polypeptide.

12. The method according to claim 1, wherein the second polypeptide comprises the third aldehyde moiety which is a beta hydroxy aldehyde moiety at an internal sequence of the second polypeptide; at a terminal loop, a C-terminus, or an N-terminus of the second polypeptide; on a solvent-accessible region of the second polypeptide when folded; and/or at a site of post-translational modification of the second polypeptide that is native or non-native to the amino acid sequence of the first polypeptide.

13. The method according to claim 1, wherein the aldehyde donor moiety further comprises a functional moiety and the method comprises incorporating the functional moiety into the second polypeptide, wherein the functional moiety is selected from the group consisting of a fluorescent label, an affinity tag, a conjugation moiety, a water soluble polymer and a targeting moiety and wherein the method comprises, if the functional moiety is a conjugation moiety, conjugating a further functional moiety to the second polypeptide via the conjugation moiety.

14. The method according to claim 13, which comprises incorporating the functional moiety into the second polypeptide at the alpha carbon position of the third aldehyde moiety.

15. The method according to claim 1, which comprises, prior to step (a), contacting a polypeptide with an oxidising reagent to generate the first aldehyde moiety on the polypeptide and form the first polypeptide, wherein:
(i) the oxidising reagent is periodate and wherein the method comprises oxidising a N-terminal serine residue or a N-terminal threonine residue to form an alpha-oxy aldehyde moiety, or
(ii) the oxidising reagent is pyridoxal-5-phosphate (PLP) and the method comprises oxidising a N-terminal lysine residue to form an alpha-oxy aldehyde moiety.

16. The method according to claim 1, which comprises, prior to step (a), a step of modifying a polypeptide to incorporate an aldehyde moiety at a pre-determined location to form the first polypeptide.

17. The method according to claim 1, further comprising a step of:
a). contacting the second polypeptide with:
i. a substituted or unsubstituted aniline catalyst molecule; and
ii. a substituted hydroxylamine molecule, wherein the substituent of the hydroxylamine molecule comprises a further functional moiety, under conditions sufficient for an oxime reaction to occur between the substituted hydroxylamine molecule and the beta-hydroxy aldehyde moiety to form a third polypeptide comprising the further function moiety.

18. A method according to claim 17, wherein the substituted hydroxylamine molecule has a structure of a formula selected from the group consisting of:

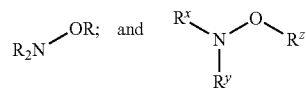

$R_2N$—OR; and $R^x$—N(—$R^y$)—O—$R^z$ wherein one or more, but not all of $R^x$, $R^y$ and $R^z$ is H.

19. A method according to claim 17, wherein the aniline catalyst molecule is selected from the group consisting of:

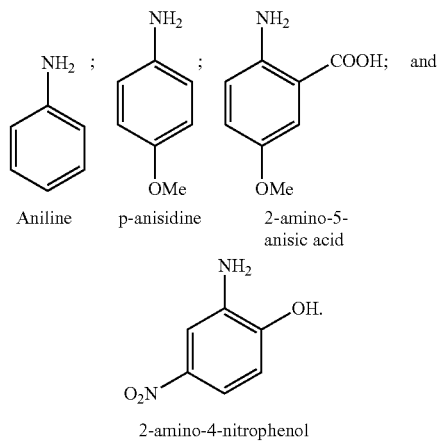

Aniline; p-anisidine; 2-amino-5-anisic acid; and 2-amino-4-nitrophenol

20. A method according to claim 17, which comprises contacting the polypeptide, the aniline catalyst in a buffer solution, wherein the buffer solution has a concentration of between at or below 100 mM and/or wherein the method comprises contacting the second polypeptide, the substituted or unsubstituted aniline catalyst molecule and the substituted hydroxylamine molecule in a buffer solution having a pH of between about 6.5 to about 8.

21. A method according to claim 20, which comprises contacting the second polypeptide, the substituted or unsubstituted aniline catalyst molecule and the substituted hydroxylamine molecule in a buffer solution having a pH of between about 7.3 to about 7.6.

\* \* \* \* \*